US012806429B2

(12) United States Patent
Wenning et al.

(10) Patent No.: US 12,806,429 B2
(45) Date of Patent: Nov. 24, 2026

(54) TRANSCUTANEOUS ENERGY TRANSFER

(71) Applicant: Kardion GmbH, Stuttgart (DE)

(72) Inventors: Leon Wenning, Stuttgart (DE); Inga Schellenberg, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 694 days.

(21) Appl. No.: 17/934,752

(22) Filed: Sep. 23, 2022

(65) Prior Publication Data

US 2023/0191141 A1 Jun. 22, 2023

Related U.S. Application Data

(60) Provisional application No. 63/253,220, filed on Oct. 7, 2021.

(51) Int. Cl.
*A61N 1/378* (2006.01)
*A61M 60/122* (2021.01)
(Continued)

(52) U.S. Cl.
CPC ....... *A61N 1/3787* (2013.01); *A61N 1/37282* (2013.01); *H02J 50/90* (2016.02); *A61M 60/122* (2021.01)

(58) Field of Classification Search
CPC ... A61N 1/3787; A61N 1/37282; H02J 50/90; H02J 7/0047; H02J 7/02; H02J 2310/23;
(Continued)

(56) References Cited

U.S. PATENT DOCUMENTS 2,254,698 A 9/1941 Hansen, Jr.
3,085,407 A 4/1963 Tomlinson
(Continued)

FOREIGN PATENT DOCUMENTS

CA 3 000 581 4/2017
CA 3 122 415 7/2020
(Continued)

OTHER PUBLICATIONS

Y. D. Chung and J. S. Kim, "Improved efficiency characteristics of wireless power charging system for superconducting MAGLEV train using inserted permanent magnets," 2018 IEEE International Symposium on Electromagnetic Compatibility, 2018, pp. 564-567 (Year: 2018).*

(Continued)

*Primary Examiner* — Jennifer Pitrak McDonald
*Assistant Examiner* — Christopher J Mutchler
(74) *Attorney, Agent, or Firm* — Knobbe, Martens, Olson & Bear, LLP

(57) ABSTRACT

The disclosure relates to a device for transcutaneously transmitting energy into a human body. The device may include an extracorporeally arranged transmission device that includes an induction charging coil and a sensor. Upon receiving an electrical current, the induction charging coil may provide a magnetic field to inductively transmit energy to an induction coil arranged intracorporeally, transcutaneously powering a medical device, such as a mechanical circulatory support system within in the body. The sensor may provide a position signal representing a relative position between the induction charging coil and the induction coil. In turn the position signal may be used to position the extracorporeal induction coil so that energy it is concentrically aligned with the intracorporeal induction coil and energy can be efficiently transferred to the medical device.

27 Claims, 28 Drawing Sheets

(51) Int. Cl.
*A61N 1/372* (2006.01)
*H02J 50/90* (2016.01)

(58) Field of Classification Search
CPC .... H02J 50/10; A61M 60/122; A61M 60/178; A61M 60/20; A61M 60/875
See application file for complete search history.

(56) References Cited

U.S. PATENT DOCUMENTS 3,088,323 A 5/1963 Welkowitz et al.
3,614,181 A 10/1971 Meeks
3,645,268 A 2/1972 Capote
3,747,998 A 7/1973 Klein et al.
3,790,878 A 2/1974 Brokaw
3,807,813 A 4/1974 Milligan
4,023,562 A 5/1977 Hynecek et al.
4,441,210 A 4/1984 Hochmair et al.
4,559,952 A 12/1985 Angelsen et al.
4,680,730 A 7/1987 Omoda
4,781,525 A 11/1988 Hubbard et al.
4,888,009 A 12/1989 Lederman et al.
4,888,011 A 12/1989 Kung et al.
4,889,131 A 12/1989 Salem et al.
4,896,754 A 1/1990 Carlson et al.
5,000,177 A 3/1991 Hoffmann et al.
5,045,051 A 9/1991 Milder et al.
5,195,877 A 3/1993 Kletschka
5,269,811 A 12/1993 Hayes
5,289,821 A 3/1994 Swartz
5,443,503 A 8/1995 Yamane
5,527,159 A 6/1996 Bozeman, Jr. et al.
5,581,038 A 12/1996 Lampropoulos
5,599,173 A 2/1997 Chen et al.
5,606,972 A 3/1997 Routh
5,613,935 A 3/1997 Jarvik
5,629,661 A 5/1997 Ooi et al.
5,662,115 A 9/1997 Torp
5,676,651 A 10/1997 Larson, Jr. et al.
5,690,674 A 11/1997 Diaz
5,695,471 A 12/1997 Wampler
5,702,430 A 12/1997 Larson, Jr. et al.
5,713,954 A 2/1998 Rosenberg et al.
5,720,771 A 2/1998 Snell
5,752,976 A 5/1998 Duffin et al.
5,766,207 A 6/1998 Potter et al.
5,814,900 A 9/1998 Esser
5,827,203 A 10/1998 Nita
5,843,141 A 12/1998 Bischoff et al.
5,865,759 A 2/1999 Koblanski
5,888,242 A 3/1999 Antaki et al.
5,904,646 A 5/1999 Jarvik
5,904,708 A 5/1999 Goedeke
5,911,685 A 6/1999 Siess et al.
5,964,694 A 10/1999 Siess et al.
5,980,465 A 11/1999 Elgas
5,982,153 A 11/1999 Nagal
6,007,478 A 12/1999 Siess et al.
6,024,704 A 2/2000 Meador et al.
6,053,873 A 4/2000 Govari et al.
6,058,958 A 5/2000 Benkowski et al.
6,149,405 A 11/2000 Abe et al.
6,167,765 B1 1/2001 Weitzel
6,176,822 B1 1/2001 Nix et al.
6,185,460 B1 2/2001 Thompson
6,190,324 B1 2/2001 Kieval et al.
6,212,430 B1 4/2001 Kung et al.
6,224,540 B1 5/2001 Lederman et al.
6,231,498 B1 5/2001 Pfeiffer et al.
6,245,007 B1 6/2001 Bedingham et al.
6,254,359 B1 7/2001 Aber
6,264,601 B1 7/2001 Jassawalla et al.
6,293,901 B1 9/2001 Prem
6,314,322 B1 11/2001 Rosenberg
6,324,430 B1 11/2001 Zarinetchi et al.
6,324,431 B1 11/2001 Zarinetchi et al.
6,351,048 B1 2/2002 Schob et al.
6,361,292 B1 3/2002 Chang et al.
6,366,817 B1 4/2002 Kung
6,389,318 B1 5/2002 Zarinetchi et al.
6,398,734 B1 6/2002 Cimochowski et al.
6,400,991 B1 6/2002 Kung
6,432,136 B1 8/2002 Weiss et al.
6,438,409 B1 8/2002 Malik et al.
6,442,434 B1 8/2002 Zarinetchi et al.
6,445,956 B1 9/2002 Laird et al.
6,471,713 B1 10/2002 Vargas et al.
6,496,733 B2 12/2002 Zarinetchi et al.
6,508,756 B1 1/2003 Kung et al.
6,512,949 B1 1/2003 Combs et al.
6,516,227 B1 2/2003 Meadows et al.
6,527,698 B1 3/2003 Kung et al.
6,530,876 B1 3/2003 Spence
6,540,658 B1 4/2003 Fasciano et al.
6,540,659 B1 4/2003 Milbocker
6,553,263 B1 4/2003 Meadows et al.
6,561,975 B1 5/2003 Pool et al.
6,579,257 B1 6/2003 Elgas et al.
6,592,620 B1 7/2003 Lancisi et al.
6,602,182 B1 8/2003 Milbocker
6,731,976 B2 5/2004 Penn et al.
6,879,126 B2 4/2005 Paden et al.
6,912,423 B2 6/2005 Ley et al.
6,949,066 B2 9/2005 Bearnson et al.
6,979,338 B1 12/2005 Loshakove et al.
7,010,954 B2 3/2006 Siess
7,022,100 B1 4/2006 Aboul-Hosn et al.
7,024,244 B2 4/2006 Muhlenberg et al.
7,062,331 B2 6/2006 Zarinetchi et al.
7,070,398 B2 7/2006 Olsen et al.
7,070,555 B2 7/2006 Siess
7,083,588 B1 8/2006 Shmulewitz et al.
7,155,291 B2 12/2006 Zarinetchi et al.
7,160,243 B2 1/2007 Medvedev
7,177,681 B2 2/2007 Xhu
7,238,151 B2 7/2007 Frazier
7,338,521 B2 3/2008 Antaki et al.
7,513,864 B2 4/2009 Kantrowitz et al.
7,520,850 B2 4/2009 Brockway
7,526,338 B1 4/2009 Gill
7,527,599 B2 5/2009 Hickey
7,591,777 B2 9/2009 LaRose
7,744,560 B2 6/2010 Struble
7,762,941 B2 7/2010 Jarvik
7,794,384 B2 9/2010 Sugiura et al.
7,819,916 B2 10/2010 Yaegashi
7,850,594 B2 12/2010 Sutton et al.
7,856,335 B2 12/2010 Morello et al.
7,862,501 B2 1/2011 Woodward et al.
7,942,805 B2 5/2011 Shambaugh, Jr.
7,951,129 B2 5/2011 Chinchoy
7,959,551 B2 6/2011 Jarvik
7,963,905 B2 6/2011 Salmonsen et al.
7,988,728 B2 8/2011 Ayre
8,012,079 B2 9/2011 Delgado, III
8,075,472 B2 12/2011 Zilbershlag et al.
8,088,059 B2 1/2012 Jarvik
8,211,028 B2 7/2012 Karamanoglu et al.
8,231,519 B2 7/2012 Reichenbach et al.
8,382,830 B2 2/2013 Maher et al.
8,419,609 B2 4/2013 Shambaugh, Jr. et al.
8,435,182 B1 5/2013 Tamura
8,449,444 B2 5/2013 Poirier
8,461,817 B2 6/2013 Martin et al.
8,489,200 B2 7/2013 Zarinetchi et al.
8,545,380 B2 10/2013 Farnan et al.
8,562,508 B2 10/2013 Dague et al.
8,585,572 B2 11/2013 Mehmanesh
8,591,393 B2 11/2013 Walters et al.
8,594,790 B2 11/2013 Kjellstrom et al.
8,608,635 B2 12/2013 Yomtov et al.
8,612,002 B2 12/2013 Faltys et al.
8,617,239 B2 12/2013 Reitan
8,620,447 B2 12/2013 D'Ambrosio et al.
8,622,949 B2 1/2014 Zafirelis et al.

(56) References Cited

U.S. PATENT DOCUMENTS

| | | | |
|---|---|---|---|
| 8,657,875 B2 | 2/2014 | Kung et al. | |
| 8,715,151 B2 | 5/2014 | Poirier | |
| 8,727,959 B2 | 5/2014 | Reitan et al. | |
| 8,747,293 B2 | 6/2014 | Arndt et al. | |
| 8,766,788 B2 | 7/2014 | D'Ambrosio | |
| 8,794,989 B2 | 8/2014 | Kearsley et al. | |
| 8,827,890 B2 | 9/2014 | Lee et al. | |
| 8,849,398 B2 | 9/2014 | Evans | |
| 8,862,232 B2 | 10/2014 | Zarinetchi et al. | |
| 8,864,643 B2 | 10/2014 | Reichenbach et al. | |
| 8,864,644 B2 | 10/2014 | Yomtov | |
| 8,870,739 B2 | 10/2014 | LaRose et al. | |
| 8,876,685 B2 | 11/2014 | Crosby et al. | |
| 8,882,477 B2 | 11/2014 | Fritz, IV et al. | |
| 8,888,728 B2 | 11/2014 | Aboul-Hosn et al. | |
| 8,897,873 B2 | 11/2014 | Schima et al. | |
| 8,900,114 B2 | 12/2014 | Tansley et al. | |
| 8,903,492 B2 | 12/2014 | Soykan et al. | |
| 8,961,389 B2 | 2/2015 | Zilbershlag | |
| 9,002,468 B2 | 4/2015 | Shea et al. | |
| 9,002,469 B2 | 4/2015 | D'Ambrosio | |
| 9,028,392 B2 | 5/2015 | Shifflette | |
| 9,033,863 B2 | 5/2015 | Jarvik | |
| 9,071,182 B2 | 6/2015 | Yoshida et al. | |
| 9,091,271 B2 | 7/2015 | Bourque | |
| 9,192,705 B2 | 11/2015 | Yanai et al. | |
| 9,220,826 B2 | 12/2015 | D'Ambrosio | |
| 9,283,314 B2 | 3/2016 | Prasad et al. | |
| 9,297,735 B2 | 3/2016 | Graichen et al. | |
| 9,308,305 B2 | 4/2016 | Chen et al. | |
| 9,345,824 B2 | 5/2016 | Mohl et al. | |
| 9,364,592 B2 | 6/2016 | McBride | |
| 9,381,286 B2 | 7/2016 | Spence et al. | |
| 9,427,508 B2 | 8/2016 | Reyes et al. | |
| 9,427,509 B2 * | 8/2016 | Vodermayer | H02J 50/80 |
| 9,440,013 B2 | 9/2016 | Dowling et al. | |
| 9,452,249 B2 | 9/2016 | Kearsley et al. | |
| 9,456,898 B2 | 10/2016 | Barnes et al. | |
| 9,474,840 B2 | 10/2016 | Siess | |
| 9,486,566 B2 | 11/2016 | Siess | |
| 9,492,600 B2 | 11/2016 | Strueber et al. | |
| 9,492,601 B2 | 11/2016 | Casas et al. | |
| 9,511,179 B2 | 12/2016 | Casas et al. | |
| 9,539,094 B2 | 1/2017 | Dale et al. | |
| 9,550,017 B2 | 1/2017 | Spanier et al. | |
| 9,555,173 B2 | 1/2017 | Spanier | |
| 9,555,175 B2 | 1/2017 | Bulent et al. | |
| 9,556,873 B2 | 1/2017 | Yanai et al. | |
| 9,561,362 B2 | 2/2017 | Malinowski | |
| 9,566,374 B2 | 2/2017 | Spence et al. | |
| 9,569,985 B2 | 2/2017 | Alkhatib et al. | |
| 9,579,433 B2 | 2/2017 | LaRose et al. | |
| 9,592,397 B2 | 3/2017 | Hansen et al. | |
| 9,603,984 B2 | 3/2017 | Romero et al. | |
| 9,616,107 B2 | 4/2017 | VanAntwerp et al. | |
| 9,636,442 B2 | 5/2017 | Karmon et al. | |
| 9,656,010 B2 | 5/2017 | Burke | |
| 9,669,142 B2 | 6/2017 | Spanier et al. | |
| 9,669,144 B2 | 6/2017 | Spanier et al. | |
| 9,713,701 B2 | 7/2017 | Sarkar et al. | |
| 9,717,831 B2 | 8/2017 | Schuermann | |
| 9,724,083 B2 | 8/2017 | Quadri et al. | |
| 9,744,282 B2 | 8/2017 | Rosenberg et al. | |
| 9,759,222 B2 | 9/2017 | Zimmermann et al. | |
| 9,789,236 B2 | 10/2017 | Bonde | |
| 9,800,172 B1 | 10/2017 | Leabman | |
| 9,833,314 B2 | 12/2017 | Corbett | |
| 9,833,550 B2 | 12/2017 | Siess | |
| 9,833,611 B2 | 12/2017 | Govea et al. | |
| 9,848,899 B2 | 12/2017 | Sliwa et al. | |
| 9,878,087 B2 | 1/2018 | Richardson et al. | |
| 9,919,086 B2 | 3/2018 | Dowling et al. | |
| 9,943,236 B2 | 4/2018 | Bennett et al. | |
| 9,950,102 B2 | 4/2018 | Spence et al. | |
| 9,974,894 B2 | 5/2018 | Morello | |
| 9,999,714 B2 | 6/2018 | Spanier et al. | |
| 10,010,412 B2 | 7/2018 | Taft | |
| 10,010,662 B2 | 7/2018 | Wiesener et al. | |
| 10,029,037 B2 | 7/2018 | Muller et al. | |
| 10,052,420 B2 | 8/2018 | Medvedev et al. | |
| 10,123,875 B2 | 11/2018 | Wildhirt et al. | |
| 10,124,102 B2 | 11/2018 | Bulent et al. | |
| 10,143,571 B2 | 12/2018 | Spence et al. | |
| 10,148,126 B2 | 12/2018 | Hoarau | |
| 10,220,129 B2 | 3/2019 | Ayre et al. | |
| 10,293,090 B2 | 5/2019 | Bonde et al. | |
| 10,322,217 B2 | 6/2019 | Spence | |
| 10,327,858 B2 | 6/2019 | Dumesnil | |
| 10,342,906 B2 | 7/2019 | D'Ambrosio et al. | |
| 10,350,342 B2 | 7/2019 | Thomas et al. | |
| 10,357,598 B2 | 7/2019 | Aboul-Hosn et al. | |
| 10,376,162 B2 | 8/2019 | Edelman et al. | |
| 10,413,651 B2 | 9/2019 | Yomtov et al. | |
| 10,426,563 B2 | 10/2019 | Dumesnil | |
| 10,463,508 B2 | 11/2019 | Spence et al. | |
| 10,493,191 B2 | 12/2019 | Whisenant et al. | |
| 10,500,322 B2 | 12/2019 | Karch | |
| 10,549,020 B2 | 2/2020 | Spence et al. | |
| 10,561,771 B2 | 2/2020 | Heilman et al. | |
| 10,561,772 B2 | 2/2020 | Schumacher | |
| 10,561,773 B2 | 2/2020 | Ferrari et al. | |
| 10,589,013 B2 | 3/2020 | Bourque | |
| 10,660,998 B2 | 5/2020 | Hodges | |
| 10,668,195 B2 | 6/2020 | Flores | |
| 10,732,583 B2 | 8/2020 | Rudser | |
| 10,808,704 B2 | 10/2020 | Siess et al. | |
| 10,857,275 B2 | 12/2020 | Granegger | |
| 10,864,308 B2 | 12/2020 | Muller et al. | |
| 10,944,293 B2 | 3/2021 | Nakao | |
| 11,000,282 B2 | 5/2021 | Schuelke et al. | |
| D923,797 S | 6/2021 | Parks et al. | |
| D923,798 S | 6/2021 | Goulet et al. | |
| 11,027,114 B2 | 6/2021 | D'Ambrosio et al. | |
| RE48,649 E | 7/2021 | Siess | |
| 11,056,878 B2 | 7/2021 | Gao et al. | |
| 11,065,437 B2 | 7/2021 | Aber et al. | |
| 11,071,857 B2 | 7/2021 | Sun | |
| 11,103,715 B2 | 8/2021 | Fort | |
| 11,110,265 B2 | 9/2021 | Johnson | |
| 11,116,959 B2 | 9/2021 | Alexander et al. | |
| 11,121,580 B2 | 9/2021 | Partovi | |
| 11,147,960 B2 | 10/2021 | Spanier et al. | |
| 11,179,559 B2 | 11/2021 | Hansen | |
| 11,224,737 B2 | 1/2022 | Petersen et al. | |
| 11,266,502 B1 | 3/2022 | Wallace | |
| 11,273,299 B2 | 3/2022 | Wolman et al. | |
| 11,285,310 B2 | 3/2022 | Curran et al. | |
| 11,291,826 B2 | 4/2022 | Tuval et al. | |
| 11,298,524 B2 | 4/2022 | El Katerji et al. | |
| 11,316,371 B1 | 4/2022 | Partovi et al. | |
| 11,317,988 B2 | 5/2022 | Hansen et al. | |
| 11,320,382 B2 | 5/2022 | Aikawa | |
| 11,324,395 B2 | 5/2022 | Banik et al. | |
| 11,331,082 B2 | 5/2022 | Itoh et al. | |
| 11,344,717 B2 | 5/2022 | Kallenbach et al. | |
| 11,351,359 B2 | 6/2022 | Clifton et al. | |
| 11,351,360 B2 | 6/2022 | Rudser et al. | |
| 11,357,438 B2 | 6/2022 | Stewart et al. | |
| 11,357,968 B2 | 6/2022 | El Katerji et al. | |
| 11,368,081 B2 | 6/2022 | Vogt et al. | |
| 11,369,785 B2 | 6/2022 | Callaway et al. | |
| 11,369,786 B2 | 6/2022 | Menon et al. | |
| 11,389,639 B2 | 7/2022 | Casas | |
| 11,389,641 B2 | 7/2022 | Nguyen et al. | |
| 11,406,483 B2 | 8/2022 | Wirbisky et al. | |
| 11,406,520 B2 | 8/2022 | Lam | |
| 11,406,802 B2 | 8/2022 | DeGraaf et al. | |
| 11,413,443 B2 | 8/2022 | Hodges et al. | |
| 11,413,444 B2 | 8/2022 | Nix et al. | |
| 11,439,806 B2 | 9/2022 | Kimball et al. | |
| 11,471,692 B2 | 10/2022 | Aghassian et al. | |
| 11,478,629 B2 | 10/2022 | Harjes et al. | |
| 11,497,906 B2 | 11/2022 | Grace et al. | |
| 11,517,737 B2 | 12/2022 | Struthers et al. | |

(56) References Cited

U.S. PATENT DOCUMENTS 11,517,738 B2 12/2022 Wisniewski
11,517,740 B2 12/2022 Agarwa et al.
11,524,165 B2 12/2022 Tan et al.
11,527,322 B2 12/2022 Agnello et al.
11,529,062 B2 12/2022 Moyer et al.
11,529,508 B2 12/2022 Jablonsk et al.
11,534,596 B2 12/2022 Schafir et al.
11,577,068 B2 2/2023 Spence et al.
11,581,083 B2 2/2023 El Katerji et al.
11,583,671 B2 2/2023 Nguyen et al.
11,596,727 B2 3/2023 Siess et al.
11,602,624 B2 3/2023 Siess et al.
11,616,397 B2 3/2023 Schilling
11,622,695 B1 4/2023 Adriola et al.
11,628,293 B2 4/2023 Gandhi et al.
11,642,512 B2 5/2023 Schilling
11,648,386 B2 5/2023 Poirer
11,653,841 B2 5/2023 Reyes et al.
11,666,746 B2 6/2023 Ferrari et al.
11,668,321 B2 6/2023 Richert et al.
11,682,924 B2 6/2023 Hansen et al.
11,684,276 B2 6/2023 Cros et al.
11,684,769 B2 6/2023 Harjes et al.
11,689,057 B2 6/2023 Hansen
11,699,551 B2 7/2023 Diekhans et al.
11,724,091 B2 8/2023 Siess et al.
11,745,005 B2 9/2023 Delgado, III
11,752,354 B2 9/2023 Stotz et al.
11,759,622 B2 9/2023 Siess et al.
11,779,234 B2 10/2023 Harjes et al.
11,781,550 B2 10/2023 Siess et al.
11,781,551 B2 10/2023 Yanai et al.
11,790,487 B2 10/2023 Barbato et al.
11,793,994 B2 10/2023 Josephy et al.
11,804,767 B2 10/2023 Vogt et al.
11,806,116 B2 11/2023 Tuval et al.
11,806,517 B2 11/2023 Petersen
11,813,079 B2 11/2023 Lau et al.
11,824,381 B2 11/2023 Conyers et al.
11,826,127 B2 11/2023 Casas
11,832,793 B2 12/2023 McWeeney et al.
11,832,868 B2 12/2023 Smail et al.
11,837,364 B2 12/2023 Lee et al.
11,844,592 B2 12/2023 Tuval et al.
11,844,940 B2 12/2023 D'Ambrosio et al.
11,850,073 B2 12/2023 Wright et al.
11,850,414 B2 12/2023 Schenck et al.
11,850,415 B2 12/2023 Schwammenthal et al.
11,857,345 B2 1/2024 Hanson et al.
11,864,878 B2 1/2024 Duval et al.
11,872,384 B2 1/2024 Cotter
11,881,721 B2 1/2024 Araujo et al.
11,883,207 B2 1/2024 El Katerji et al.
11,890,082 B2 2/2024 Cros et al.
11,896,199 B2 2/2024 Lent et al.
11,903,657 B2 2/2024 Geric et al.
11,906,411 B2 2/2024 Graichen et al.
11,911,550 B2 2/2024 Itamochi et al.
11,923,093 B2 3/2024 Moffitt et al.
11,931,073 B2 3/2024 Walsh et al.
11,931,528 B2 3/2024 Rohl et al.
11,986,274 B2 5/2024 Edelman
11,996,699 B2 5/2024 Vasconcelos Araujo et al.
12,011,583 B2 6/2024 Wang
12,017,076 B2 6/2024 Tan et al.
12,023,476 B2 7/2024 Tuval et al.
12,029,891 B2 7/2024 Siess et al.
12,053,624 B2 8/2024 Alexander et al.
12,059,559 B2 8/2024 Muller et al.
12,076,544 B2 9/2024 Siess et al.
12,097,016 B2 9/2024 Goldvasser
12,102,815 B2 10/2024 Dhaliwal et al.
12,102,835 B2 10/2024 Stotz et al.
12,144,650 B2 11/2024 Spanier et al.
12,144,976 B2 11/2024 Baumbach et al.
12,150,647 B2 11/2024 Schuelke et al.
12,178,554 B2 12/2024 Stotz et al.
12,179,009 B2 12/2024 El Katerji et al.
12,194,287 B2 1/2025 Kassel et al.
12,201,821 B2 1/2025 Schlebusch et al.
12,222,267 B2 2/2025 Stotz et al.
12,230,868 B2 2/2025 Wenning et al.
12,233,250 B2 2/2025 Stotz et al.
12,251,551 B2 3/2025 Liu et al.
12,257,424 B2 3/2025 Schlebusch et al.
12,268,861 B2 4/2025 D'Ambrosio et al.
12,296,158 B2 5/2025 Higgins et al.
12,310,621 B2 5/2025 Murphy
12,310,708 B2 5/2025 Schlebusch et al.
12,311,160 B2 5/2025 Schlebusch et al.
12,324,906 B2 6/2025 Baumbach et al.
12,329,501 B2 6/2025 Moyer et al.
12,329,956 B2 6/2025 Sunagawa
12,329,959 B2 6/2025 Hassan et al.
12,343,518 B2 7/2025 Tuval et al.
12,364,854 B2 7/2025 Wang
12,377,256 B2 8/2025 Stotz et al.
12,383,727 B2 8/2025 Kassel et al.
12,390,168 B2 8/2025 Katerji et al.
12,400,788 B2 8/2025 Diekhans et al.
12,403,296 B2 9/2025 Baumbach et al.
12,409,311 B2 9/2025 Jahangir et al.
12,409,313 B2 9/2025 Eggen et al.
12,424,315 B2 9/2025 Nix et al.
12,434,060 B2 10/2025 Tan et al.
12,440,665 B2 10/2025 Tuval et al.
12,445,278 B2 10/2025 Agnello
12,447,327 B2 10/2025 Stotz
12,451,230 B2 10/2025 El Katerji et al.
12,476,002 B2 11/2025 El Katerji et al.
12,476,488 B2 11/2025 Araujo et al.
12,478,266 B2 11/2025 Edelman et al.
12,478,267 B2 11/2025 Schlebusch et al.
12,478,774 B2 11/2025 Muller
12,491,357 B2 12/2025 Baumbach et al.
12,494,292 B2 12/2025 El Katerji et al.
12,502,524 B2 12/2025 Stigloher et al.
12,508,418 B2 12/2025 Baumbach et al.
12,521,543 B2 1/2026 Egler
12,521,546 B2 1/2026 Siess et al.
12,544,556 B2 2/2026 Tuval et al.
12,546,320 B2 2/2026 Siess et al.
12,551,687 B2 2/2026 Grauwinkel et al.
12,569,671 B2 3/2026 Schellenberg et al.
12,575,841 B2 3/2026 Gao et al.
12,576,261 B2 3/2026 Vasudevan Jalaja et al.
12,576,263 B2 3/2026 Baumbach et al.
2001/0016686 A1 8/2001 Okada et al.
2001/0039828 A1 11/2001 Shin et al.
2002/0022785 A1 2/2002 Romano
2002/0082585 A1 6/2002 Carroll et al.
2002/0093412 A1 7/2002 Morrison
2002/0147495 A1 10/2002 Petroff
2002/0151761 A1 10/2002 Viole et al.
2002/0177324 A1 11/2002 Metzler
2003/0040765 A1 2/2003 Breznock
2003/0125766 A1 7/2003 Ding
2003/0130581 A1 7/2003 Salo et al.
2003/0139643 A1 7/2003 Smith et al.
2003/0167002 A1 9/2003 Nagar et al.
2003/0191357 A1 10/2003 Frazier
2003/0199727 A1 10/2003 Burke
2004/0022640 A1 2/2004 Siess et al.
2004/0034411 A1 2/2004 Quijano
2004/0044266 A1 3/2004 Siess et al.
2004/0065143 A1 4/2004 Husher
2004/0102674 A1 5/2004 Zadini et al.
2004/0124979 A1* 7/2004 Medema .............. A61N 1/3904
340/539.18
2004/0130009 A1 7/2004 Tangpuz
2004/0167376 A1 8/2004 Peters et al.
2004/0167410 A1 8/2004 Hettrick
2004/0225177 A1 11/2004 Coleman et al.
2004/0241019 A1 12/2004 Goldowsky

(56) References Cited

U.S. PATENT DOCUMENTS

2004/0260346 A1 12/2004 Overall et al.
2005/0001324 A1 1/2005 Dunn
2005/0006083 A1 1/2005 Chen et al.
2005/0046044 A1 3/2005 Theuss
2005/0085683 A1 4/2005 Bolling et al.
2005/0107658 A1 5/2005 Brockway
2005/0107847 A1 5/2005 Gruber et al.
2005/0126268 A1 6/2005 Ouriev et al.
2006/0004423 A1 1/2006 Boveja et al.
2006/0069837 A1* 3/2006 Zhang .................. G06F 1/1632 710/303
2006/0108697 A1 5/2006 Wang
2006/0108901 A1 5/2006 Mao-Chin
2006/0122583 A1 6/2006 Pesach et al.
2006/0190036 A1 8/2006 Wendel et al.
2006/0196277 A1 9/2006 Allen et al.
2006/0217785 A1 9/2006 Matei
2006/0229488 A1 10/2006 Ayre et al.
2006/0287600 A1 12/2006 McEowen
2006/0287604 A1 12/2006 Hickey
2007/0060787 A1 3/2007 Peters et al.
2007/0069354 A1 3/2007 Dangelmaier
2007/0073352 A1 3/2007 Euler et al.
2007/0088214 A1 4/2007 Shuros et al.
2007/0129767 A1 6/2007 Wahlstrand
2007/0142696 A1 6/2007 Crosby et al.
2007/0156006 A1 7/2007 Smith et al.
2007/0255352 A1 11/2007 Roline et al.
2007/0266778 A1 11/2007 Corey et al.
2007/0282209 A1 12/2007 Lui et al.
2007/0299325 A1 12/2007 Farrell et al.
2008/0015481 A1 1/2008 Bergin et al.
2008/0015517 A1 1/2008 Geistert et al.
2008/0079392 A1 4/2008 Baarman et al.
2008/0082005 A1 4/2008 Stern et al.
2008/0091239 A1 4/2008 Johansson et al.
2008/0097595 A1 4/2008 Gabbay
2008/0102096 A1 5/2008 Molin et al.
2008/0108901 A1 5/2008 Baba et al.
2008/0108930 A1 5/2008 Weitzel et al.
2008/0133006 A1 6/2008 Crosby et al.
2008/0146996 A1 6/2008 Smisson
2008/0210016 A1 9/2008 Zwirn et al.
2008/0211455 A1 9/2008 Park et al.
2008/0238364 A1 10/2008 Weber
2008/0248614 A1 10/2008 Yang
2008/0262289 A1 10/2008 Goldowsky
2008/0262361 A1 10/2008 Gutfinger et al.
2008/0266922 A1 10/2008 Mumtaz et al.
2008/0269822 A1 10/2008 Ljungstrom et al.
2008/0275339 A1 11/2008 Thiemann et al.
2008/0287799 A1 11/2008 Hall
2008/0306328 A1 12/2008 Ercolani
2009/0004037 A1 1/2009 Ito
2009/0010462 A1 1/2009 Ekchian et al.
2009/0024042 A1 1/2009 Nunez et al.
2009/0025459 A1 1/2009 Zhang et al.
2009/0064755 A1 3/2009 Fleischli et al.
2009/0105799 A1 4/2009 Hekmat et al.
2009/0131765 A1 5/2009 Roschak et al.
2009/0134711 A1 5/2009 Issa et al.
2009/0198307 A1 8/2009 Mi et al.
2009/0198312 A1 8/2009 Barker
2009/0204163 A1 8/2009 Shuros et al.
2009/0204205 A1 8/2009 Larose et al.
2009/0212637 A1* 8/2009 Baarman .................. H04B 5/79 307/104
2009/0276016 A1 11/2009 Phillips et al.
2009/0312650 A1 12/2009 Maile et al.
2010/0010354 A1 1/2010 Skerl et al.
2010/0010582 A1 1/2010 Carbunaru
2010/0082099 A1 4/2010 Vodermayer et al.
2010/0160801 A1 6/2010 Takatani et al.
2010/0191035 A1 7/2010 Kang et al.
2010/0219967 A1 9/2010 Kaufmann
2010/0268017 A1 10/2010 Siess
2010/0280568 A1 11/2010 Bulkes et al.
2010/0298625 A1 11/2010 Reichenbach et al.
2010/0312310 A1 12/2010 Meskens
2010/0324378 A1 12/2010 Tran et al.
2010/0331918 A1 12/2010 Digiore et al.
2010/0331920 A1 12/2010 Digiore et al.
2011/0004075 A1 1/2011 Stahmann et al.
2011/0004278 A1 1/2011 Aghassian
2011/0022057 A1 1/2011 Eigler et al.
2011/0034874 A1 2/2011 Reitan
2011/0071336 A1 3/2011 Yomtov
2011/0137394 A1 6/2011 Lunsford et al.
2011/0144744 A1 6/2011 Wampler
2011/0152600 A1 6/2011 Scott et al.
2011/0160516 A1 6/2011 Dague
2011/0172505 A1 7/2011 Kim
2011/0184301 A1 7/2011 Holmstrom
2011/0186943 A1 8/2011 Pahl
2011/0196452 A1 8/2011 Forsell
2011/0218435 A1 9/2011 Srinivasan et al.
2011/0224720 A1 9/2011 Kassab et al.
2011/0230068 A1 9/2011 Pahl
2012/0019201 A1 1/2012 Peterson
2012/0022645 A1 1/2012 Burke
2012/0029408 A1 2/2012 Beaudin
2012/0050931 A1 3/2012 Terry et al.
2012/0068691 A1 3/2012 Ejury
2012/0084024 A1 4/2012 Norcross, Jr.
2012/0112543 A1 5/2012 van Wageningen et al.
2012/0150089 A1 6/2012 Penka et al.
2012/0150291 A1* 6/2012 Aber .................. A61M 60/873 623/3.14
2012/0158074 A1 6/2012 Hall
2012/0197141 A1 8/2012 Vanney
2012/0203476 A1 8/2012 Dam
2012/0212178 A1 8/2012 Kim
2012/0235633 A1 9/2012 Kesler et al.
2012/0245404 A1 9/2012 Smith
2012/0247200 A1 10/2012 Ahonen et al.
2012/0310037 A1 12/2012 Choi et al.
2012/0330214 A1 12/2012 Peters et al.
2013/0041204 A1 2/2013 Heilman et al.
2013/0066142 A1 3/2013 Doerr et al.
2013/0069651 A1 3/2013 Lumiani
2013/0072846 A1 3/2013 Heide et al.
2013/0099585 A1 4/2013 Von Novak et al.
2013/0116575 A1 5/2013 Mickle et al.
2013/0144379 A1 6/2013 Najafi et al.
2013/0178915 A1 7/2013 Radziemski
2013/0280692 A1 10/2013 Gourlay
2013/0289334 A1 10/2013 Badstibner
2013/0289376 A1 10/2013 Lang
2013/0303831 A1 11/2013 Evans
2013/0303970 A1 11/2013 Keenan et al.
2013/0304404 A1 11/2013 Dam
2014/0005467 A1 1/2014 Farnan et al.
2014/0012282 A1 1/2014 Fritsch
2014/0013852 A1 1/2014 Brown et al.
2014/0028107 A1 1/2014 Kwon
2014/0030122 A1 1/2014 Ozaki
2014/0039587 A1 2/2014 Romero
2014/0063666 A1 3/2014 Kallal et al.
2014/0094645 A1 4/2014 Lafontaine et al.
2014/0100414 A1 4/2014 Tamez et al.
2014/0104898 A1 4/2014 Yeo et al.
2014/0107754 A1 4/2014 Fuhs et al.
2014/0114202 A1 4/2014 Hein et al.
2014/0135884 A1 5/2014 Tockman et al.
2014/0194058 A1 7/2014 Lee et al.
2014/0200389 A1 7/2014 Yanai et al.
2014/0233184 A1 8/2014 Thompson et al.
2014/0243688 A1 8/2014 Caron et al.
2014/0249603 A1 9/2014 Yan et al.
2014/0265620 A1 9/2014 Hoarau et al.
2014/0275720 A1 9/2014 Ferrari
2014/0275727 A1 9/2014 Bonde
2014/0296677 A1 10/2014 McEowen
2014/0303426 A1 10/2014 Kerkhoffs et al.

(56) References Cited

U.S. PATENT DOCUMENTS

2014/0309733 A1 10/2014 Cotter
2014/0342203 A1 11/2014 Elian
2014/0346884 A1 11/2014 Fujita
2015/0008755 A1 1/2015 Sone
2015/0027224 A1 1/2015 Schiffer
2015/0028805 A1 1/2015 Dearden et al.
2015/0080743 A1 3/2015 Siess
2015/0090372 A1 4/2015 Branagan et al.
2015/0141832 A1 5/2015 Yu et al.
2015/0141842 A1 5/2015 Spanier et al.
2015/0157216 A1 6/2015 Stigall et al.
2015/0174307 A1 6/2015 Eckman et al.
2015/0190092 A1 7/2015 Mori
2015/0196076 A1* 7/2015 Billingslea ........... A41D 27/205 2/114
2015/0200562 A1* 7/2015 Kilinc ..................... H02J 50/10 320/108
2015/0201900 A1 7/2015 Syed
2015/0244166 A1 8/2015 Chen
2015/0250935 A1 9/2015 Anderson et al.
2015/0273184 A1 10/2015 Scott et al.
2015/0290372 A1 10/2015 Muller et al.
2015/0290373 A1 10/2015 Rudser et al.
2015/0306290 A1 10/2015 Rosenberg et al.
2015/0306291 A1 10/2015 Bonde et al.
2015/0307344 A1 10/2015 Ernst
2015/0327921 A1 11/2015 Govari
2015/0333532 A1 11/2015 Han et al.
2015/0335804 A1 11/2015 Marseille et al.
2015/0365738 A1 12/2015 Purvis et al.
2015/0374892 A1 12/2015 Yanai et al.
2015/0380972 A1 12/2015 Fort
2016/0000983 A1 1/2016 Mohl et al.
2016/0008531 A1 1/2016 Wang et al.
2016/0022889 A1 1/2016 Bluvshtein et al.
2016/0022890 A1 1/2016 Schwammenthal et al.
2016/0045165 A1 2/2016 Braido et al.
2016/0067395 A1 3/2016 Jimenez et al.
2016/0081680 A1 3/2016 Taylor
2016/0087558 A1 3/2016 Yamamoto
2016/0095968 A1 4/2016 Rudser
2016/0144166 A1 5/2016 Decré et al.
2016/0151553 A1 6/2016 Bonde
2016/0166747 A1 6/2016 Frazier et al.
2016/0175501 A1 6/2016 Schuermann
2016/0213828 A1 7/2016 Sievers
2016/0226296 A1 8/2016 Bae
2016/0254704 A1 9/2016 Hansen et al.
2016/0268846 A1 9/2016 Akuzawa et al.
2016/0271309 A1 9/2016 Throckmorton et al.
2016/0278856 A1 9/2016 Panescu
2016/0302672 A1 10/2016 Kuri
2016/0303299 A1 10/2016 Muller
2016/0317043 A1 11/2016 Campo
2016/0331980 A1 11/2016 Strommer et al.
2016/0336811 A1 11/2016 Liu
2016/0338629 A1 11/2016 Doerr
2016/0344302 A1 11/2016 Noue
2017/0010144 A1 1/2017 Lenner et al.
2017/0018967 A1 1/2017 Berkhout
2017/0021070 A1 1/2017 Petersen
2017/0043170 A1 2/2017 Guardiani
2017/0047781 A1 2/2017 Stanislawski et al.
2017/0049945 A1 2/2017 Halvorsen et al.
2017/0070082 A1 3/2017 Zheng et al.
2017/0086780 A1 3/2017 Sokulin et al.
2017/0087286 A1 3/2017 Spanier et al.
2017/0098491 A1 4/2017 Ziaie et al.
2017/0128646 A1 5/2017 Karch
2017/0136164 A1 5/2017 Yeatts
2017/0143977 A1 5/2017 Kaib et al.
2017/0202575 A1 7/2017 Stanfield et al.
2017/0203104 A1 7/2017 Nageri et al.
2017/0224279 A1 8/2017 Cahan et al.
2017/0231717 A1 8/2017 Forsell
2017/0239407 A1 8/2017 Hayward
2017/0258980 A1 9/2017 Katsuki et al.
2017/0258981 A1 9/2017 Franano
2017/0271919 A1 9/2017 Von Novak, III et al.
2017/0275799 A1 9/2017 Chen
2017/0288448 A1 10/2017 Kranz et al.
2017/0303375 A1 10/2017 Woodhead
2017/0340789 A1 11/2017 Bonde et al.
2017/0347229 A1 11/2017 Kwon
2017/0348470 A1 12/2017 D'Ambrosio et al.
2017/0353053 A1 12/2017 Muratov
2017/0354812 A1 12/2017 Callaghan et al.
2017/0361115 A1 12/2017 Aghassian
2017/0361117 A1 12/2017 Aghassian
2018/0021497 A1 1/2018 Nunez
2018/0064860 A1 3/2018 Nunez et al.
2018/0078159 A1 3/2018 Edelman et al.
2018/0078329 A1 3/2018 Hansen et al.
2018/0093070 A1 4/2018 Cottone
2018/0110910 A1 4/2018 Rodemerk et al.
2018/0126053 A1* 5/2018 Zilbershlag ......... A61M 60/216
2018/0154058 A1 6/2018 Menon et al.
2018/0194236 A1 7/2018 Elshaer et al.
2018/0199635 A1 7/2018 Longinotti-Buitoni et al.
2018/0207336 A1 7/2018 Solem
2018/0256796 A1 9/2018 Hansen
2018/0256797 A1 9/2018 Schenck et al.
2018/0256800 A1 9/2018 Conyers et al.
2018/0264182 A1 9/2018 Spanier et al.
2018/0269724 A1 9/2018 Smith
2018/0269930 A1 9/2018 Kwon
2018/0278099 A1 9/2018 Hong
2018/0280598 A1 10/2018 Curran et al.
2018/0280708 A1 10/2018 Escalona et al.
2018/0287405 A1 10/2018 Govindaraj
2018/0316209 A1 11/2018 Gliner
2018/0318483 A1 11/2018 Dague et al.
2018/0326131 A1 11/2018 Muller et al.
2018/0333059 A1 11/2018 Casas
2018/0353667 A1 12/2018 Moyer et al.
2019/0004037 A1 1/2019 Zhang et al.
2019/0046702 A1 2/2019 Siess et al.
2019/0054223 A1 2/2019 Frazier et al.
2019/0060543 A1 2/2019 Khanal et al.
2019/0068004 A1 2/2019 Louis
2019/0074726 A1 3/2019 Hosotani
2019/0083690 A1 3/2019 Siess et al.
2019/0097447 A1 3/2019 Partovi
2019/0120905 A1 4/2019 Wong
2019/0175808 A1 6/2019 Zilbershlag et al.
2019/0217002 A1 7/2019 Urakabe
2019/0222064 A1 7/2019 Du et al.
2019/0231523 A1 8/2019 Lombardi
2019/0240680 A1 8/2019 Hayakawa
2019/0254543 A1 8/2019 Hartholt et al.
2019/0267913 A1 8/2019 Lim
2019/0282741 A1 9/2019 Franano et al.
2019/0282744 A1 9/2019 D'Ambrosio et al.
2019/0305613 A1 10/2019 Oshima
2019/0321529 A1 10/2019 Korakianitis et al.
2019/0344000 A1 11/2019 Kushwaha et al.
2019/0351117 A1 11/2019 Cambronne et al.
2019/0351118 A1 11/2019 Graichen et al.
2019/0351120 A1 11/2019 Kushwaha et al.
2019/0393735 A1 12/2019 Lee et al.
2020/0016309 A1 1/2020 Kallenbach et al.
2020/0022811 A1 1/2020 Griswold
2020/0023109 A1 1/2020 Epple
2020/0028376 A1* 1/2020 Ha .......................... H02J 7/342
2020/0030509 A1 1/2020 Siess et al.
2020/0038567 A1 2/2020 Siess et al.
2020/0054806 A1 2/2020 Sun
2020/0136421 A1 4/2020 Kim
2020/0139032 A1 5/2020 Bryson et al.
2020/0147283 A1 5/2020 Tanner et al.
2020/0164125 A1 5/2020 Muller et al.
2020/0164126 A1 5/2020 Muller
2020/0227954 A1 7/2020 Ding et al.
2020/0253583 A1 8/2020 Brisken et al.

(56) References Cited

U.S. PATENT DOCUMENTS

| | | | |
|---|---|---|---|
| 2020/0366121 | A1 | 11/2020 | Guedon |
| 2020/0373768 | A1 | 11/2020 | Danilovic |
| 2021/0052793 | A1 | 2/2021 | Struthers et al. |
| 2021/0057804 | A1 | 2/2021 | Wenning |
| 2021/0143688 | A1 | 5/2021 | Agrawal et al. |
| 2021/0268264 | A1 | 9/2021 | Stotz |
| 2021/0290087 | A1 | 9/2021 | Schlebusch |
| 2021/0290929 | A1 | 9/2021 | Stotz |
| 2021/0290930 | A1 | 9/2021 | Kasel |
| 2021/0290931 | A1 | 9/2021 | Baumbach |
| 2021/0290933 | A1 | 9/2021 | Stotz |
| 2021/0298653 | A1 | 9/2021 | Woodard |
| 2021/0316133 | A1 | 10/2021 | Kassel et al. |
| 2021/0322011 | A1 | 10/2021 | Schuelke et al. |
| 2021/0336484 | A1 | 10/2021 | Araujo et al. |
| 2021/0339002 | A1 | 11/2021 | Schlebusch et al. |
| 2021/0339004 | A1 | 11/2021 | Schlebusch et al. |
| 2021/0339009 | A1 | 11/2021 | Stotz et al. |
| 2021/0346674 | A1 | 11/2021 | Baumbach et al. |
| 2021/0346675 | A1 | 11/2021 | Schlebusch et al. |
| 2021/0346676 | A1 | 11/2021 | Schlebusch et al. |
| 2021/0346677 | A1 | 11/2021 | Baumbach et al. |
| 2021/0346678 | A1 | 11/2021 | Baumbach et al. |
| 2021/0351628 | A1 | 11/2021 | Araujo et al. |
| 2021/0378523 | A1 | 12/2021 | Budde |
| 2021/0379359 | A1 | 12/2021 | Schellenberg |
| 2021/0379360 | A1 | 12/2021 | Schellenberg |
| 2021/0386990 | A1 | 12/2021 | Stotz et al. |
| 2021/0393944 | A1 | 12/2021 | Wenning |
| 2021/0399582 | A1 | 12/2021 | Araujo et al. |
| 2022/0016411 | A1 | 1/2022 | Winterwerber |
| 2022/0032032 | A1 | 2/2022 | Schlebusch et al. |
| 2022/0032036 | A1 | 2/2022 | Baumbach et al. |
| 2022/0039669 | A1 | 2/2022 | Schlebusch et al. |
| 2022/0047173 | A1 | 2/2022 | Stotz et al. |
| 2022/0050037 | A1 | 2/2022 | Stotz et al. |
| 2022/0072298 | A1 | 3/2022 | Spanier et al. |
| 2022/0079457 | A1 | 3/2022 | Tuval et al. |
| 2022/0080184 | A1 | 3/2022 | Clifton et al. |
| 2022/0080185 | A1 | 3/2022 | Clifton et al. |
| 2022/0103023 | A1 | 3/2022 | Govindaraj |
| 2022/0105339 | A1 | 4/2022 | Nix et al. |
| 2022/0126086 | A1 | 4/2022 | Schlebusch et al. |
| 2022/0139614 | A1 | 5/2022 | Diekhans et al. |
| 2022/0142462 | A1 | 5/2022 | Douk et al. |
| 2022/0161019 | A1 | 5/2022 | Mitze et al. |
| 2022/0161021 | A1 | 5/2022 | Mitze et al. |
| 2022/0166253 | A1 | 5/2022 | Forsell |
| 2022/0320901 | A1 | 10/2022 | Araujo et al. |
| 2022/0361762 | A1 | 11/2022 | Lalancette |
| 2022/0417673 | A1 | 12/2022 | Narampanawe |
| 2023/0091199 | A1 | 3/2023 | Siess et al. |
| 2023/0145482 | A1 | 5/2023 | Garrigue |
| 2023/0258694 | A1 | 8/2023 | Vijayakumar |
| 2023/0381526 | A1 | 11/2023 | Stotz et al. |
| 2024/0011808 | A1 | 1/2024 | Winzer et al. |
| 2024/0074828 | A1 | 3/2024 | Wenning |
| 2024/0186828 | A1 | 6/2024 | Chu |
| 2024/0245902 | A1 | 7/2024 | Schlebusch et al. |
| 2024/0269459 | A1 | 8/2024 | Schellenberg et al. |
| 2024/0312433 | A1 | 9/2024 | Kim |
| 2025/0032773 | A1 | 1/2025 | Baumbach et al. |
| 2025/0121177 | A1 | 4/2025 | West |
| 2025/0134652 | A1 | 5/2025 | Maiorano |
| 2025/0143587 | A1 | 5/2025 | Stotz |
| 2025/0144397 | A1 | 5/2025 | Kassel et al. |
| 2025/0222247 | A1 | 7/2025 | Schlebusch |
| 2025/0235687 | A1 | 7/2025 | Schlebusch et al. |
| 2025/0251330 | A1 | 8/2025 | Stotz |
| 2025/0281060 | A1 | 9/2025 | Schlebusch et al. |
| 2025/0319299 | A1 | 10/2025 | Stotz et al. |
| 2025/0345590 | A1 | 11/2025 | Schlebusch et al. |
| 2025/0367429 | A1 | 12/2025 | Eggen et al. |
| 2025/0367431 | A1 | 12/2025 | Baumbach et al. |
| 2026/0048254 | A1 | 2/2026 | Scheffler et al. |
| 2026/0060557 | A1 | 3/2026 | Schlebusch et al. |
| 2026/0069857 | A1 | 3/2026 | Kassel et al. |
| 2026/0083959 | A1 | 3/2026 | Baumbach et al. |

FOREIGN PATENT DOCUMENTS

| | | | | |
|---|---|---|---|---|
| CN | 1192351 A | | 9/1998 | |
| CN | 1661338 A | | 8/2005 | |
| CN | 101128168 | | 2/2008 | |
| CN | 101208045 | | 6/2008 | |
| CN | 101214158 | | 7/2008 | |
| CN | 101351237 | | 1/2009 | |
| CN | 101448535 | | 6/2009 | |
| CN | 101460094 | | 6/2009 | |
| CN | 101579233 | | 11/2009 | |
| CN | 101677812 | | 3/2010 | |
| CN | 101711683 | | 5/2010 | |
| CN | 102421372 | | 4/2012 | |
| CN | 102803923 | | 11/2012 | |
| CN | 103143072 | | 6/2013 | |
| CN | 103328018 | | 9/2013 | |
| CN | 103857326 | | 6/2014 | |
| CN | 103942511 | | 7/2014 | |
| CN | 103957957 | | 7/2014 | |
| CN | 104105449 | | 10/2014 | |
| CN | 104188687 | | 12/2014 | |
| CN | 104274873 | | 1/2015 | |
| CN | 106104229 | | 11/2016 | |
| CN | 106333707 | | 1/2017 | |
| CN | 104888293 | | 3/2017 | |
| CN | 106776441 | | 5/2017 | |
| CN | 107530479 | | 1/2018 | |
| CN | 107632167 | | 1/2018 | |
| CN | 112168427 | | 1/2021 | |
| CN | 215841206 | | 2/2022 | |
| CN | 114886614 | | 8/2022 | |
| CN | 217828630 | | 11/2022 | |
| CN | 115916111 | | 4/2023 | |
| CN | 116271502 | | 6/2023 | |
| CN | 219250364 | | 6/2023 | |
| CN | 117959584 | | 5/2024 | |
| CN | 118320294 | | 7/2024 | |
| CN | 118717356 | | 10/2024 | |
| CN | 119033506 | | 11/2024 | |
| DE | 11 65 144 | | 3/1964 | |
| DE | 41 05 278 | | 8/1992 | |
| DE | 195 20 920 | | 12/1995 | |
| DE | 198 21 307 | | 10/1999 | |
| DE | 199 56 380 | | 11/1999 | |
| DE | 200 13 876 | | 9/2001 | |
| DE | 100 59 714 | | 5/2002 | |
| DE | 100 60 275 | | 6/2002 | |
| DE | 101 44 269 | | 3/2003 | |
| DE | 102 26 305 | | 10/2003 | |
| DE | 103 02 550 | | 8/2004 | |
| DE | 20 2005 020 288 | | 6/2007 | |
| DE | 10 2006 001 180 | | 9/2007 | |
| DE | 10 2008 060 357 | | 6/2010 | |
| DE | 10 2009 007 216 | | 8/2010 | |
| DE | 10 2009 011 726 | | 9/2010 | |
| DE | 10 2009 025 464 | | 1/2011 | |
| DE | 10 2009 047 845 | | 3/2011 | |
| DE | 10 2011 106 142 | | 12/2012 | |
| DE | 11 2009 000 185 | | 3/2013 | |
| DE | 10 2012 200 912 | | 7/2013 | |
| DE | 20 2011 110 389 | | 9/2013 | |
| DE | 11 2012 005 944 | | 12/2014 | |
| DE | 20 2013 007 408 | | 12/2014 | |
| DE | 10 2015 004 177 | | 10/2015 | |
| DE | 102014110457 A1 | * | 1/2016 | ........ A61M 25/0127 |
| DE | 10 2016 106 683 | | 10/2016 | |
| DE | 10 2015 219 263 | | 4/2017 | |
| DE | 10 2015 222 199 | | 5/2017 | |
| DE | 10 2016 225 862 | | 6/2017 | |
| DE | 20 2015 009 422 | | 7/2017 | |
| DE | 10 2016 203 172 | | 8/2017 | |
| DE | 10 2012 207 042 | | 9/2017 | |
| DE | 10 2016 013 334 | | 4/2018 | |
| DE | 10 2017 213 475 | | 2/2019 | |

(56) References Cited

FOREIGN PATENT DOCUMENTS

| | | |
|---|---|---|
| DE | 10 2018 204 604 | 10/2019 |
| DE | 10 2018 204 610 | 10/2019 |
| DE | 10 2018 206 714 | 11/2019 |
| DE | 10 2018 206 724 | 11/2019 |
| DE | 10 2018 206 725 | 11/2019 |
| DE | 10 2018 206 727 | 11/2019 |
| DE | 10 2018 206 731 | 11/2019 |
| DE | 10 2018 206 750 | 11/2019 |
| DE | 10 2018 206 754 | 11/2019 |
| DE | 10 2018 206 758 | 11/2019 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 764 448 | 3/1997 |
| EP | 0 794 411 | 9/1997 |
| EP | 0 904 630 | 3/1999 |
| EP | 0 916 359 | 5/1999 |
| EP | 0 930 086 | 7/1999 |
| EP | 1 062 959 | 12/2000 |
| EP | 1 339 443 | 11/2001 |
| EP | 1 011 803 | 9/2004 |
| EP | 2 143 385 | 1/2010 |
| EP | 2 175 770 | 4/2010 |
| EP | 2 314 744 | 4/2011 |
| EP | 2 129 410 | 9/2011 |
| EP | 2 187 807 | 6/2012 |
| EP | 2 570 143 | 3/2013 |
| EP | 1 827 573 | 4/2013 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 906 265 | 7/2016 |
| EP | 2 213 227 | 8/2016 |
| EP | 2 454 799 | 9/2016 |
| EP | 3 088 016 | 11/2016 |
| EP | 2 585 129 | 3/2017 |
| EP | 2 709 689 | 4/2017 |
| EP | 3 220 505 | 9/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 378 421 | 9/2018 |
| EP | 3 536 360 | 9/2019 |
| EP | 2 505 090 | 12/2019 |
| EP | 3 062 877 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 487 548 | 3/2021 |
| EP | 3 509 661 | 3/2021 |
| EP | 3 528 863 | 3/2021 |
| EP | 3 615 103 | 3/2021 |
| EP | 3 436 105 | 4/2021 |
| EP | 3 116 407 | 5/2021 |
| EP | 3 131 600 | 6/2021 |
| EP | 3 131 615 | 6/2021 |
| EP | 3 827 876 | 6/2021 |
| EP | 2 608 731 | 7/2021 |
| EP | 3 463 505 | 9/2021 |
| EP | 3 884 970 | 9/2021 |
| EP | 2 599 510 | 10/2021 |
| EP | 3 077 018 | 10/2021 |
| EP | 3 485 936 | 10/2021 |
| EP | 3 668 561 | 10/2021 |
| EP | 3 164 168 | 12/2021 |
| EP | 3 344 129 | 12/2021 |
| EP | 3 539 613 | 2/2022 |
| EP | 2 858 718 | 3/2022 |
| EP | 3 624 867 | 3/2022 |
| EP | 3 689 389 | 3/2022 |
| EP | 3 737 436 | 3/2022 |
| EP | 3 972 661 | 3/2022 |
| EP | 3 755 237 | 4/2022 |
| EP | 3 984 589 | 4/2022 |
| EP | 3 079 758 | 5/2022 |
| EP | 3 654 006 | 5/2022 |
| EP | 3 497 775 | 7/2022 |
| EP | 2 999 400 | 8/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 328 311 | 11/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 046 594 | 3/2023 |
| EP | 3 938 005 | 4/2023 |
| EP | 3 946 511 | 4/2023 |
| EP | 3 826 104 | 5/2023 |
| EP | 3 809 959 | 7/2023 |
| EP | 2 072 150 | 9/2023 |
| EP | 2 961 984 | 9/2023 |
| EP | 3 768 156 | 9/2023 |
| EP | 2 878 061 | 10/2023 |
| EP | 4 052 754 | 10/2023 |
| EP | 4 252 825 | 10/2023 |
| EP | 4 252 826 | 10/2023 |
| EP | 4 252 828 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 072 210 | 12/2023 |
| EP | 3 687 596 | 12/2023 |
| EP | 3 768 340 | 12/2023 |
| EP | 3 735 733 | 1/2024 |
| EP | 3 566 636 | 2/2024 |
| EP | 3 634 526 | 2/2024 |
| EP | 3 768 342 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 4 384 259 | 9/2024 |
| EP | 3 793 674 | 10/2024 |
| EP | 3 618 885 | 11/2024 |
| EP | 3 809 960 | 12/2024 |
| EP | 4 477 250 | 12/2024 |
| EP | 4 483 940 | 1/2025 |
| EP | 4 491 213 | 1/2025 |
| EP | 4 429 754 | 2/2025 |
| EP | 3 970 785 | 3/2025 |

(56) References Cited

FOREIGN PATENT DOCUMENTS

| | | |
|---|---|---|
| EP | 4 429 753 | 3/2025 |
| EP | 3 950 043 | 5/2025 |
| EP | 4 039 319 | 6/2025 |
| EP | 3 668 559 | 8/2025 |
| EP | 3 848 088 | 8/2025 |
| EP | 4 119 184 | 9/2025 |
| EP | 4 218 556 | 9/2025 |
| EP | 4 100 106 | 12/2025 |
| EP | 4 454 696 | 12/2025 |
| EP | 4 112 115 | 2/2026 |
| ES | 2 913 485 | 6/2022 |
| GB | 2 345 387 | 7/2000 |
| GB | 2 504 177 | 1/2014 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-178249 | 7/1999 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2003-525438 | 8/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-503495 | 2/2010 |
| JP | 2010-518907 | 6/2010 |
| JP | 4706886 | 6/2011 |
| JP | 2012-520157 | 9/2012 |
| JP | 2013-013216 | 1/2013 |
| JP | 2013-519497 | 5/2013 |
| JP | 2013-128792 | 7/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 6063151 | 1/2017 |
| JP | 2017-176719 | 10/2017 |
| JP | 2017-532084 | 11/2017 |
| JP | 2018-046708 | 3/2018 |
| JP | 2018-057878 | 4/2018 |
| JP | 2019-508128 | 3/2019 |
| JP | 2019-523110 | 8/2019 |
| JP | 2020-072985 | 5/2020 |
| JP | 2019-509141 | 2/2022 |
| KR | 10-1185112 | 9/2012 |
| RO | 131676 | 2/2017 |
| WO | WO 89/006513 | 1/1989 |
| WO | WO 92/015239 | 9/1992 |
| WO | WO 94/009835 | 5/1994 |
| WO | WO 98/043688 | 10/1998 |
| WO | WO 99/049912 | 10/1999 |
| WO | WO 00/033047 | 6/2000 |
| WO | WO 2006/122001 | 11/2006 |
| WO | WO 2008/106103 | 9/2008 |
| WO | WO 2009/023905 | 2/2009 |
| WO | WO 2009/029977 | 3/2009 |
| WO | WO 2009/073037 | 6/2009 |
| WO | WO 2010/042054 | 4/2010 |
| WO | WO 2010/142286 | 12/2010 |
| WO | WO 2010/143272 | 12/2010 |
| WO | WO 2011/007300 | 1/2011 |
| WO | WO 2012/018917 | 2/2012 |
| WO | WO 2012/112378 | 8/2012 |
| WO | WO 2012/147061 | 11/2012 |
| WO | WO 2013/120957 | 8/2013 |
| WO | WO 2013/160443 | 10/2013 |
| WO | WO 2013/164831 | 11/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2015/152732 | 10/2015 |
| WO | WO 2016/001284 | 1/2016 |
| WO | WO 2016/066180 | 5/2016 |
| WO | WO 2016/137743 | 9/2016 |
| WO | WO 2017/021846 | 2/2017 |
| WO | WO 2017/032751 | 3/2017 |
| WO | WO 2017/040218 | 3/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/147291 | 8/2017 |
| WO | WO 2017/165372 | 9/2017 |
| WO | WO 2017/205909 | 12/2017 |
| WO | WO 2017/213032 | 12/2017 |
| WO | WO 2017/214118 | 12/2017 |
| WO | WO 2017/218349 | 12/2017 |
| WO | WO 2018/005228 | 1/2018 |
| WO | WO 2018/033799 | 2/2018 |
| WO | WO 2018/036927 | 3/2018 |
| WO | WO 2018/039479 | 3/2018 |
| WO | WO 2018/048800 | 3/2018 |
| WO | WO 2018/078615 | 5/2018 |
| WO | WO 2018/100192 | 6/2018 |
| WO | WO 2018/109038 | 6/2018 |
| WO | WO 2018/146045 | 8/2018 |
| WO | WO 2018/213089 | 11/2018 |
| WO | WO 2019/025258 | 2/2019 |
| WO | WO 2019/025259 | 2/2019 |
| WO | WO 2019/025260 | 2/2019 |
| WO | WO 2019/034670 | 2/2019 |
| WO | WO 2019/078723 | 4/2019 |
| WO | WO 2019/101786 | 5/2019 |
| WO | WO 2019/118371 | 6/2019 |
| WO | WO 2019/126721 | 6/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/219883 | 11/2019 |
| WO | WO 2019/229210 | 12/2019 |
| WO | WO 2019/229220 | 12/2019 |

(56) References Cited

FOREIGN PATENT DOCUMENTS

| | | |
|---|---|---|
| WO | WO 2019/229221 | 12/2019 |
| WO | WO 2019/229222 | 12/2019 |
| WO | WO 2019/229224 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/241556 | 12/2019 |
| WO | WO 2019/243582 | 12/2019 |
| WO | WO 2019/244031 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/243756 | 12/2020 |
| WO | WO 2021/159001 | 8/2021 |
| WO | WO 2023/040546 | 12/2021 |
| WO | WO 2022/074136 | 4/2022 |
| WO | WO 2022/109590 | 5/2022 |
| WO | WO 2022/173970 | 8/2022 |
| WO | WO 2022/174249 | 8/2022 |
| WO | WO 2023/226779 | 9/2022 |
| WO | WO 2023/037162 | 3/2023 |
| WO | WO 2023/049813 | 3/2023 |
| WO | WO 2023/076869 | 5/2023 |
| WO | WO 2023/112044 | 6/2023 |
| WO | WO 2023/230157 | 11/2023 |
| WO | WO 2024/104184 | 5/2024 |
| WO | WO 2026/072583 | 4/2026 |

OTHER PUBLICATIONS

"ECG Electrodes product comparison chart," 3M.com, https://multimedia.3m.com/mws/media/1490883O/red-dot-ecg-electrodes-comparison-chart.pdf, accessed May 18, 2025 (Year: 2018).*

Robin Mack-Haynes, "Fasteners Made Easy," New Mexico State University, https://pubs.nmsu.edu/_c/C232.pdf, accessed May 18, 2025 (Year: 2019).*

Hertz Ph.D. et al, "Ultrasonic Engineering in Heart Diagnosis", The American Journal of Cardiology, Jan. 1967, vol. 19, No. 1, pp. 6-17.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Eeckhout, MD, PhD, et al., "Handbook of Complications During Percutaneous Cardiovascular Interventions", 2007 Informa UK Ltd., Ch. 12, pp. 167-177.

HeartMate 3™ Left Ventricular Assist System, Instructions for Use, Thoratec Corporation, Aug. 2017, pp. 536. [Uploaded in 3 parts].

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Mullins, Charles E., MD, "Cardiac Catheterization in Congenital Heart Disease: Pediatric and Adult", Blackwell Futura, 2006, Chapters 3, 4 and 32, pp. 101.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRH0=&i=1&b=0&modal=1, accessed Sep. 2, 2025, 1 page.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Tan et al., "Surface Engineering and Patterning Using Parylene for Biological Applications." Materials, Mar. 15, 2010, vol. 3, No. 3, pp. 1803-1832.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Walser, Eric, "Venous access ports: indications, implantation technique, follow-up, and complications;" Cardiovasc Intervent Radial, Aug. 2012; vol. 35, No. 4, pp. 751-764. (Abstract Only).

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

* cited by examiner

TRANSCUTANEOUS ENERGY TRANSFER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The disclosure relates to a device for the transcutaneous transfer of energy into a human body and method for transferring energy into a human body.

Description of the Related Art

Current heart support systems, or ventricular assist devices (VAD), consist of intracorporeal components, for example a pump, and extracorporeal elements, a control unit, and batteries. The intracorporeal and extracorporeal components may be connected by a cable through the skin, the so-called driveline so that energy may be transferred to the intracorporeal components.

SUMMARY

This application concerns a device for transcutaneous transfer of energy into a human body, and a method for transferring energy into a human body to power a VAD. However, the systems and embodiments described herein can be used to power any intracorporeal medical device. The disclosure provides an improved human-machine interface for medical devices with transcutaneous energy transfer (TET), such as a VAD or an implanted cardiac support system. The device is ergonomic and easy to use. Use of the device can reduce the risk of operating errors and damage to the patient. It may also accelerate the healing process and make other processes, both in everyday patient life and in hospitals, more efficient. Further, in time-critical surgery situations the device can save valuable seconds.

A device for transcutaneous transmission of energy into a human body is described herein. The device may comprise an extracorporeally arranged or arrangeable transmission device with induction charging coil and a sensor device. The induction charging coil is adapted to provide a magnetic field for transferring energy to an induction coil arranged intracorporeally, and the sensor means is adapted to determine a relative position between the induction charging coil and the induction coil. The device may be used to power medical devices. For example, the device may be used in patients with heart failure who use a VAD, such as a heart pump. In such cases, the extracorporeal induction charging coil and the magnetic field wirelessly generate a current in the intracorporeal induction coil, which in turn powers the cardiac support system. In some embodiments, transcutaneous energy transfer may be employed to charge an intracorporeal battery. Advantageously, there is no need for partially rigid cable connections, reducing the risk of infection or injury and increasing the patient's everyday ease-of-use of the cardiac support system.

For optimal transcutaneous energy transfer, alignment of the extracorporeal induction charging coil and the intracorporeal induction coil is important. To establish a current flow, the induction charging coil may be placed on the body and positioned as congruently as possible over the intracorporeal coil. The device may include a sensor configured to detect the relative position between the induction charging coil and the induction coil. During the inductive transmission of electrical energy, the sensor allows the device to determine the relative alignment between the transmitting and receiving inductions coils without using mechanical guides or extensive measuring. Thus, the device can ensure optimal alignment of intra- and extracorporeal induction coils with each other. The device may also be configured to assist a patient or medical staff in the alignment of the induction charging coil.

According to some embodiments, the sensor may include at least one Hall sensor for detecting the position of the extracorporeal induction coil relative to the intracorporeal induction coil. For example, a linear Hall sensor can be placed in the center of the extracorporeal induction charging coil. The Hall sensor may be comprised of a ground connection, supply voltage, and an output. The Hall sensor may be connected to a microcontroller with AC/DC conversion. The supply voltage may be connected to the operating voltage of the microcontroller. The output may be connected to a pin with AC/DC conversion. A small permanent magnet may also be inserted in the center of the intracorporeal induction coil. When the extracorporeal induction charging coil approaches the intracorporeal induction coil, the Hall sensor may be brought into the magnetic field of the permanent magnet. As a result, the voltage at the output of the Hall sensor may increase or decrease, depending on the polarity of the magnetic field. A zero value can be determined during a calibration process where the Hall sensor output is averaged over a short period of time when no magnet is near the device. The maximum deviation from zero value, or maximum output, can be determined by placing the Hall sensor in direct contract with the permanent magnet. Using the output of the Hall sensor, a precise distance between the extracorporeal induction coil and the intracorporeal induction coil can be determined.

According to some embodiments, the sensor may have three Hall sensors. The three Hall sensors may be arranged in a triangle relative to one another in the middle of the extracorporeal induction charging coil. The three sensors may be configured to determine the exact direction of the spatial deviation between the device and the induction coil. For example, if the device approaches the induction coil from one side, the deviation from the zero value for a first Hall sensor may change at a faster rate than the remaining sensors. On the other hand, if the device is approached from above, the measured values of all three sensors may change evenly. Thus, it can be determined whether the permanent magnet of the intracorporeal induction coil is correctly positioned left-to-right and whether the distance between the components is correct. By using more than one Hall sensor, the offset voltage caused by environmental factors can be suppressed, e.g. via spatial spinning current operation.

Additionally, a fourth Hall sensor may be used to determine the exact position of the device relative to the induction coil, specifically whether the device is oriented or rotated in the correctly. This fourth Hall sensor may be placed centrally between the other three Hall sensors. A bar magnet may also be inserted in the center of the intracorporeal induction coil. Because the bar magnet has a north and a south pole, the relative orientation of the device and the induction coil can be determined. The Hall sensors closer to the North Pole may output a value less than Vcc/2, i.e. less than half the supply voltage of the sensors. The fourth Hall sensor can be used to detect the center of the induction coil by placing the Hall sensor in the center of the bar magnet, causing the fourth Hall sensor to output exactly Vcc/2. Accordingly, the device can be ideally aligned over the induction coil if the fourth Hall sensor measures Vcc/2; at least one of the other Hall sensors measures a value less than Vcc/2; and at least one other Hall sensor measures a value greater than Vcc/2. Since the intracorporeal induction coil should not rotate in the body, the sensor may accurately determine the position of the relative position of the intra- and extracorporeal components regardless of the position that the patient is placed in.

According to some embodiments, a software calibration procedure may be performed. During the calibration procedure, the patient or a physician may be instructed or prompted to move the extracorporeal device first exactly downwards, then exactly right, move it exactly up and exactly to the left. Measurements of each of the Hall sensors may be recorded during each movement. This data can be used, for example, as a reference for future displays of the alignment direction.

According to another design, the sensor device can have a gyroscopic sensor for sensing a spatial position of the device. The gyroscopic sensor may provide a spatial signal representing the spatial position of the components of the device. For example, the sensor device may have three Hall sensors arranged in a triangle, and the gyroscopic sensor may be disposed in the center of the triangle. In some embodiments, the device may be positioned while the patient is upright, e.g., in a sitting or standing position. During the positioning process, the gyroscopic sensor can be calibrated by identifying the direction of gravity, i.e. measuring an acceleration of about 9.81 m/s^2. Thus, the position of the device in space and the corresponding alignment of the induction charging coil relative to the induction coil can be indirectly detected.

In addition, the apparatus may also include control apparatus, which may also be referred to as a control unit, for controlling an operation of the induction charging coil using the position signal. The control apparatus may include a non-transitory memory and a processor to execute the functions of the control unit. The position signal may, for example, be used to control a position of the extracorporeal induction charging coil using several sensors of the sensor device represents the relative position detected between the device and the intracorporeal induction coil. As discussed below, the control apparatus may comprise a variety of components that may be positioned intra- or extracorporeally. The control apparatus may be disposed extracorporeally or intracorporeally. Some embodiments may include more than one control unit. For example, an extracorporeal electronic control unit (eECU) may be configured to establish communication with an intracorporeal control unit, which may also be referred to as an intracorporeal electronic controller (iECU), from outside the body. In some embodiments, the device may include the eECU and/or the iECU. The functions of the eECU and control unit are described below. However, the iECU may also be configured to perform the same functions, individually or with the eECU.

The eECU may be configured to control the power supply of the intracorporeal system by means of inductive charging. The power supply may be comprised of one or more rechargeable batteries, also known as extracorporeal batteries (eBAT), which may be connected to the control apparatus and the induction charging coil. Using the position signal, an eECU may initiate or control the charging process for charging an intracorporal energy storage device of a cardiac support system. In addition, the eECU may collect and process technical data of the cardiac support system like positional or system data as well as the patient's vitals. In some embodiments, sensors may be disposed within components of the intracorporeal cardiac support system, for example a flowrate sensor may be arranged in or near a heart pump. The sensors may be designed to record technical data, such as energy consumption and the speed of the pump, and to transmit the collected data to the eECU.

According to some embodiments, the eECU may be configured to provide the collected data to a remote computing environment, such as a cloud network. The eECU may be connected to the remote computer environment via a network such as a wireless network, personal area network, mobile network, or the like. The eECU may also be configured as an interface between different components of the device. For example, the eECU may manage internal components of the device, e.g., a VAD system, as well as external components, such as one or more sensors, a battery, or one or more positioning devices, as well as any communication between components.

In addition, the control apparatus may provide a user with direct feedback for alarms or information about the cardiac support system. According to another design, the device may include a display means for displaying information. The display means may display position information based on the position signal and/or in response to the spatial signal. According to some embodiments, the display device may be adapted to display vital signs of the patient and technical data of the cardiac support system. The display device may also provide a clear presentation of system information such as battery status, pump status, connection status, alarm history and active alarms. Advantageously, a display device may quickly provide a patient or medical personnel with an easy-to-read overview of relevant data relating to the cardiac support system and the patient's health.

According to some embodiments, the display device may show a graphical display of the positional information, system information, or patient vitals. The graphical display may include a battery level indicator, an alarm indicator to indicate an alarm and/or an alarm history. The graphical display may also include a connection indicator to indicate connected devices, components, and/or connection possibilities. Further, the graphical display may include a system indicator to display system information. According to some embodiments, the control unit may receive corresponding signals regarding technical data of the cardiac support system or vital parameters of the patient from an intracorporeally arranged sensor system and generate the graphical display to be displayed by the display unit. A large amount of information may be included in the graphical display. For example, the graphical display may include information, such as body temperature, measured flow of a heart pump or blood pressure, which may be presented to a patient in an understandable manner.

In some instances, the device may include a light unit to visually display the position information. The light unit is configured to facilitate the handling of the device by providing a patient with quick, easily understandable feedback on the cardiac support system and device. In some embodiments, the light unit may be a component of the display device or the control unit. The light unit may be a polychromatic LED light that changes color depending on the relative position. For example, the LED light may shine red light, indicating that the extracorporeal induction coil is located at a distance or angle that is unfavorable for energy transfer. A green light may indicate an optimal positioning of the induction coils. In some embodiments, the light unit may be monochrome. In some embodiments, the light unit may only be activated when the device has reached a predefined minimum distance from the intracorporeal induction coil. According to some embodiments, the light unit may include an alarm function. For example, the light may be activated in case of a device malfunction or low battery.

In addition, the device may include at least one speaker unit for acoustically transmitting the position information. For example, the speaker may be included as part of the control unit. The speaker unit may be configured to emit an acoustic signal as soon as the device has reached the optimal position for power transmission. The acoustic signal may be a simple sound such as a beeping that increases in frequency as the induction coils become more aligned. In some embodiments, the signal may be verbal instructions detailing how the extracorporeal induction coil should be moved to bring it into alignment with the intracorporeal induction coil. The speaker unit may also be configured to generate an acoustic warning signal if an alarm is present, for example, if an unfavorable position change of an induction coil occurs during a charging process. The acoustic signal may allow an alarm to be perceived even when the patient is not actively monitoring the device or becomes distracted. For example, the acoustic signal can be perceived if the device is not positioned directly on the body, e.g., in a pocket, and the alert would not be perceptible visually or haptically.

In some instances, the device may include one vibration unit for haptic display of the position information. According to some embodiments, the vibration unit may be a component of the display device or otherwise disposed against the patient's body. For example, the control apparatus may include a vibration motor, which is mounted on a side of the control apparatus so that a vibration performed by the vibration unit can be transmitted to the human body. The vibration motor may also be placed on a transport or carrying system for the device. In some embodiments, the vibration motor may be placed on the skin or in clothing. The vibration unit may be positioned so that haptic signals can be perceived directly by the patient such that alarms and instructions that are not perceptible by others. The vibration unit may be configured to emit a haptic signal based on the positioning of the device. For example, the vibration unit may emit a haptic signal when the device is placed in an optimal position or when an undesired change in position occurs. The haptic signals generated by the vibration unit may be different based on the positioning of the device. For example, a first haptic signal may be generated in response to the device being placed in the optimal position, and a second haptic signal may be generated if an undesired change in position occurs. Continuing the example, the first signal may be a short, repetitive haptic signal, and the second signal may be a long vibration that continues until the device returns to the optimal position.

The device may further comprise an alarm button configured to trigger an emergency call. The alarm button may be a hardware button or a graphical menu item in the graphical display of the display unit and may be configured to call an emergency contact or emergency services. According to some embodiments, the device may comprise a microphone and a speaker to allow for communication between the patient and the call recipient. The control unit may be connected or connectable to a mobile phone network. Upon pressing the alarm button, the control unit may call a family member stored in the control unit's system and/or call the emergency services. In some embodiments, the alarm button may connect to an emergency center for the VAD system, which can forward the call for help. It is also possible that the control apparatus can be trained to notify the emergency services independently. For example, if an alarm condition of high priority exists for a period of time, the control unit may connect to the stored emergency contact, emergency services, and/or the emergency center for the VAD system and generate a recorded voice message or a text transmission describing the alarm. In some embodiments, the device may be equipped with a GNSS sensor, and the control unit may be further configured to transmit location of the patient.

The control apparatus may be detachably connected to the induction charging coil. For example, the connection can be made by a cable, and after the end of the desired use, e.g. after the end of a charging process, the two components can be separated. In such embodiments, the control apparatus may can be manufactured, stored, or replaced independently of the rest of the cardiac support system. In addition, a control apparatus that can be used externally may provide easy access to the control apparatus.

The control apparatus may be integrated into the extracorporeal transfer device. For example, one or more buttons can be arranged directly on the induction charging coil, whereby the handling of the transmission equipment can be simplified. The extracorporeal transfer device can be designed to be easily accessible so that one or more buttons or a graphical user interface can be used to control the connected components. For example, the one or more buttons may be used to mute alarms. Further, in an emergency, the patient may be found by someone who is not familiar with VAD systems. Outputs from the integrated control apparatus can help the person find the induction charging coil and place it appropriately.

The control apparatus may be arranged in a waterproof and/or dustproof housing. For example, the housing can be designed according to the IP protection class IP55 dustproof and jet-proof. In some embodiments, the housing maybe designed according to IP57 dust protected and protected against temporary immersion. The housing may be manufactured by casting the housing with an epoxy resin or by using a sealant and suitable switches and plug boxes. In some instances, the control apparatus can be protected, especially in case of contact with sweat or water.

The cardiac support system may further comprise a positioning apparatus configured for positioning an extracorporeal induction coil of a cardiac support system on a body. In some embodiments, the positioning apparatus may also retain extracorporeal components of the cardiac support system. The positioning apparatus may include a receiving element for receiving the induction coil, a connecting line for connecting the receiving element and/or the induction coil to at least one extracorporeal component of the cardiac support system, and/or a carrying device and/or a supporting device for carrying the extracorporeal component of the cardiac support system. The receiving element may be detachably connectable to the body and/or a supporting device. The support device, in some instances, may comprise at least one connecting element for releasably connecting the component to the support device.

A correct alignment between the intra- and extracorporeal coils with a displacement of max. 20 mm is important to supply the intracorporal system with sufficient current. In some embodiments, the extracorporeal induction coil may be fastened to the receiving element, which may also be referred to as a mounting element, of the positioning device. The receiving element may be positioned at the optimal position on the body for an energy transfer or charging process. The ergonomic and reliable fastening of the receiving element may provide for increased safety and only slight slipping even when the patient moves, which makes the cardiac support system more efficient and able to transmit greater power. The mounting element may be glued directly onto the patient's skin or connected to the positioning apparatus. The supporting element may include a textile layer such as a vest or a belt system. By means of the textile layer, the receiving element and the induction coil located therein can be connected to other extracorporeal components of the cardiac support system.

The extracorporeal components may include a control apparatus or an energy source, such as a battery. The extracorporeal components may be electrically connected to the receiving element. This connection may be facilitated by such as an electrical conduit or guiding fabric channel in the textile layer that guides wiring between components, for example. In some embodiments, the textile layer may include wiring to connect to the components. During the charging process, the connecting line can allow all the required extracorporeal components to be positioned close to the extracorporeal induction coil while allowing the patient extensive freedom of movement. The components of the positioning apparatus may be connected a supporting element and/or holder. For example, the supporting element may be a holster or vest configured to receive the extracorporeal components of the VAD such as a control unit or the battery. The extracorporeal components may be attached to the supporting element with removable clips, Hook-and-loop fasteners, and associated cable management system.

The receiving element may be releasably connected to the induction coil. According to some embodiments, the receiving element can be formed as a ring and may be comprised of a relatively strong, semi-flexible material. The receiving element may include a raised bead in its surface configured to grip the induction coil a corresponding an undercut in the induction coil when the coil is inserted into the receiving element. According to some embodiments, the receiving element may be comprised of a snap-fit assembly. The snap-fit assembly may be comprised of two members. A first member may be mounted to the patient and optimally positioned relative to an intracorporeal induction coil. The second member may be configured to receive the extracorporeal induction coil. For example, the extracorporeal induction coil may snap into the second member of the snap-fit assembly. According to some embodiments, the snap-fit assembly may be an annular snap-fit assembly. The first member may be ring-shaped and configured to receive the second member concentrically inside of the first member.

The snap-fit assembly allows the induction coil to be easily separated from the receiving element, whereby no residues, for example of an adhesive, remain on the induction coil. Both the induction coil and the receiving element can thus be replaced independently of each other, saving costs and material. In addition, the receiving element can remain on the carrying device, for example, while the induction coil is exchanged or removed. For example, this may advantageously help to protect the coil from water during showering. In such embodiments, the receiving element can remain on the body to avoid skin irritation. In some instances, once the optimal position of the extracorporeal induction coil on the body has been determined, the coil can then be placed in the receiving element quickly and precisely.

According to some embodiments, the receiving element may be comprised of a hook-and-loop fastener, another snap-fit design, or a magnetic clasp. For example, the supporting element can be designed as a vest or shirt, which can, for example, enclose the patient's chest and back. The inside of the supporting element may be comprised of a soft, hook-and-loop material disposed in four defined areas. Accordingly, the receiving element can have hook-and-loop material on a side facing away from the induction coil. The receiving element can then be positioned on one of the hook-and-loop clad areas of the support device and fixed by means of a hook-and-loop fastener. Other means, such as the snap-fit assembly or the magnetic clasp may be similarly utilized.

The receiving element may be designed as part of a positioning patch. For example, the positioning patch can be positioned on the body by means of an adhesive. In some instances, the positioning patch may include a multi-layer structure. For example, the receiving element can be arranged on a carrier layer via a connecting film, such as an adhesive film. The carrier layer can be designed to adapt to different positions and body curvatures. In some embodiments, the carrier layer may be comprised of be made of a very soft and flexible material, which enables it to compensate for different curvatures between the carrier layer and the receiving element. An adhesive may be applied to one side of the carrier layer for adhesion to the patient's skin. The positioning patch may be produced as a low-cost disposable article due to its low-complexity form. The positioning patch may also be configured to be disposable or sterilizable.

The positioning patch, in some instances, may also include an at least partially folded protective film to protect the adhesive. The protective film may be comprised of a thin, smooth, and flexible material and may be formed in one part or in two parts (e.g., double-folded). The folded protective film may prevent the adhesive from drying out and allow the positioning patch to be moved on the body. In some instances, the positioning patch may be allowed to be continuously placed until the optimal charging position for the extracorporeal induction coil is located. After the induction coil has been optimally positioned, the protective film may be removed from the adhesive. For example, the protective film may be pulled away from the adhesive by two tabs. After the protective foil has been pulled off, the adhesive of the positioning patch can be adhered to the body, and the extracorporeal induction coil can be fixed in the optimal charging position.

The supporting element may be comprised of a textile layer. The cable connecting the extracorporeal induction coil to the cardiac support system may be guided or guided along the textile layer. For example, the textile layer may enclose the entire upper body of the patient in the form of a vest, whereby easy dressing and undressing can be realized, for example, by means of a zipper at the front or buttons. In some instances, the positioning apparatus may be designed as a belt system that can be flexibly positioned on the patient's upper body. The cable connecting the extracorporeal induction coil and the cardiac support system may be routed along a surface of the carrying device or be integrated into the structure of the textile layer. The connecting cable may be a fixed shape such that more freedom of movement can be achieved by the patient while wearing the positioning apparatus, increasing patient comfort and protecting the VAD system components.

The positioning apparatus may further comprise a connecting element configured to join the components of the positioning apparatus and/or the extracorporeal components of the cardiac support system. In some embodiments, the connecting element may comprise a groove for inserting a retaining element. For example, the connecting element, which may contain the control apparatus, can be attached onto another component, such as a battery, or the supporting element via a vertical tongue and groove construction. A mechanical spring mechanism may be attached to the tongue and can first be pushed back by the insertion of the tongue into the groove and then return to lock the tongue in a final position in the groove. To unhook the components, an outwardly accessible release button may be pressed. The components may be connected vertically or laterally, and the connection may be secured by additional features, such as a magnet. For example, a horizontal tongue and groove construction can be used, which can have an open profile at defined points in order to insert the fastener. The connecting element can be pushed laterally up to a stop and held in place by a magnet. The magnetic force may be configured to prevent accidental pushing back while allowing people to release the components with relatively little force.

The connecting element may be shaped as an eyelet for hooking the retaining element. For example, an eyelet can be attached to a carrying device designed as a vest or holster. The carrying device may be made of a tear-resistant and flexible textile. The components of the positioning apparatus and the extracorporeal components of the cardiac support system, such as a battery or a control unit, may include a ladder buckle with a hook, which can be hooked into the eyelet. In some instances, a component may be placed in a bag or pocket configured to attach to the eyelet. The component may be detachable from the rest of the positioning system. For example, the patient may use a familiar and easy-to-use buckle system.

The connecting element may include at least one electrical contact element for establishing an electrical contact between the component and the connecting line. For example, the connecting line can be electrically conductive and electrically connected to the component by means of the contact element. The electrical contacts may be spring-activated to compensate for tolerances and ensure constant pressure and contact with the opposite side. The contact element and connecting cable may be configured to allow current and signals to flow between the component, for example a control unit or battery and the receiving element, in which the induction coil for charging the cardiac support system can be located.

The positioning apparatus may further comprise a holding element for detachable connection of the component to the support device. The holding element can be located, for example, on a pocket for holding the component or on the component itself. This allows an extracorporeal component to be connected to or disconnected from the carrying device as needed, increasing the comfort of the positioning device for a patient.

The positioning apparatus may comprise a cable holder configured to guide a cable. The cable holder may be used to fix the connecting cable that leads from the component to the mounting element in the ready-for-operation state, i.e. the optimal position for charging. The cable holder may be configured to safely store cables used during a charging or energy transfer process, thus providing the patient with the greatest possible freedom of movement is made possible.

The positioning apparatus may include at least one strap to fix the carrying device to the body and additionally or alternatively at least one pocket to hold extracorporeal components. For example, the carrying device can be designed as a shirt and include two adjustable rubber straps. The rubber straps may be stretched over the patient's shoulders and cross over the patient's back. From the patient's back, the rubber straps can be led back to the front and fastened at the bottom of the positioning apparatus, for example, with hook-and-loop fasteners. The straps can be used to secure the carrying device and prevent the unwanted movement of the positioning apparatus, external components of the cardiac support system, or the extracorporeal induction coil. The positioning apparatus can be adapted to different body shapes. The carrying device may be expanded by means of pockets integrated into the carrying device for stowing the extracorporeal components. The pockets may be configured so that they are accessible from the outside or inside, for example.

A method for transferring energy into a human body using any one of the apparatuses described herein. The method may comprise providing a magnetic field for transferring the energy to an induction coil; and providing a position signal representing a relative position between the induction charging coil and the induction coil. This procedure can be implemented in software or hardware, for example, or in a mixture of software and hardware in an ECU, for example.

A method of operating any one of the positioning devices described herein may comprise a step of conducting energy from an energy storage device to the receiving element and/or the induction coil. This procedure can be implemented utilizing software, hardware, or in a mixture of software and hardware in an ECU. This procedure may use a computer program containing program code. The computer program may be stored on a machine-readable medium or storage medium (e.g., a semiconductor memory, a hard disk memory, and/or an optical memory). In some instances, the computer program may be used to perform, implement, and/or drive the steps of the procedure according to one of the above-described methods.

BRIEF DESCRIPTION OF THE DRAWINGS

Examples of the approach presented here are shown in the drawings and explained in more detail in the following description.

DETAILED DESCRIPTION

In the following description, examples are given. In the figures, reappearing elements use identical signs, whereby a repeated description of these elements is omitted. However, the present disclosure should not be limited to any single embodiment described herein. The limitations described are interchangeable. The device may be practiced using any combination of the limitations described herein.

Figure 1:
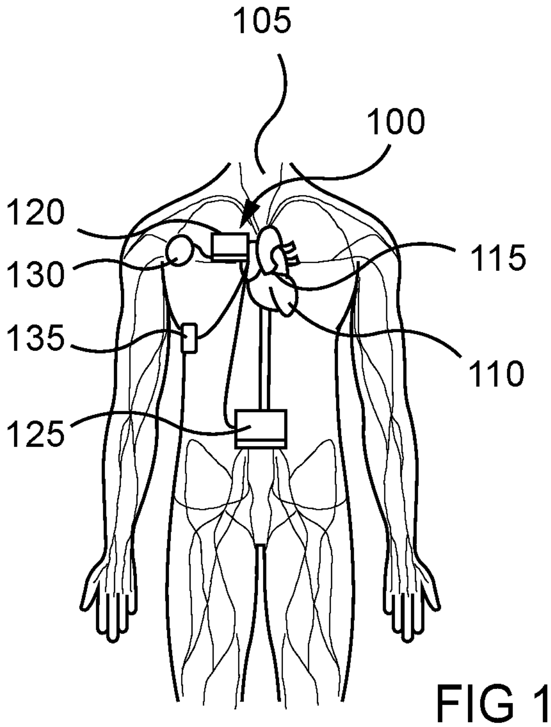
FIG. 1 shows a schematic representation of an execution example of a heart support system in a human body.

FIG. 1 shows a schematic representation of an exemplary embodiment of a Heart Support System 100 in a human body 105. The Heart Support System 100, which may also be referred to as a Cardiac Support System or Mechanical Circulatory Support system, may be a ventricular assist device (VAD). In this illustration, the human body 105 is shown with partially visible internal organs to show intracorporeal components. The Heart Support System 100 may include an intracorporeal components arranged inside the heart 110 between the left ventricle and the aorta. The Heart Support System 100 may be a ventricular assist device comprising a pump and an intracorporal control device 120. The Cardiac Support System 100 may support the heart rhythm and restart it, if necessary. The energy used to power the Cardiac Support System 100 may be transmitted transcutaneously by means of the device described in more detail in FIG. 2. In some embodiments, the Cardiac Support system 100 may comprise an intracorporeal energy storage unit 125, e.g. a battery, configured store energy. For transcutaneous transfer of energy into the body 105, the Cardiac Support System 100 may also include a first induction coil 130 and a second induction coil 135. Both the induction coil 130 and the second induction coil 135 may be configured to transmit a magnetic field to inductively transmit energy to the other components of the Cardiac Support System 100, such as the other induction coil.

Figure 2:
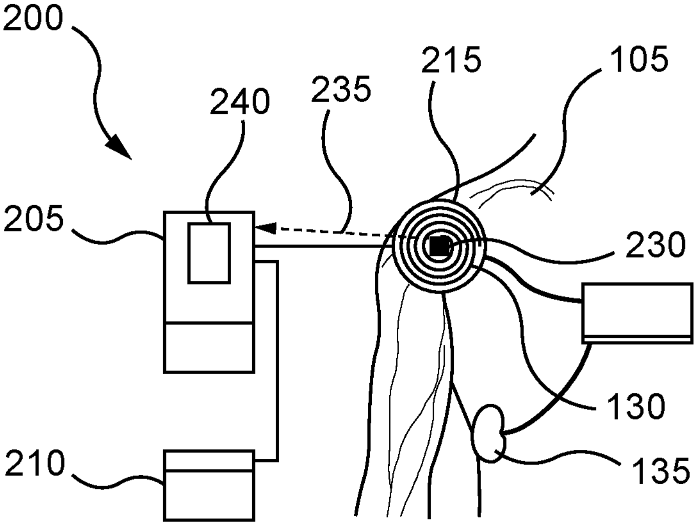
FIG. 2 shows a schematic representation of an execution example of a device with a control device.

FIG. 2 shows a schematic representation of an exemplary embodiment of a transcutaneous energy transfer (TET) device 200 comprising a control device 205. The control device 205, which can also be called a control unit, may be connected to an extracorporeal energy storage device 210, e.g. a battery with an adapter. The control unit 205 may be configured to direct energy from to the extracorporeal energy storage device 210 to the transmission device 215. The energy transmission device 215 may comprise an induction charging coil 220 (see FIG. 3) configured to generate a magnetic field to transfer the energy provided by the control device 205 to an intracorporeally located induction coil 130. To achieve energy transfer, the induction charging coil 220 may be positioned on the outside of the body 105 above the intracorporeal induction coil 130. In some instances, the induction charging coil 220 and intracorporeal induction coil 130 may be disposed concentrically. The transmission device 215 may comprise a device connected to the induction charging coil 220. The induction charging coil 220 may be directly connected to the control unit 205.

The Cardiac Support System 100 or the transcutaneous energy transfer (TET) device 200 may, in some embodiments, include a position sensor device 230 configured to detect a relative position between the induction charging coil 220 and the induction coil 130 and to provide a position signal 235 representing the relative position to the control device 205. In some embodiments, the control device 205 may include a display device 240. Using the position signal 235, the display unit 240 may display positional information or instructions related to how to improve relative position visually using symbols (e.g., representing the coils or a direction or quantity to move the transmission device) and/or using words, statements, sounds, or haptic feedback. The display unit 240 may also be configured to display patient information or information about the Cardiac Support System 100. The display unit 240 may be configured to generate a graphical display to convey the information to a patient or other user. The display unit can also be configured to output information via light symbols, beeps, haptic feedback by means of one or more vibration units, arrows, changes in color grading in the display output, coloring of the display edges, and/or a visual percentage indication for the alignment.

Figure 3:
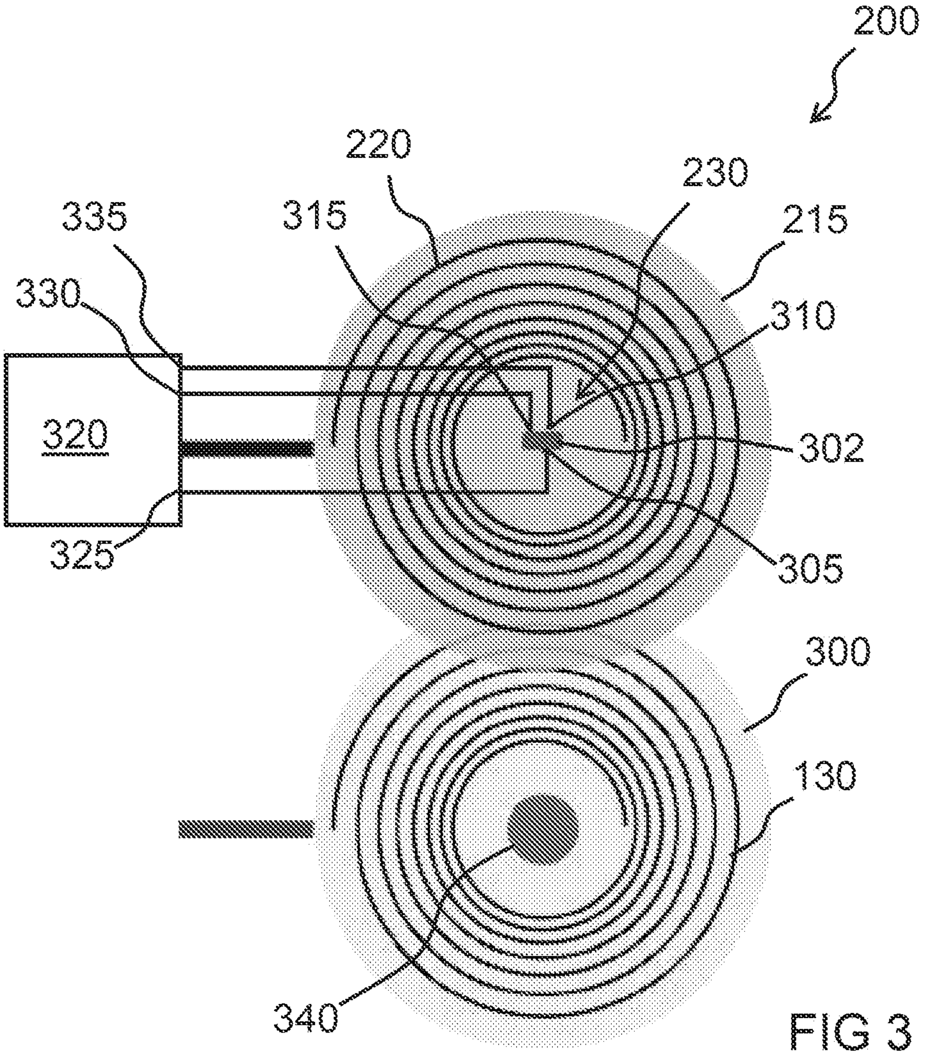
FIG. 3 shows a schematic top view of an execution example of one device.

FIG. 3 shows a schematic top view of an example of a TET device 200. The TET device 200 may comprise an extracorporeal transmission device 215 and an intracorporal transmission device 300. According to some embodiments, the TET device 200 may comprise a sensor device 230. The sensor device may be a Hall sensor 302. The Hall sensor 302 may be disposed in the middle of the induction charging coil 220, which can also be called TET coil. The Hall sensor 302 may comprise a ground connection 305, a supply voltage 310, and output 315. The sensor device 230 may be connected to a microcontroller 320 with A/D conversion. In some instances, the microcontroller 320 may be a component of the control device 205. The ground connection 305 of the Hall sensor 302 may be connected to a ground 325 of the microcontroller. The supply voltage 310 may be connected to the operating voltage 330 of the microcontroller 320, and the output 315 may be connected to pin 335 with A/D conversion. The intracorporeal transmission device 300, which can also be described as an intracorporeal TET coil, may comprise an induction coil 130. A small permanent magnet 340 may be disposed in the center of the intracorporeal induction coil 130 to provide a magnetic field that can be detected by the sensor device 230. As the extracorporeal transmission device 215 and the intracorporeal transmission device 300 become concentrically aligned, the Hall sensor 302 is brought into the magnetic field of the permanent magnet 340. As illustrated in FIG. 3, the extracorporeal transmission device 215 can be offset from the intracorporeal transfer device 300, and as such, the magnetic field cannot be fully detected by the sensor 302.

Figure 4:
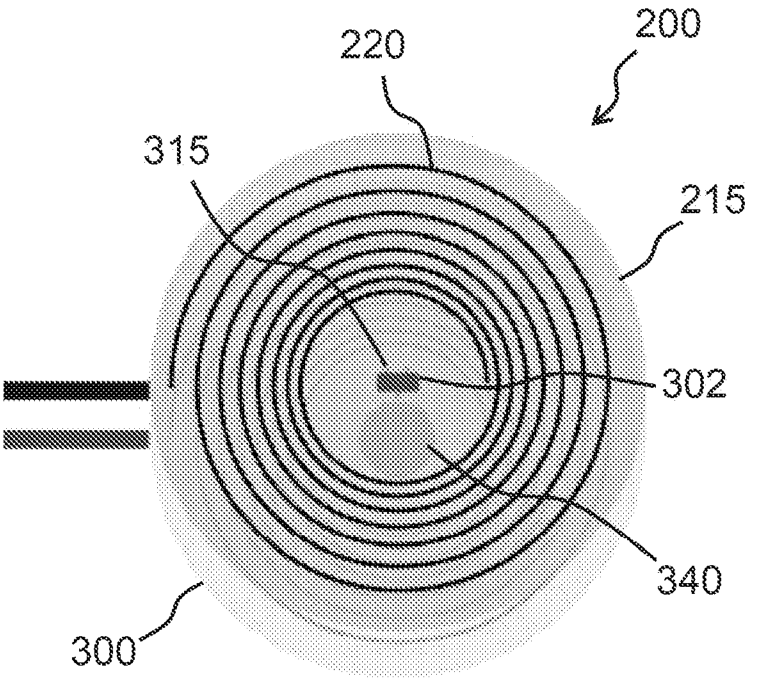
FIG. 4 shows a schematic top view of an example of a fixture.

FIG. 4 shows a schematic diagram of an embodiment of the TET device 200. As depicted in FIG. 4, the extracorporeal transmission device 215 is almost concentrically arranged relative to the intracorporeal transfer device 300. This arrangement can allow the magnetic field provided by the permanent magnet 340 to be detected by the Hall sensor 302. The alignment may change the voltage at output 315 of the Hall sensor 302. For example, the voltage at output 315 of the Hall sensor 302 may increase or decrease, depending on the polarity of the magnetic field. The Hall sensor 302 may be calibrated by averaging the output 315 over a short period of time when a magnet is not near the extracorporeal induction charging coil 220. This calibration may allow a zero value to be determined. A maximum deviation from the zero value may be determined by placing the Hall sensor 302 in direct contact with the permanent magnet 340. Using the zero value and maximum deviation, the relative distance between the extracorporeal charging coil 220 and the intracorporeal induction coil 130 can be determined based on the output 315.

Figure 5:
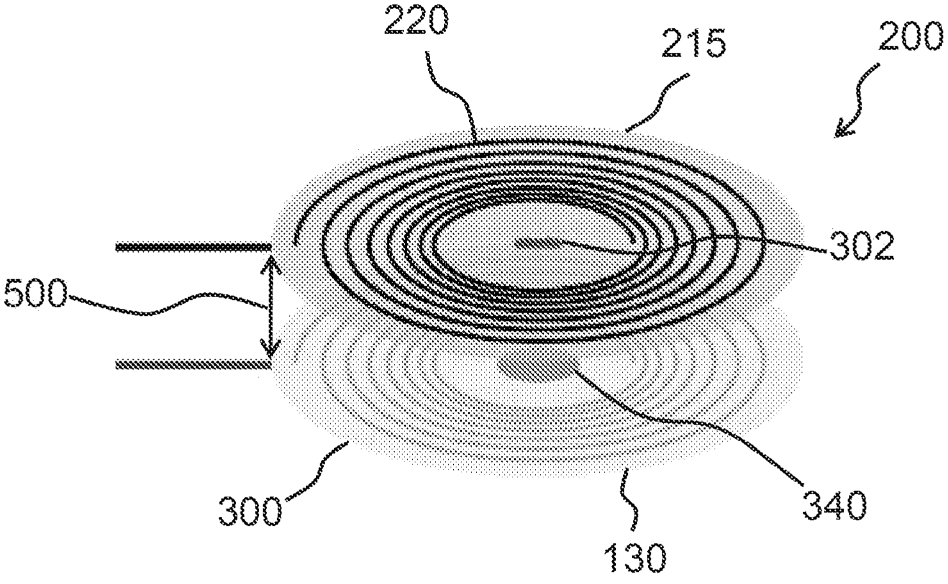
FIG. 5 shows a perspective view of an example of a fixture design.

FIG. 5 shows another perspective of the TET device 200 depicted in FIG. 4. As shown in FIG. 5, the extracorporeal transmission device 215 is almost concentrically arranged relative to the intracorporeal transfer device 300. The magnetic field provided by the permanent magnet 340 can be transmitted through the Hall effect and may be detected by the Hall sensor 302. Based on the output voltage of the Hall sensor 302, the relative distance 500 between the induction charging coil 220 and the induction coil 130 can be determined. In some embodiments, the control unit 205 may be configured to receive the output voltage from the Hall sensor 302 and determine the relative position of the induction coils 220 and 130.

Figure 6:
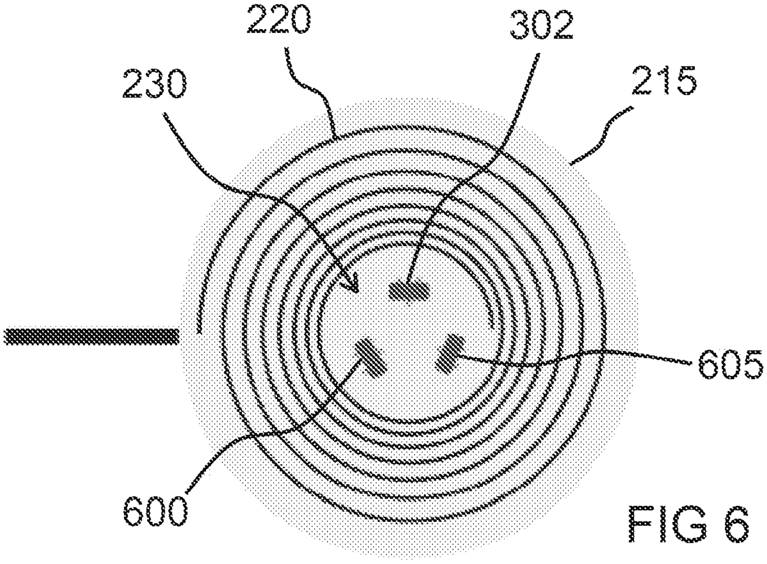
FIG. 6 shows a schematic top view of an execution example of a transmission device.

FIG. 6 shows a schematic top view of an embodiment of an extracorporeal transmission device 215. The transfer device shown in FIG. 6 may be substantially similar to the those described in the previous FIGS. 2 to 5. As illustrated in FIG. 6, the sensor device 230 of the transmitter 215 may include at least three Hall sensors: a first Hall sensor 302, a second Hall sensor 600, and a third Hall sensor 605. The three Hall sensors 302, 600, 605 may be disposed in or toward the middle of the extracorporeal induction charging coil 220 and arranged in a triangle or any desired shape.

Figure 7:
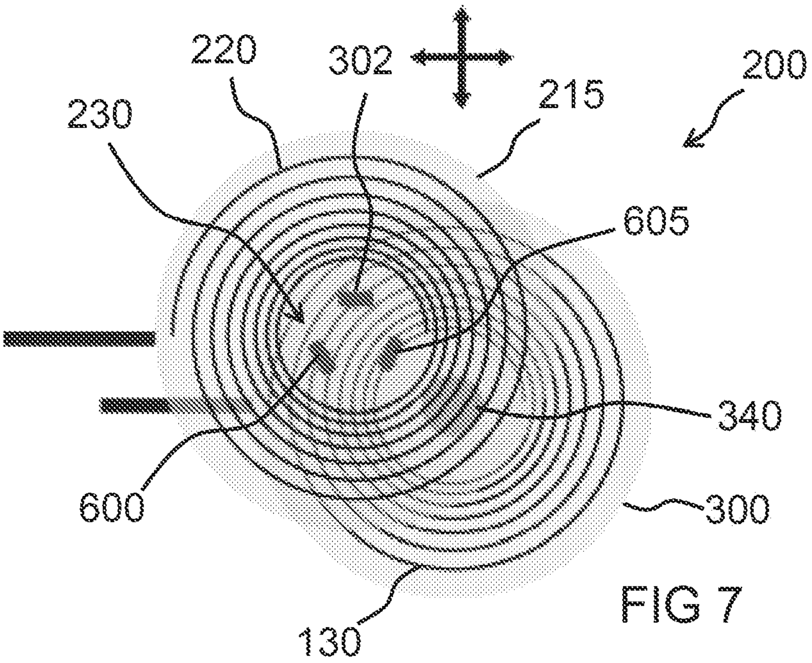
FIG. 7 shows a schematic top view of an example of a fixture.

FIG. 7 shows a schematic top view of the TET device 200, which may be substantially similar to those in FIGS. 2 to 6. The TET device 200 can comprise an intracorporal transfer device 300, which is partially overlaid by the extracorporeal transmission device 215 as illustrated in the figure. The extracorporeal transmission device 215 may comprise a sensor device 230 that may include a first Hall sensor 302, a second Hall sensor 600, and a third Hall sensor 605. As shown in FIG. 7, the Hall sensors 302, 600, and 605 may be disposed in a middle section of the extracorporeal induction charging coil 220 and arranged in a triangle. The intracorporeal induction coil 130 of the intracorporeal transfer device 300 may include a centrally-arranged permanent magnet 340. The control unit 205 may be configured to determine the exact direction and quantification of the deviation of the induction charging coil 220 from the induction coil 130 using the output voltages of the Hall sensors 302, 600, and 605 via triangulation. For example, if the extracorporeal induction charging coil 220 approaches the intracorporeal induction coil 130 from the side, one of the Hall sensors will detect a greater deviation from the zero value than the other sensors. Specifically, as shown in the embodiment of FIG. 7, the measured value of the third Hall sensor 605 will deviate more from a zero value than that of the second Hall sensor 600 and the first Hall sensor 302, if the extracorporeal induction coil 220 approaches the intracorporeal induction coil 130 laterally from the left side of the figure. Based on the output of the three Hall sensors 302, 600, and 605, the control unit 205 may determine the position of the extracorporeal induction coil 220 relative to the intracorporeal induction coil 130. The control unit 205 may further determine the direction the extracorporeal induction coil 220 is moving or is required to move such that it becomes concentrically aligned with the intracorporeal induction coil 130. For example, as illustrated in FIG. 7, the control unit 205 may determine that the center of the Hall sensors 302, 600, and 605 is to the left of the permanent magnet 340 based on the output voltage of each Hall sensor. The control unit may determine that the induction charging coil 220 should be moved in the direction of the third Hall sensor 605 until the induction coils 130 and 220 are concentrically aligned.

Figure 8:
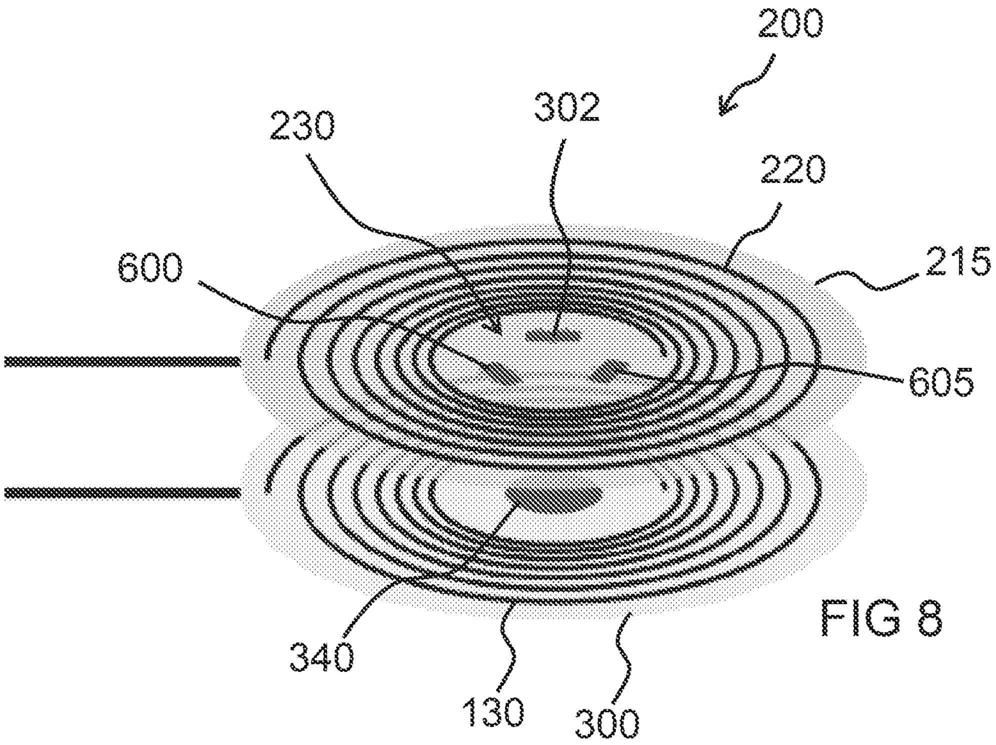
FIG. 8 shows a perspective view of an execution example of a fixture.

FIG. 8 shows an isometric perspective of the TET device 200 shown in FIG. 7. In the figure, the induction charging coil 220 is concentrically disposed relative to the induction charging coil 130. In this position, the measured values of the Hall sensor 302, the second Hall sensor 600, and the third Hall sensor 605 can be the same or substantially the same. Thus, the control unit may determine that the permanent magnet 340 is located an equal distance or a substantially equal distance from each of the sensors.

Figure 9:
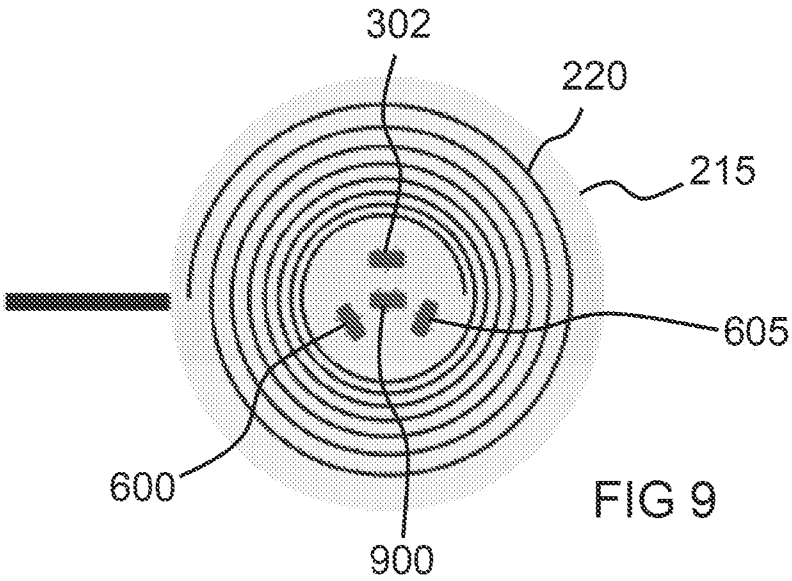
FIG. 9 shows a schematic plan view of an example of a transmission device with a fourth Hall sensor.

FIG. 9 shows a top view of an embodiment of a transmission device 215 that is substantially similar to the transmission device described above in conjunction with FIG. 6. The transmission device can include at least three Hall sensors 302, 600, and 605. The transmission device can include a fourth Hall Sensor 900 configured to determine the position of the extracorporeal induction charging coil 220 relative to the intracorporal induction coil. The first Hall sensor 302, the second Hall sensor 600 and the third Hall sensor 605 may be arranged concentrically around a center of the extracorporeal induction coil 220, while the fourth Hall sensor 900 may be disposed in the center of the other Hall sensors 302, 600, and 605.

Figure 10:
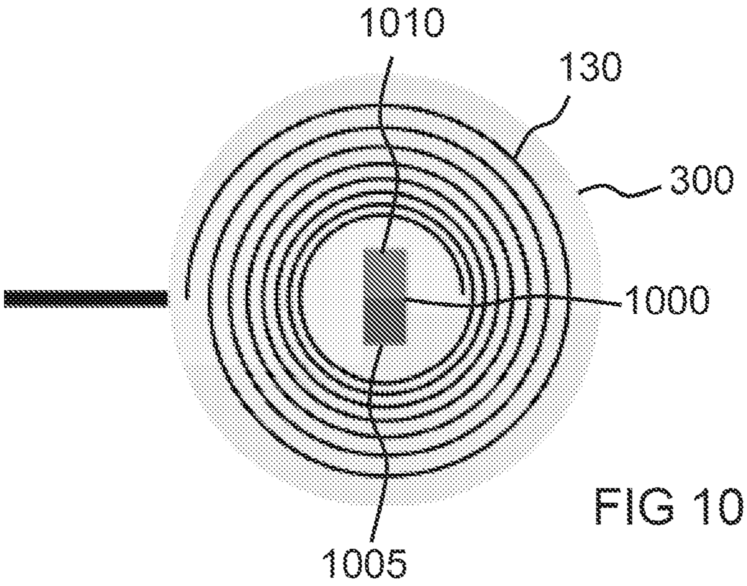
FIG. 10 shows a schematic plan view of an example of an intracorporeal transfer device with a permanent bar magnet.

FIG. 10 shows a diagram of an intracorporeal transfer device 300 that comprises a permanent bar magnet 1000. The intracorporeal transfer device 300 depicted in FIG. 10 may be substantially similar to the intracorporeal transfer device 300 described above in any one of FIGS. 3-5, 7 and 8. In some instances, the center of the induction coil 130 may be fitted with a permanent rod magnet 1000. The permanent bar magnet 1000 can include a north pole 1005 and a south pole 1010. The position of the extracorporeal induction charging coil 220 (as shown in FIG. 9) may be determined relative induction coil 130 based on the output voltage of the four Hall sensors 302, 600, 605 and 900 based on the poles 1005, 1010 of the bar magnet 1000. The Hall sensors of the induction charging coil, which are closer to the north pole 1005, may indicate a value less than half the supply voltage (Vcc) of the sensors. The Hall sensors, which are closer to the south pole 1010, may show a value between Vcc/2 and Vcc. The fourth Hall sensor 900, described in FIG. 9, may be configured to find the center of the induction coil 130. If the fourth Hall sensor is disposed in the middle of the permanent magnet 1000, the output voltage of the fourth Hall sensor will be Vcc/2. For example, the control unit 205 may determine that the extracorporeal induction charging coil 220 is aligned concentrically over the intracorporeal induction coil 130 if the fourth Hall sensor measures Vcc/2, at least one of the other Hall sensors measures a value smaller than Vcc/2, and at least one other Hall sensor measures a value greater than Vcc/2.

Figure 11:
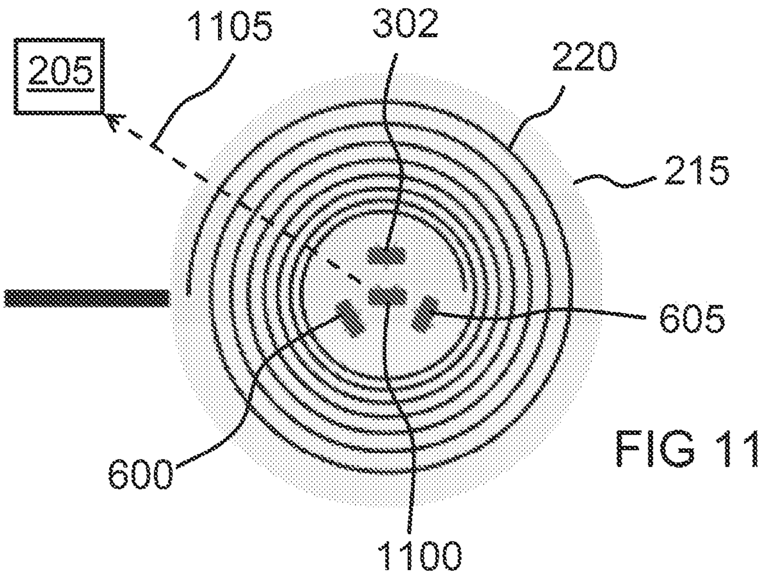
FIG. 11 shows a schematic plan view of an example of a transmission device with a gyro sensor.

FIG. 11 shows a schematic top view of an embodiment of a transmission device 215 that may be configured substantially similar to the transmission device 215 described above in conjunction with any one of FIGS. 2 through 10. The transmission device may comprise a gyro sensor 1100. The gyro sensor 1100 may be disposed in the center of the induction charging coil 220 and configured to compensate for positional inaccuracies that occur during use of the Cardiac Support System 100, such as twisting of the extracorporeal induction coil 220. The gyro sensor 1110 may be a gyroscope, a micro-electromechanical systems (MEMS) gyroscope, such as a gyrometer, a ring laser gyroscope, a fiber optic gyroscope, or the like. The extracorporeal induction charging coil 220 may comprise any suitable number of Hall sensors (e.g., as illustrated, a first Hall sensor 302, a second Hall sensor 600, and a third Hall sensor 605), which may be arranged concentrically around a center of the coil 220. The intracorporeal induction coil, in some instances, may also include a permanent magnet (1000) as described herein. In some embodiments, energy transfer can be performed while the patient is in an upright position, e.g. sitting upright or standing. Once the patient is upright, the transmission device 215 can be positioned. During the positioning process, the gyro sensor 1100 may measure an acceleration of gravity (9.81 m/s^2) and transmit a baseline orientation signal 1105 to the control unit 205. The control unit 205 may be configured to position or generate instructions for positioning the extracorporeal induction coil 220 using the baseline orientation signal, which can also be referred to as a spatial or "room" signal. As the extracorporeal induction coil 220 is moved into place, the gyro sensor 1100 may generate an output signal in response to the movement and transmit the output signal to the control unit 205. The control unit 205 may be configured to update the relative position of the extracorporeal induction coil 220 or the positioning instructions based on the update output signal from the gyro sensor 1100.

Figure 12:
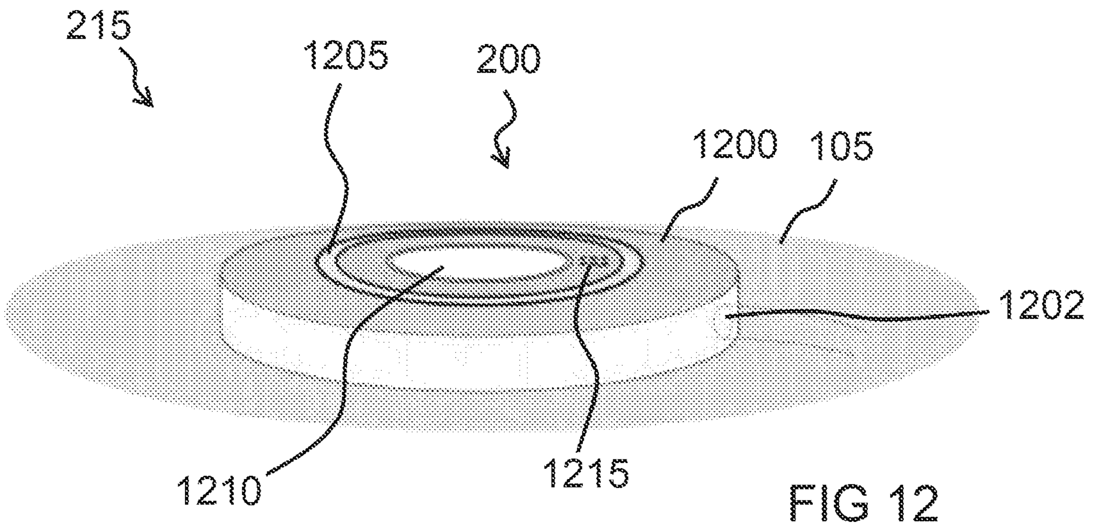
FIG. 12 shows a perspective view of an example of an extracorporeal transfer device with integrated control unit.

FIG. 12 shows an embodiment of an extracorporeal transmission device 215 further comprising an integrated control unit. The transmission device 215 may be configured substantially similar to the transmission devices described above in conjunction with any one of FIGS. 2-9 and 11. In some instances, the transmission device 215 may arranged in a housing 1200. For example, the integrated control unit may be at least partially located within the housing 1200. The housing 1200 may be watertight, fluid impermeable, and/or dustproof. The housing 1200 may be attached to the interface 1202 and sealed to ensure water, fluid, and/or dust resistance. In an operational state, the transmission device 215 may rest directly on the body 105. The transmission device 215 may also comprise a ring-shaped light unit 1205 configured for the visual display of position information. For example, the ring light may light up only in a direction relative to the center of the transmission device to indicate the transmission device needs to be moved in that direction. For example, the ring light may or a portion of it may flash at a rate that is related to the distance of offset (e.g., the light may blink more quickly as it gets closer to the target). The ring-shaped light unit 1205 may be arranged on the side of the transmission device 215 opposite the body 105, i.e. the side or face of the transmission device 215 that is not in contact with the body 105. The transmission device 215 may comprise a mechanical button 1210 disposed in the center of the ring-shaped light unit 1205. The button 1210 may be designed as part of the control unit and be configured to control various components of the transmission unit 215 or the Cardiac Support System 100. For example, pressing the button 1210 may trigger a system function such as muting alarms. Further, the transmission device 215 may comprise a loudspeaker unit 1215 arranged between the button 1210 and the light unit 1205 for acoustic output of the position information, patient information, or other information related to the use of the Cardiac support system. As illustrated in the example shown in FIG. 12, the button 1210 can be a circle concentrically surrounded by the light unit 1205. A speaker unit 1215 can reside between the button 1210 and the light unit 1205. However, it will be understood by one having ordinary skill in the art that the button 1210, the speaker unit 1215, and the light unit 1205 are not limited to these shapes or orientations relative to one another. The button 1210, the speaker unit 1215, and the light unit 1205 may be a variety of shapes and may be oriented in any manner based on the shape and size of the transmission device 215.

Figure 13:
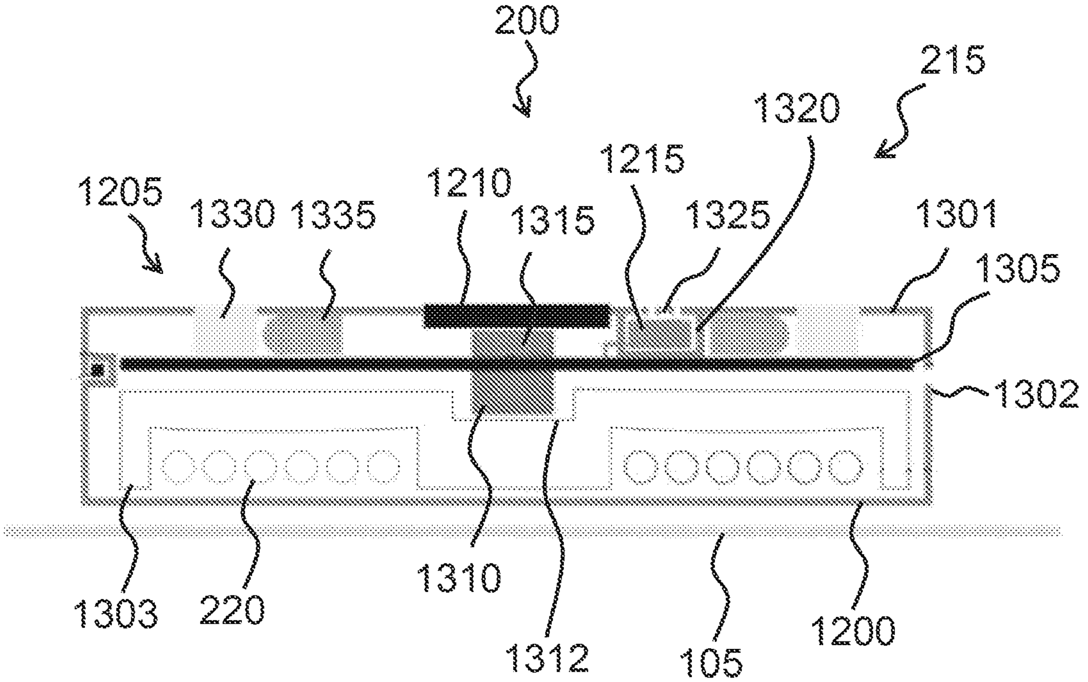
FIG. 13 shows a cross-sectional view of an execution example of an extracorporeal transfer device with integrated control unit.

FIG. 13 shows a cross-sectional view of an example of an extracorporeal transmission device 215 with an integrated control unit similar to the transmission device described in the previous FIG. 12. The housing 1200 of the transmission device 215 may be formed from a lower half of the housing 1302 and an upper half of the housing 1301. The transmission device 215 may comprise a ferrite component 1303. The ferrite component 1303 may be disposed inside the housing 1200 and be arranged as a core of the winding of the induction charging coil 220 and configured to shield the same. A circuit board 1305 may be disposed above the ferrite component 1303. Additional elements of the control unit may be arranged on the circuit board 1305. For example, a vibration unit 1310 for haptic display of the position information may be disposed on any side (e.g., the underside) of the circuit board 1305. The vibration unit 1310 can be in direct contact with the ferrite component 1303. In some embodiments, the ferrite component 1303 may include a recess 1312 to accommodate the vibration unit 1310, which may reduce the overall height of the transmission device 215. The vibration unit 1310 may be configured to and arranged such that vibrations can be transmitted from the vibration unit to the human body 105 via the housing 1200. For example, as illustrated in FIG. 13, the vibration unit may initiate a vibration which is transferred from the ferrite component 1303 to the housing 1200 to the body 105. In some embodiments, a button 1315 with a mechanical knob 1210 may be disposed on the side of the circuit board 1305 opposite the vibration unit 1310 (e.g., the side facing away from the body 105). A speaker unit 1215 may also be arranged beside the button 1210. The speaker unit 1215 may be arranged in a sealed chamber 1320 and configured to emit sound to the patient through a speaker opening 1325, which may be waterproofed for example by sealing the speaker opening with a flexible membrane. Around the button 1210 and the speaker unit 1215 may be a light unit 1205. The light unit 1205 may include an LED or array of LED's 1330 and a ring-shaped light guide 1335.

Figure 14:
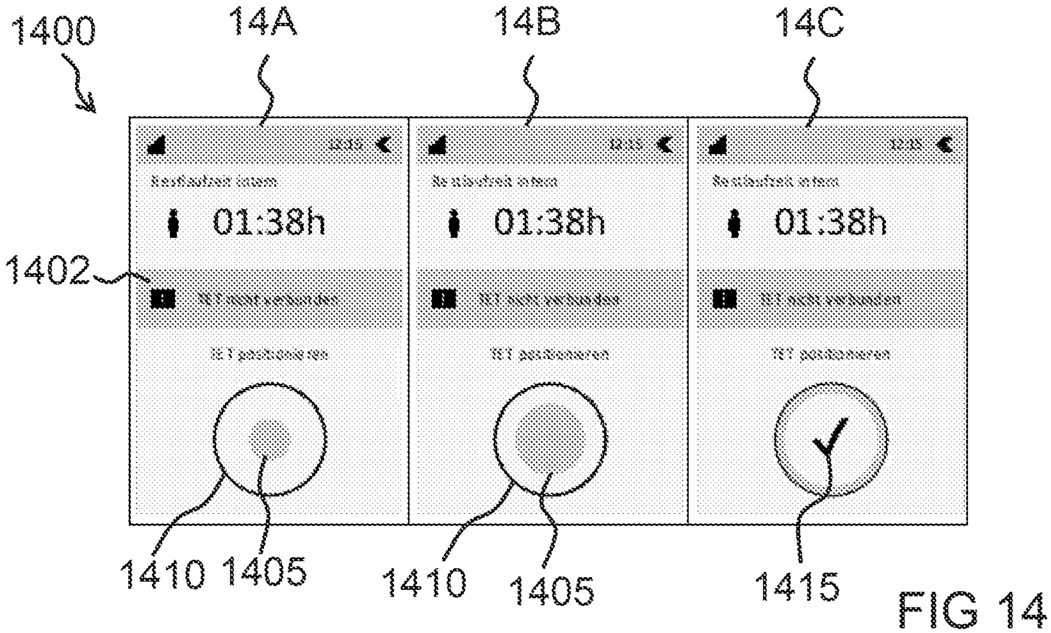
FIG. 14 shows an example of a display for displaying position information.

FIG. 14 shows an example of a display 1400 for displaying position information, patient information, or other information related to the use of the Cardiac Support System 100. The display 1400 may be a graphical display generated by a display unit 240 as described herein. The display unit 240 may be configured to generate the display 1400 or changes thereon. In some embodiments, the control unit 205 may be configured to generate the display 1400 on the display unit 240 and update the display 1400 based on data received by the control unit, e.g. positional data, patient data, or the like. The display 1400 may be configured to execute a user interface, such as a touch user interface. The display 1400 may be a 2.8" display. The display may be adjusted to be displayed on smaller or larger displays and adapted to different aspect ratios, such as 4:3 or 16:9.

FIG. 14 is divided into three FIGS. 14A, 14B and 14C. In these FIGS., various display options are shown. Each of the display options is configured to convey information regarding the relative positioning of an extracorporeal induction charging coil over an intracorporeal induction coil. In the left-hand FIG. 14A, a warning message 1402 with the information "TET not connected, position TET" is shown. Below the warning message 1402, the display includes two concentric circles, which represent a position point 1405 and a position circle 1410 arranged around the position point 1405. Based on any of the position signals described herein, the control device 205 (e.g., as described in connection with FIGS. 2, 12 and 13) may be configured to display position points 1405 of different sizes in the display device 240. For example, as the induction coils become increasing misaligned, the position point 1405 may become smaller. In FIG. 14B, position point 1405 is shaped with a larger diameter than in FIG. 14A, which indicates that the extracorporeal induction coil is approximately aligned with the intracorporeal induction coil. In some instances, the circle will grow as the induction coils come closer to concentric alignment. In the right-hand FIG. 14C, the two coils are generally concentrically aligned, and the display unit 240 may generate a check mark 1415 instead of the position point 1405. After the coils are aligned and the check 1415 appears, the control unit 205 may be configured to instruct the display unit 240 to display a home screen. In some embodiments, the display unit 240 may be configured to return to a home screen after a predetermined period of time. If the induction charging coil slips out of alignment, the display unit may display the positioning screen shown in FIGS. 14A and 14B again.

Figure 15:
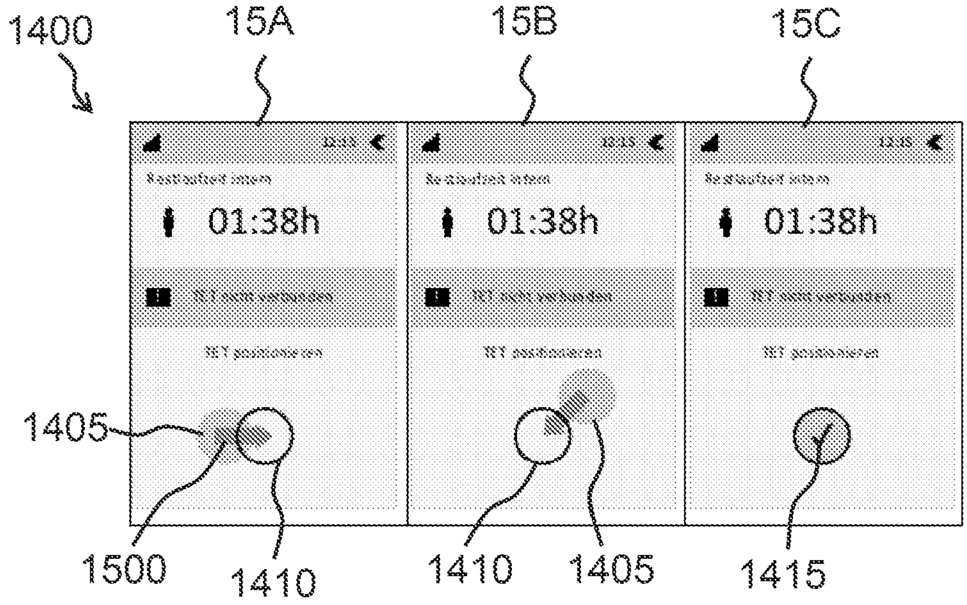
FIG. 15 shows an example of a display for displaying position information.

FIG. 15 shows another example of a display 1400 and includes three FIGS. 15A, 15B and 15C. In these FIGS., various display options for information regarding the positioning of an extracorporeal induction charging coil over an intracorporeal induction coil are shown in a display 1400 of the display unit 240. The position point 1405, shown in FIG. 15 as a filled, light-grey circle in the partial FIG. 15A, may be generated on the display 1400 and represent the position of the extracorporeal induction coil 220. The position circle 1410, shown as an unfilled black circle, may be positioned on a center line of the display 1400 and represent a position of the intracorporal induction coil 130. The position point 1405 may be generated on the display based on the position data of the extracorporeal induction coil relative to the intracorporeal induction coil. For example, in FIG. 15A the position point 1405 may be disposed to the left of the position circle 1410 based on position data, indicating that the extracorporeal induction coil 220 is to the left of the intracorporeal induction coil 130. In some embodiments, the display 1400 may comprise an arrow 1500 configured to indicate the direction in which the extracorporeal induction coil 230 should be moved in order to achieve alignment with the intracorporeal induction coil. FIG. 15B illustrates an example where the position point 1405 is shown laterally above the position circle 1410. In FIG. 15C, the induction coil and induction charging coil are optimally aligned, and a 1415 checkmark appears in the 1400 display. In some embodiments, the position circle 1410 may also be filled in grey when the induction coils are aligned (or provide some other visual indication that correct alignment is achieved, such as a green light).

Figure 16:
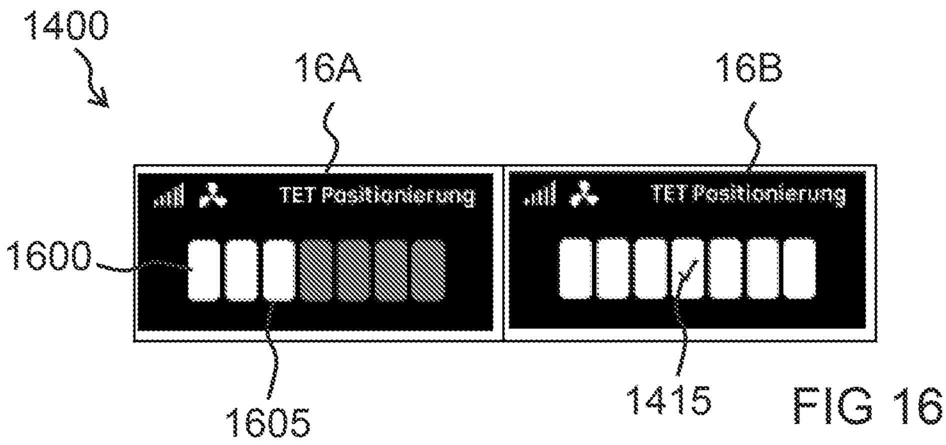
FIG. 16 shows an example of a display for displaying position information with a position bar.

FIG. 16 shows an example of a display 1400, which may include a position bar 1600. FIG. 16 is divided into two partial FIGS. 16A and 16B. The display 1400 variant shown here may be suitable for wide displays with low height or as a component of a display 1400 that includes other information, such as patient information or other information related to the Cardiac Support System 100. As shown in FIG. 16A, the display may comprise a position bar 1600 with any number of bar modules 1605 (e.g., seven as illustrated). The position bar 1600 may be disposed in the middle of the display 1400. A different coloring of the bar modules 1605 (dark grey and white) may represent the degree to which the extracorporeal induction charging coil is aligned with the intracorporeal induction coil. In FIG. 16A, only four exemplary bar modules 1605 are colored grey and three bar modules 1605 are colored white, which may indicate a moderate, but not optimal, alignment of the induction coils. As the alignment between the induction coils improves, more bar modules 1605 become white from left to right. For example, if alignment improved slightly from FIG. 16A, the fourth bar module 1605 may become white. In FIG. 16B, the induction coils may be optimally aligned, and all modules may become white. Once the induction coils are aligned, a check mark 1415 may be generated in the middle of the position bar 1600.

Figure 17:
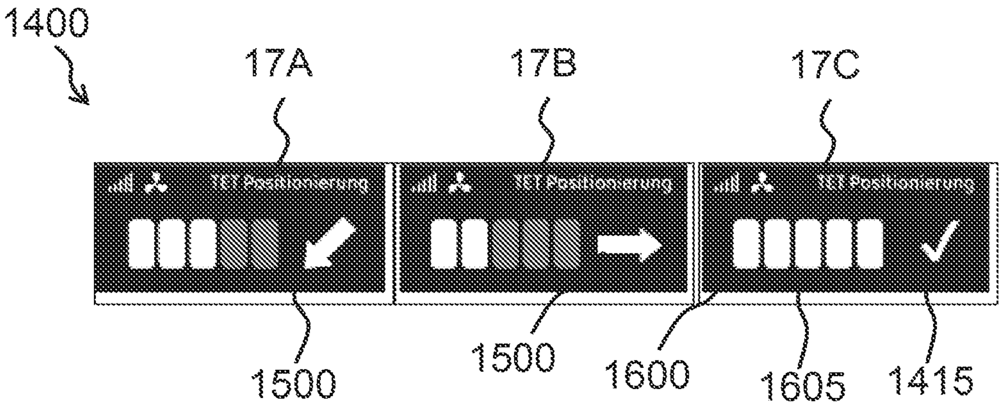
FIG. 17 shows an example of a display for displaying position information with a position bar.

FIG. 17 shows an example of a display 1400 configured to display position information with a position bar 1600. FIG. 17 is divided into three FIGS. 17A, 17B and 17C. The display 1400 shown here is similar to the one in the previous FIG. 16, with the difference that an additional arrow 1500, which is similar to the arrow in FIG. 15, may be included and configured to indicate which direction the extracorporeal induction charging coil 220 should be moved to achieve alignment with the intracorporeal induction charging coil 130. For example, in FIG. 17A the arrow 1500 points diagonally downwards and in the FIG. 17B the arrow 1500 points to the right. The direction of the arrow 1500 in FIGS. 17A and 17B may be determined based on the current position of the extracorporeal induction coil 220 relative to the intracorporeal induction coil 130. The direction of the arrow 1500 may correspond to the direction the extracorporeal induction coil 220 needs to be moved to be in alignment with the intracorporeal induction coil 130. In FIG. 17C, the inductions coils may be optimally aligned to each other. Accordingly, all bar modules 1605 of position bar 1600 are white, and a check 1415 is displayed instead of the arrow 1500.

Figure 18:
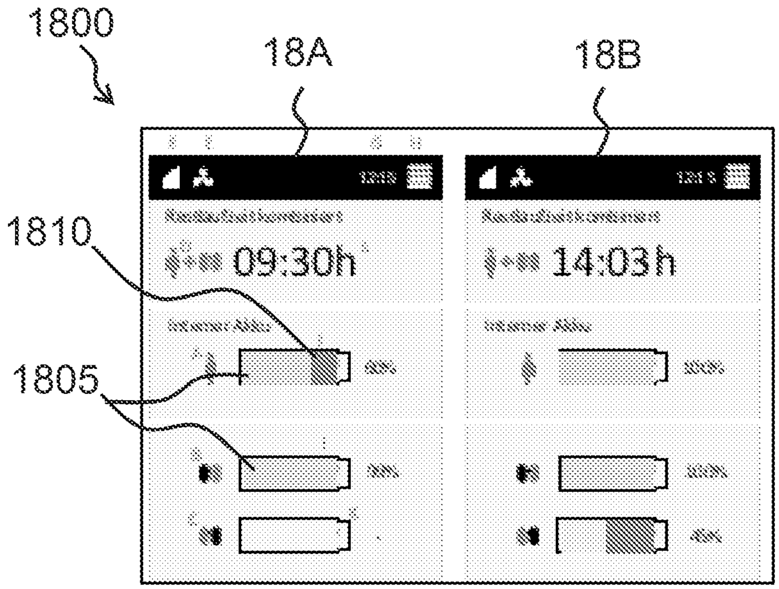
FIG. 18 shows an example of a start display of a display device.

FIG. 18 shows an exemplary embodiment of a start display 1800 to be generated on any display unit 240 as described herein. FIG. 18 is divided into two partial FIGS. 18A and 18B. In the FIGS., different options for displaying information regarding a connected energy storage device are shown. The start display 1800, which may also be called home screen, may include information about connected batteries. For example, in FIG. 18A, the start display 1800 may include a battery symbol I, a battery symbol J, and a battery symbol K, which may correspond with three batteries attached to the Cardiac Support System 100. If a battery is not connected, such as battery K in the example shown here, only the outline of the battery symbol may be shown. In FIG. 18A, two batteries are connected (I and J), and the induction charging coil may be positioned so that energy is supplied to the intracorporal system is transferable. Accordingly, battery symbol I and battery symbol J are filled with colored bars 1805 and gray bars 1810. Each bar may represent 25% of a full charge. In some embodiments, each bar may represent 20%, 10%, 1%, or another portion of a full charge. The color of the bars may represent the following information:

Grey: part of the battery already discharged.

Green: remaining battery charge, total battery charge >50%.

Yellow: remaining battery charge, total battery charge <50%>25%

Red: remaining battery charge, total battery charge <25%.

As shown in FIG. 18B, all three batteries may be connected, and the battery symbol K is displayed filled in. The start display 1800 may also include a symbol A which represents the internal battery (iBAT), a symbol B which represents a first external battery (eBAT1), and a symbol C which represents a second external battery (eBAT2). Further, the start display 1800 may include a symbol D that symbolizes all of the batteries attached to the Cardiac Support System 100. The start display 1800 may also include a remaining charge time (marked as L in FIG. 18A), which indicates how long the iBAT and eBATs can power the Cardiac Support System 100 before charging is required.

The start display 1800 may include a symbol F configured to represent the strength of the connection to the mobile phone network. The start display 1800 may also include a symbol E that represents the functionality of the VAD. Both of the F and E symbols are designed as buttons on a touch-user interface and may be configured to access a corresponding information screen, which may display more specific information. The display unit 240 may be a touch screen configured to receive touch inputs. In some embodiments, the display unit 240 may include analog buttons to navigate the user interface generated on the display unit 240. For example, pressing the E symbol may generate a pump information display that includes pump speed, pump volume, or other pump related information. The start display 1800 may also include a Symbol G that represents the current time and a symbol H, which may be a touch-user interface button to enter the menu for the Cardiac Support System 100 in some embodiments.

Figure 19:
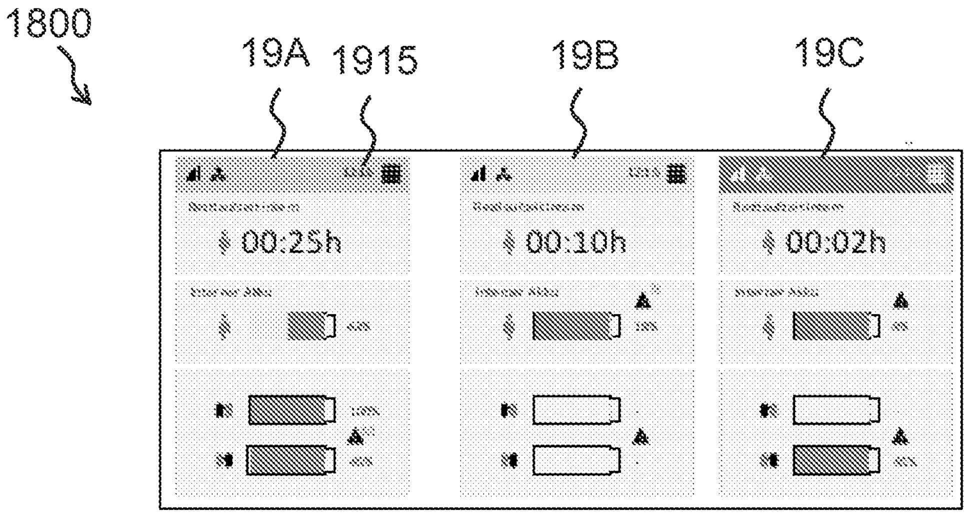
FIG. 19 shows an example of a start display of a display device.

FIG. 19 shows an example of a start display 1800 of a display unit 240 as described in any embodiment herein. The start display 1800 in FIG. 19 may be substantially similar to the start display described in FIG. 18. FIG. 19 is divided into three FIGS. 19A, 19B and 19C. Each of the FIGS. shows different ways of displaying information regarding a connected energy storage device. In some embodiments, such as the embodiment shown in FIG. 19, the display unit 240 may be designed to display different alarm conditions. For example, the start display 1800 may include the header 1915, which is shown in FIGS. 19A, 19B, and 19C as the blue, yellow, and red bar at the top of the display 1800. The control unit 205 or the display unit 240 may be configured to generate the header 1915 when an alarm condition is present. The header may be colored based on the type or urgency of the alarm that is present. For example, the blue header in FIG. 19A is an example of a low priority alarm; the yellow header in FIG. 19B is a medium priority alarm; and the red header in FIG. 19C is a high priority alarm.

Additionally, the control unit 205 or the display unit 240 may be configured to generate an alarm symbol M between the Battery symbol J and the battery symbol K. The alarm signal M may indicate a variety of dangerous conditions. For example, the alarm symbol M may represent a slipping of the induction charging coil. The alarm symbol M may indicate that no battery is connected. In FIG. 19B, another alarm symbol N may be generated by the control unit 205 or the display unit 240. The alarm symbol N may be arranged next to the battery symbol I. As shown in FIG. 19B, the alarm symbol N may represent a low energy level of the intracorporeal energy storage device. In FIG. 19C, several alarms are active, and several alarm symbols accordingly appear at the corresponding locations on the display. As a part of the user interface described above, the display device 240 may be configured to display further information regarding the alarm message when the alarm symbols are pressed by the patient or another user.

Figure 20:
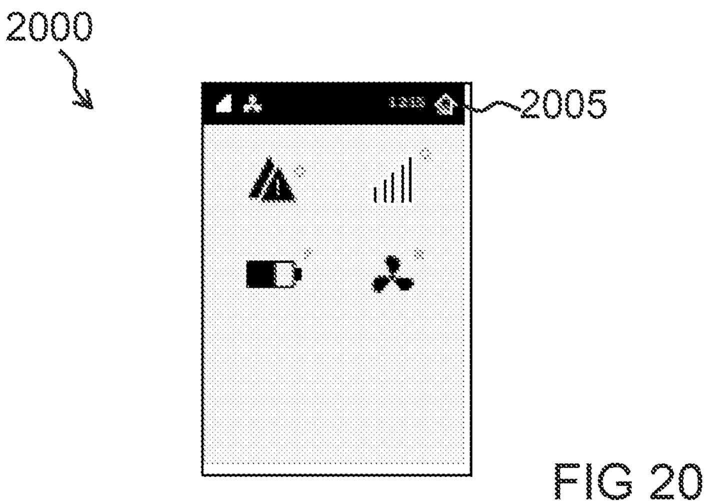
FIG. 20 shows an example of a menu display of a display device.

FIG. 20 shows an example of a menu display 2000, which may be generated on a display unit as described above. The menu display 2000 may include a header 2005 that is substantially similar to the header 1915 described in FIG. 19

As shown in FIG. 20, the header 2005 may include a symbol S in the form of a house instead of a menu symbol (a hamburger menu icon) on the right of the header 2005. The symbol S may represent a button to get to the start display. The menu display 2000 may also include a Q symbol and an R symbol, which may be buttons in a touch-user interface in some embodiments. In this example, the Q symbol represents the strength of the connection to the mobile phone network, and the R symbol represents the functionality of the pump. In addition, an O symbol may be displayed and may be designed as a button to access the alarm history. A P symbol may also be displayed and configured as a button to get to the battery information.

Figure 21:
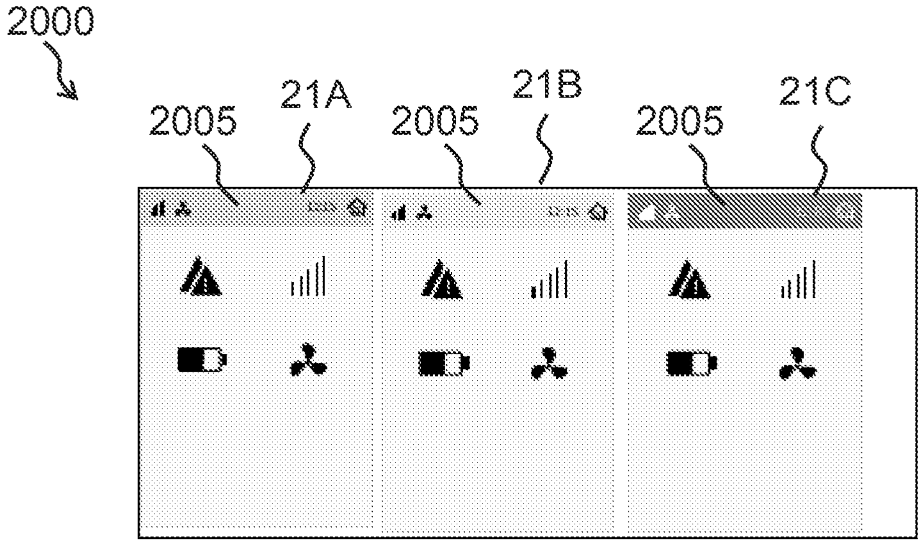
FIG. 21 shows an example of a menu display of a display device.

FIG. 21 shows an example of a menu display 2000 of a display unit 240 that is substantially similar to the menu display 2000 described in any one of the previous FIG. 20 or FIG. 21 is divided into three FIGS. 21A, 21B and 21C. Similar to the embodiments described herein, the header 2005 may be colored differently based on the presence of an alarm and the urgency or severity of the alarm. Similar to FIG. 19, the header 2005 in FIG. 21A is colored blue and may indicate a low priority alarm. The header 2005 in the middle FIG., FIG. 21B, is colored yellow and may indicate a medium priority alarm, and the header 2005 of the right FIG. 21C is colored red and may indicated a high priority alarm. Depending on the alarm present, the header 2005 may be colored differently. The colors and associated alarm levels are not limited to those described herein. The display unit 240 may include a setting that allows patient or another user to set the colors for each alarm.

Figure 22:
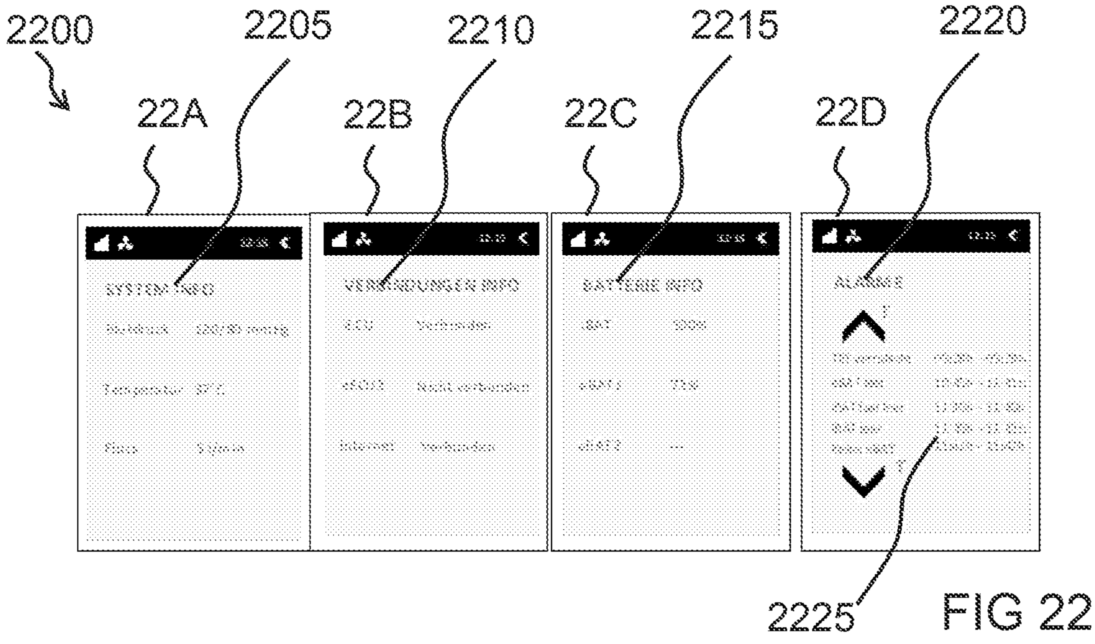
FIG. 22 shows an example of a system display device.

FIG. 22 shows an example of a system display 2200 which may be generated on a display unit as described in FIG. 2. FIG. 22 is divided into four FIGS. 22A, 22B, 22C, and 22D, which include displays for various system information. The system display 2200 and precise information on system data may be accessed in a third level of the interface (i.e. two-clicks or touches away from the start display 1800) so that patients are not overwhelmed with information. Using the system display 2200, the patient may access specific information as shown in the FIGS. Alternatively, if one of the parameters reach a critical value, the patient may be alerted via an alarm. For example, if the patient's heart rate rises or their blood pressure spikes, an alarm may be generated on the start display 1800 or the menu display 2000 as described above. Upon clicking the alarm symbol or the header, detailed information 2205 regarding the patient's vitals may be shown on the display unit 240, as shown in FIG. 22A. In another example shown in FIG. 22B, connectivity information 2210 regarding the intracorporeal VAD may be shown. For example, the connectivity information 2210 may indicate whether the components, such as the control units, of the cardiac support system 100 are connected to one another or whether the system is connected to the internet. As an example, in FIG. 22B, the iECU is connected to the system, and the system is connected to the internet. However, the eECU 2 is not connected. The display unit 240 may be configured to display progress curves or a connection history when the corresponding parameter is pressed. For example, a patient may select a component from the connectivity information 2210, and the progress curve or connection history may be shown.

In FIG. 22C, a battery information display 2215 may show detailed battery information based on the status of the available energy. The battery display 2215 may also include additional information such as the runtimes for the individual batteries. In addition, graphs showing the time course of the battery charge may be displayed. In some embodiments, the additional information about a particular battery may be shown after a user selects a battery in the battery information display 2215 using a touch-user interface as described above. In the right-hand FIG. 22D, an alarm history 2220 is shown. In this exemplary embodiment, two scroll buttons (T) may be shown in the alarm history 2220 and configured to allow a user to scroll through the alarms or an alarm history. In addition, the alarm history 2220 may include a time 2225 that the alarm occurred and a time when the alarm ended or was silenced by the user. As shown in FIG. 22, system information may be displayed in individual display. In each display, additional information or plots may be displayed after touching the individual parameters. In some embodiments, the system information shown in FIG. 22 may be included in a single display that a user may scroll through. Other information may also be included about the Cardiac Support System 100 such as pump speed, pump volume, or the like.

Figure 23:
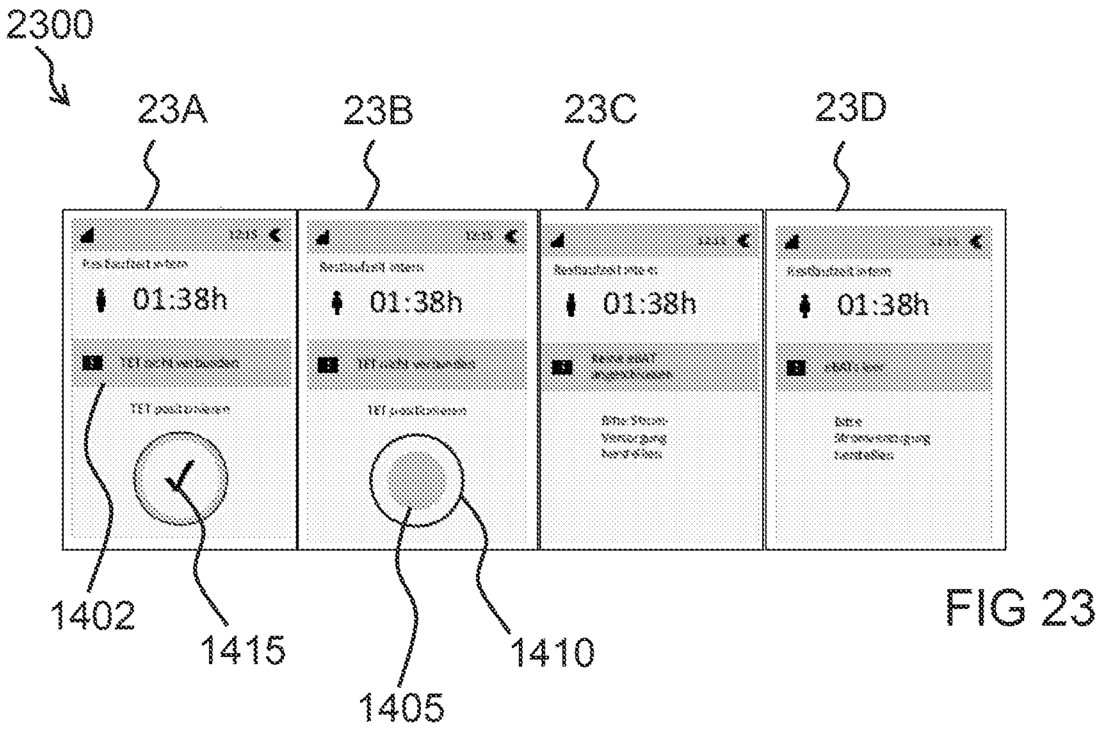
FIG. 23 shows an example of an alarm display unit.

FIG. 23 shows an example of an alarm display 2300 to be generated on the display unit 240 as described in FIG. 2. FIG. 23 is divided into four FIGS. 23A, 23B, 23C, and 23D, which display different warning messages 1402. In the example embodiments shown in FIG. 23, the warning messages 1402 may be low priority and colored blue. For example, the warning message 1402 in FIG. 23A may indicate a connection error between the extracorporeal induction charging coil and the intracorporeal induction coil even though the induction coils are correctly positioned. As discussed above, the correct positioning of the induction coils may be indicated by a check 1415. FIG. 23B shows a warning message 1402 that may indicate a connection error between the extracorporeal induction charging coil and the intracorporeal induction coil due to incorrect positioning of the induction coils. As discussed above, when the induction coils are out of alignment, the position of the induction charging coil may be indicated by a position point 1405 in a position circle 1410. FIG. 23C depicts an example embodiment where the warning message 1402 indicates a connection error between the extracorporeal induction charging coil and an external energy storage device, or battery. In FIG. 23D, the warning message 1402 may indicate that one or more of the external batteries is empty.

Figure 24:
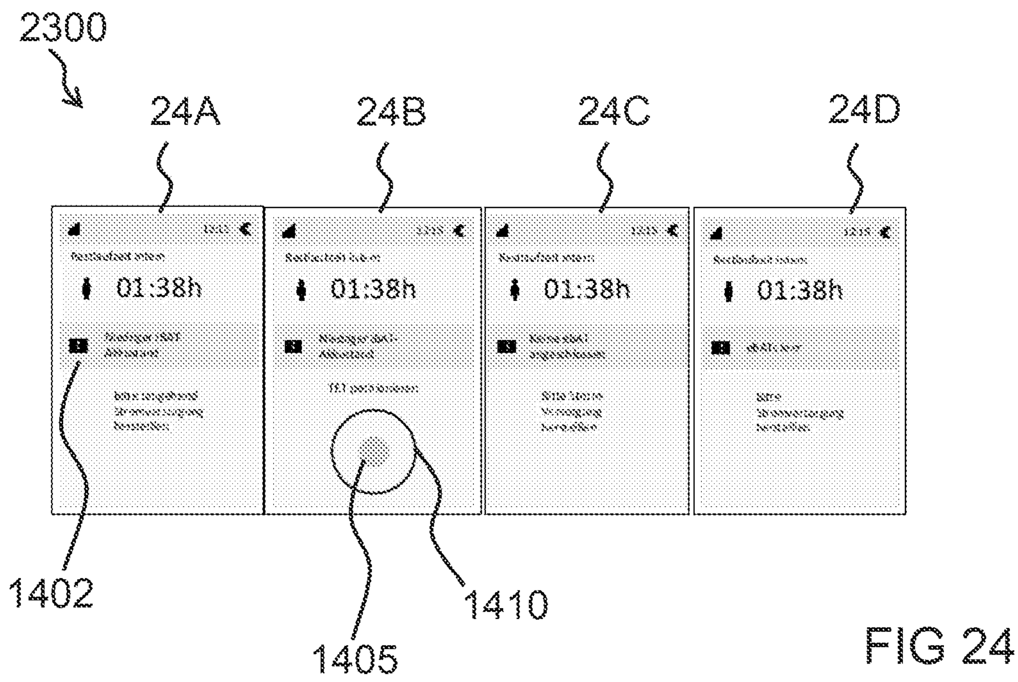
FIG. 24 shows an example of an alarm display unit.

FIG. 24 shows another example of an alarm display 2300. The alarm display 2300 of FIG. 24 may be substantially similar to the alarm display described in the previous FIG. 23, with the difference that the warning messages have a medium priority in the exemplary embodiment shown here. Accordingly, the warning messages 1402 may be colored yellow. FIG. 24 is divided into four FIGS. 24A, 24B, 24C and 24D. In the example embodiments shown in FIG. 24, the warning message 1402 in FIG. 24A may indicate a low energy level of an intracorporeal energy storage. In FIG. 24B, the warning message 1402 may indicate a low energy level of an intracorporeal energy storage device caused by an incorrectly positioned extracorporeal induction charging coil. As discussed above, the position of the induction charging coil may be indicated by a position point 1405 in a position circle 1410. In FIG. 24C, the warning message 1402 may indicate that a connection error between the induction charging coil and an external energy storage device. In FIG. 24D, the warning message 1402 may indicate that an energy storage device is empty.

Figure 25:
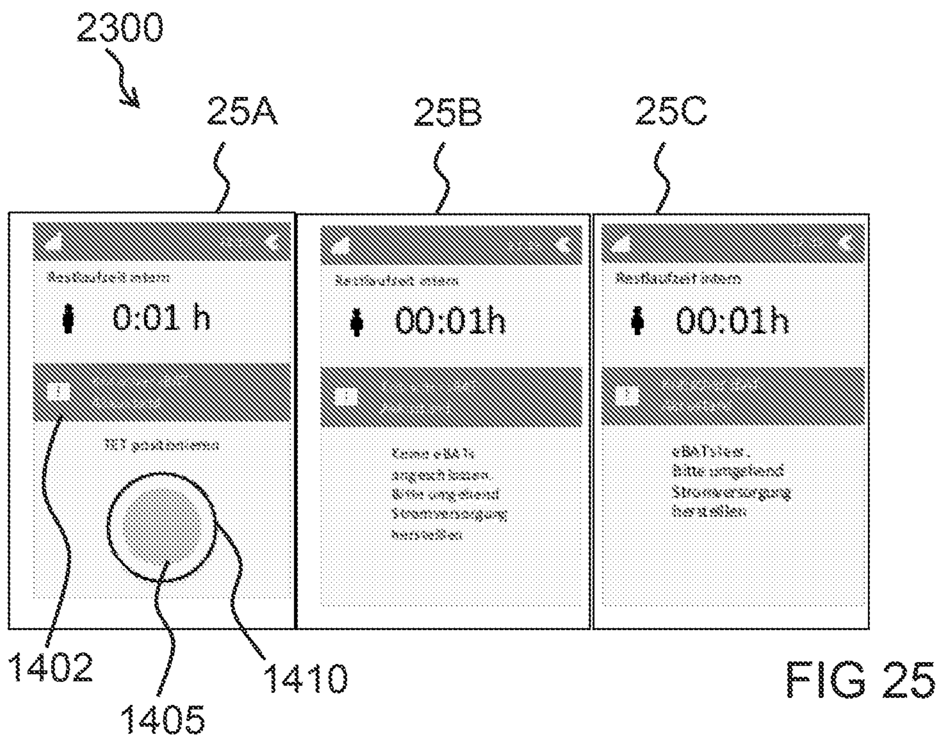
FIG. 25 shows an example of an alarm display unit.

FIG. 25 shows further example of an alarm display 2300 that may be substantially similar to the alarm display 2300 described in the previous FIGS. 23 and 24. However, the warning messages 1402 in the alarm display 2300 shown in FIG. 25 may have a high priority and be colored red. FIG.

25 is divided into three FIGS. 25A, 25B and 25C. In the example embodiment shown in FIG. 25A, the warning message 1402 may show a critical energy level of an intracorporeal energy storage device with an incorrectly positioned induction charging coil. The position of the induction charging coil is indicated by a position point 1405 in a position circle 1410. Somewhat similarly, in the example embodiment shown in FIG. 25B, the warning message 1402 may indicate a critical energy level of an intracorporeal energy storage device and a simultaneous connection error between the extracorporeal induction charging coil and an external energy storage device. The warning message 1402 in FIG. 25C may indicate a critical energy level of an intracorporeal energy storage device and may be displayed if the external energy storage is also empty.

FIGS. 23, 24, and 25 show different examples of alarm screens. The alarms, or warning messages 1402 may be colored according to priority, blue for low priority, yellow for medium priority, or red for high priority. The alarm display 2300 may also provide information about the alarm, e.g. the cause of the alarm, and how it can be resolved. The priority may change according to the urgency of the action as specified in the DIN EN ISO 60601-1-8 standard. A special case of the alarm screen is shown in the partial FIGS. 23A, 23B, 24B and 25A. This occurs when the extracorporeal induction coil is no longer positioned correctly over the intracorporeal induction coil, so that energy transfer is no longer possible. In this case, a graphical alignment aid described above in conjunction with FIG. 14 may appear.

Figure 26:
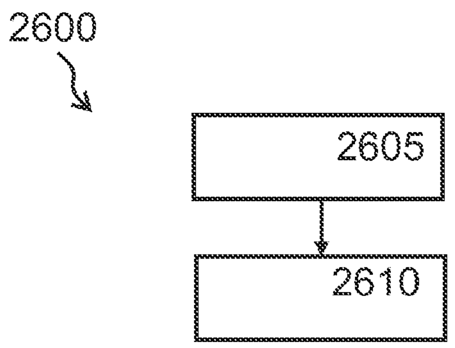
FIG. 26 shows an execution example of a procedure to transfer energy into a human body.

FIG. 26 shows an execution example of a method 2600 for transcutaneous transfer of energy into a human body. The method 2600 may include a first step 2605 of generating a magnetic field by passing an electrical current through an extracorporeal induction coil to transfer the energy to an intracorporeal induction coil and a step 2610 of providing a position signal representing a relative position between the induction charging coil and the induction coil.

Figure 27:
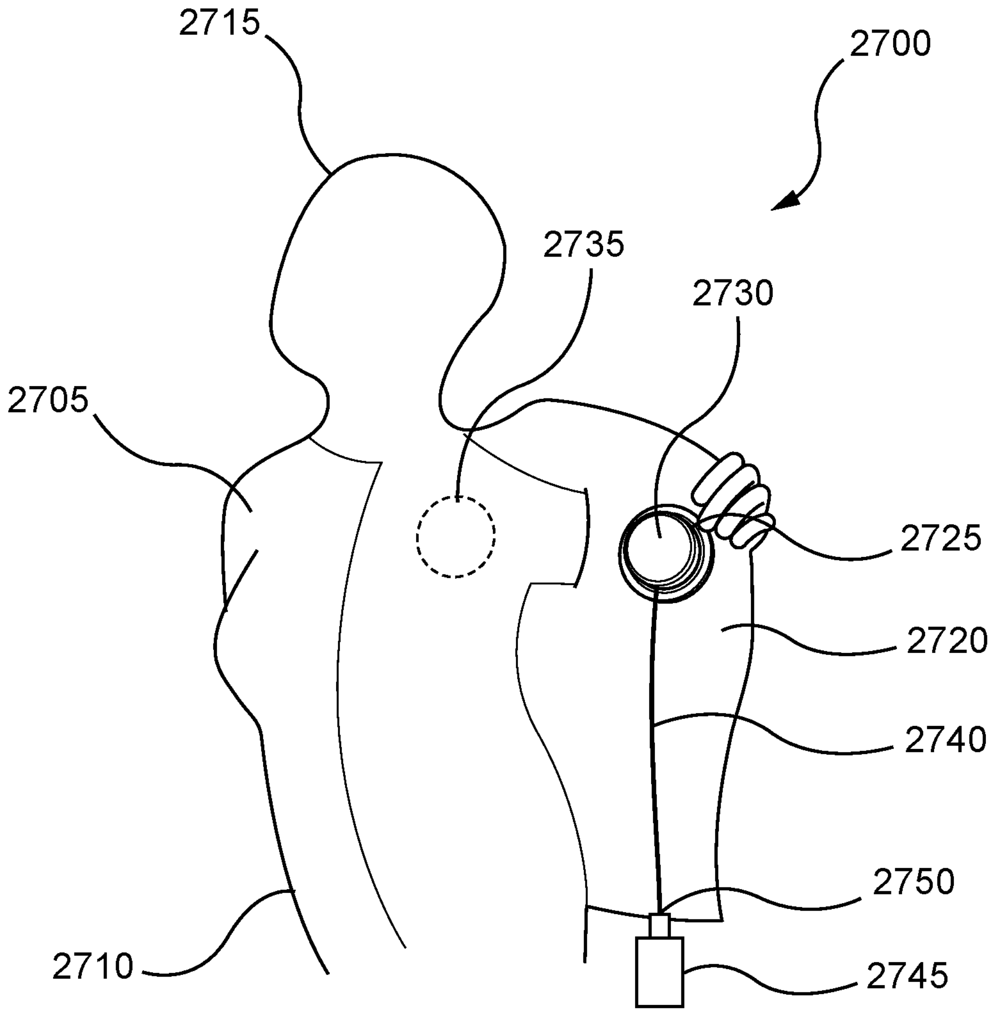
FIG. 27 shows a schematic representation of an example of a positioning device.

FIG. 27 shows a schematic representation of a positioning apparatus 2700, which may also be referred to as a carrying device or support system. Generally, the positioning apparatus 2700 may be used to transport or carry the extracorporeal components of the Cardiac Support System 100 and maintain alignment of the extracorporeal induction coil 230 with the intracorporeal induction coil 130. The positioning apparatus 2700 may take many forms and have different configurations. In this exemplary embodiment, the positioning device 2700 comprises a carrying device 2705, which may be shaped as a jacket to partially enclose a body 2710 of a patient 2715 as shown in the figure. The carrying device 2705 may comprise a receiving element 2725 disposed on a textile layer 2720 of the carrying device 2705, which corresponds to the inside of the jacket in this example.

The receiving element 2725, which may also be referred to as a mounting element, may be configured to hold or mount an extracorporeal induction coil 2730. The mounting element 2725 may be ring-shaped and designed to detachably accommodate the induction coil 2730. The mounting element 2725 may also be detachably connected to the carrying device 2705 and/or the textile layer 2720 with a hook-and-loop fastener. In some embodiments the detachable connection may be achieved by means of magnets, snap fasteners or needles. The detachable connection of the receiving element 2725 allows the induction coil 2730 to be arranged in the receiving element 2725 and positioned as needed on the body 2710. For example, the position of the extracorporeal induction coil 2730 on the carrying device 2705 may correspond with the position of an intracorporeal induction coil 2735 in the body 2710 of the patient 2715, so that when the jacket is closed, the extracorporeal induction coil 2730 is aligned with the intracorporeal induction coil 2735. To provide power to the extracorporeal induction coil, the mounting element 2725 may be connected to the electrically conductive wiring 2740, which is in turn connected to an extracorporeal component 2745 of the cardiac support system, such as a battery or control unit. The extracorporeal component 2745 may also be connected to the support system 2705 via a connecting element 2750. The battery 2745 used in this exemplary embodiment powers the wiring 2740, which powers the receiving element 2725, which finally powers the induction coil 2730. In some embodiments, the battery 2745 may power the extracorporeal induction coil 2730 directly instead of the mounting element 2725. In an example embodiment, the battery 2745 may be used to charge an internal power storage component and may be detached from the positioning apparatus 2705 when the charging is complete.

Figure 28:
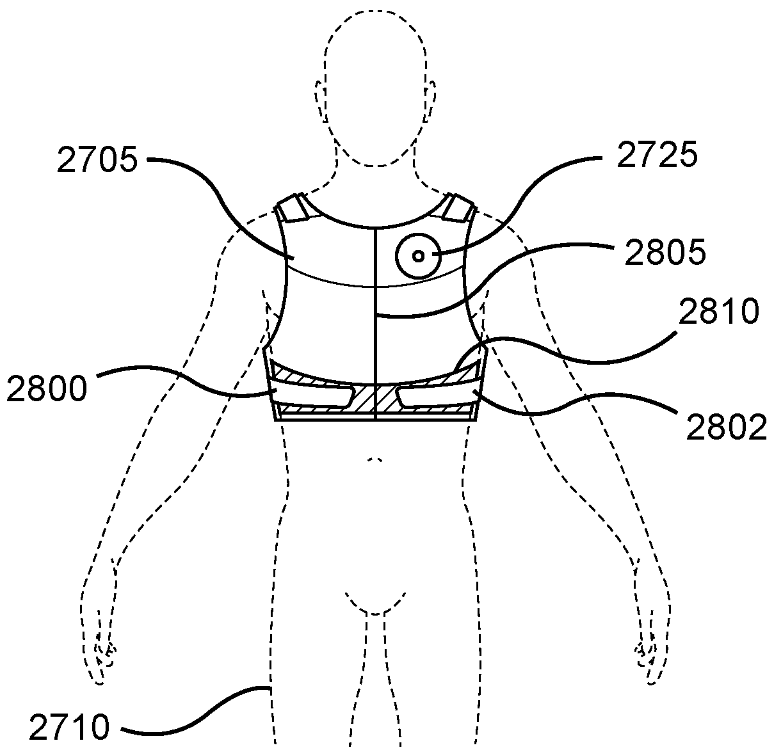
FIG. 28 shows a schematic front view of an example of a carrying device.

FIG. 28 shows a schematic front view of a carrying device 2705 that may be substantially similar to the carrying device described in FIG. 27. The carrying device 2705 shown here may further comprise a strap 2800 and a second strap 2802 for fixing the carrying device 2705 to the body 2710. As shown in FIG. 28, the carrying device 2705 may also designed as a shirt or vest. The carrying device 2705 may be relatively short on the torso of the body 2710 and may only cover an area from the shoulders to just below the chest. For easy dressing and undressing, the carrying device 2705 may include a zipper 2805. In some embodiments, the straps 2800 and 2802 may pass over the shoulders and cross over one another on the back of the body. The straps 2800 and 2802 may be led to the front of the body 2710 again and fastened to the carrying device 2705 by means of a hook-and-loop or a hook-and-loop fastener counterpart 2810. In some embodiments, the straps 2800 and 2802 may be fastened using a mechanical fastener, such as a snap fastener or buckle, or other fastening means.

Figure 29:
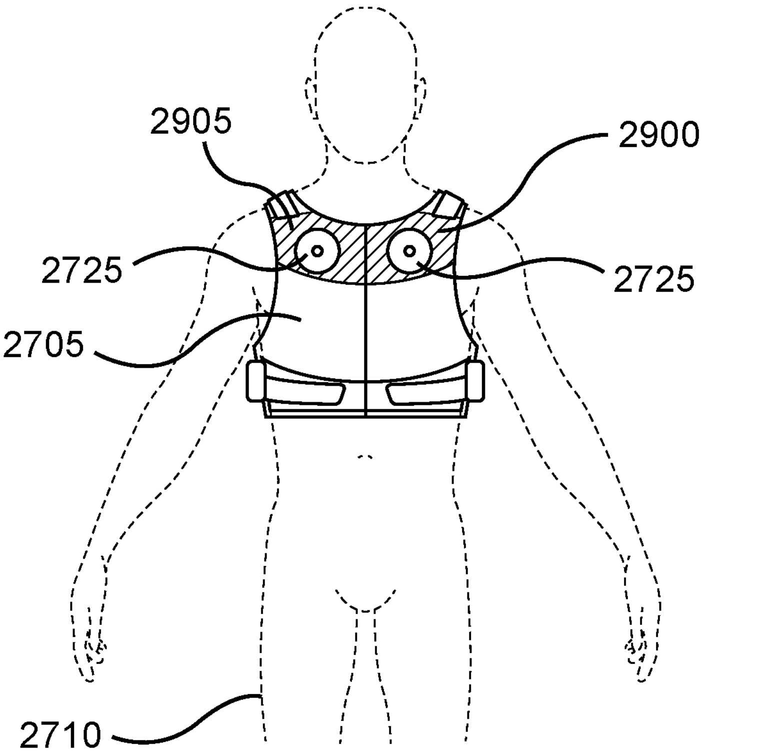
FIG. 29 shows a schematic front view of an example of a carrying device.

FIG. 29 shows a schematic front view of an example of a carrying device 2705. The carrying device 2705 may be substantially similar to the carrying devices described in previous figures. The carrying device 2705 shown here may further comprise a first fixing element 2900 for releasably fixing a receiving element 2725 comprising a second fixing element. The first fixing element 2900 may be arranged in a top right-hand corner of the supporting device 2705 and may comprise a hook-and-loop fastener material. In another design example, the first fixing element 2900 may be a magnet, a plurality of snap fasteners, an adhesive, or a sewn attachment. In this design example, a second fixing element 2905 is located in a top left corner and may be symmetrically positioned relative to the first fusing element 2900. In some embodiments, the entire inside of the carrying device 2705 may be designed to hold a mounting element 2725 in place. For example, large areas of hook-and-loop-compatible material may be disposed on the inside of the carrying device 2705.

Figure 30:
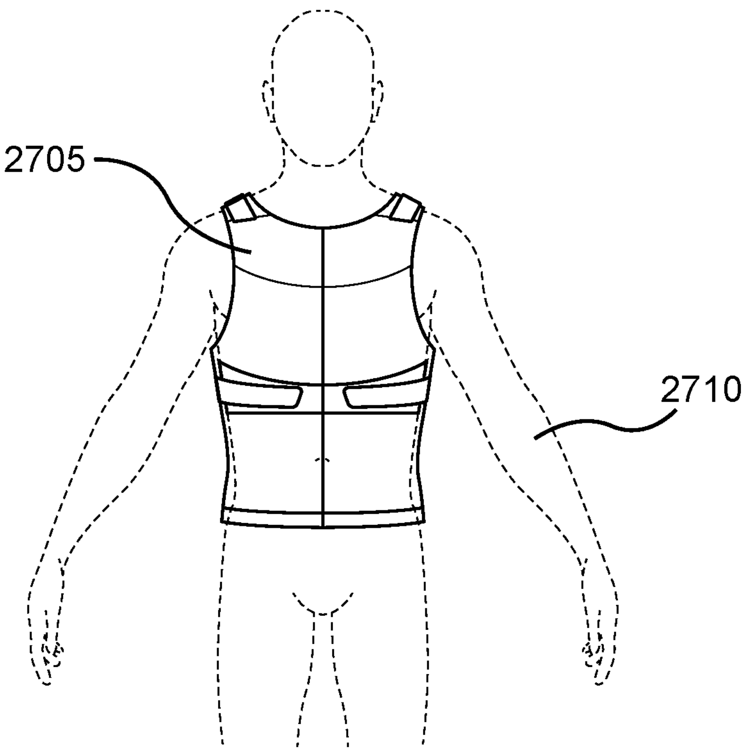
FIG. 30 shows a schematic front view of an example of a carrying device.

FIG. 30 shows a schematic front view of another example of a carrying device 2705. The carrying device 2705 shown here corresponds or resembles the carrying device described in the previous figures, with the difference that the carrying device 2705 shown here is longer and extends from the shoulders to the hips of body 2710.

Figure 31:
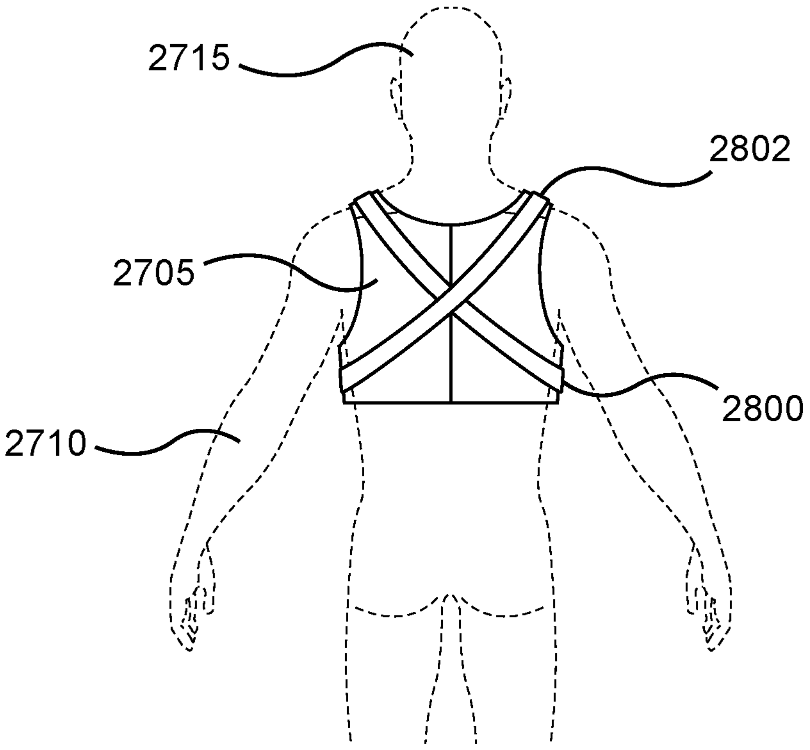
FIG. 31 shows a schematic rear view of an example of a carrying device.

FIG. 31 shows a schematic rear view of another example of a carrying device 2705. The carrying device 2705 shown here corresponds or resembles the carrying device described in the previous figures. As shown in FIG. 31 and described above, the first strap 2800 and the second strap 2802 may pass over the shoulders, cross over each on the back of the body 2710, and be attached to the carrying device 2705 at the side of the body 2710.

Figure 32:
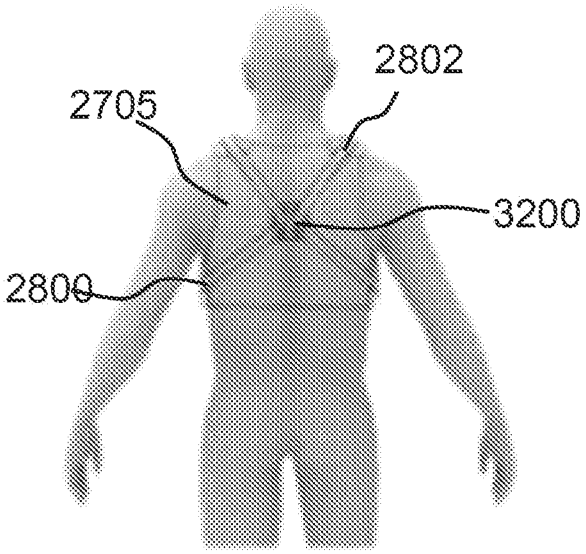
FIG. 32 shows a schematic rear view of an example of a carrying device.

FIG. 32 shows a schematic rear view of an example of a carrying device 2705. The carrying device 2705 shown here corresponds to or is similar to the carrying device described in the previous figures. In this embodiment, the first strap 2800 and the second strap 2802 may be attached to the carrying device 2705 the same side of body 2710 that they originate from unlike in FIG. 31. The straps 2800 and 2802 may pass over the shoulders, through a central eyelet 3200, and attach to the bottom of the carrying device 2705 as shown in FIG. 32.

Figure 33:
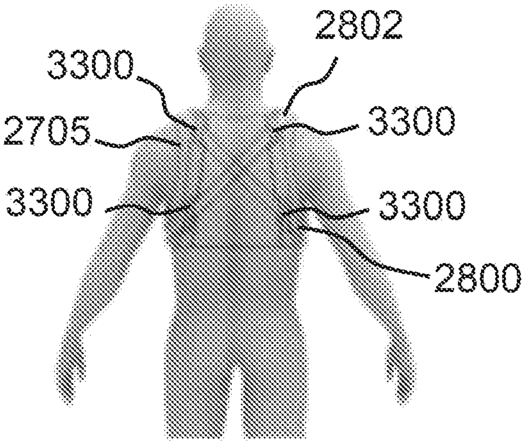
FIG. 33 shows a schematic rear view of an example of a carrying device.

FIG. 33 shows a schematic rear view of an embodiment of a carrying device 2705. The carrying device 2705 shown here may resemble the carrying device described in the previous figures. In this example, the first strap 2800 and the second strap 2802 may cross over four lateral eyelets 3300.

Figure 34:
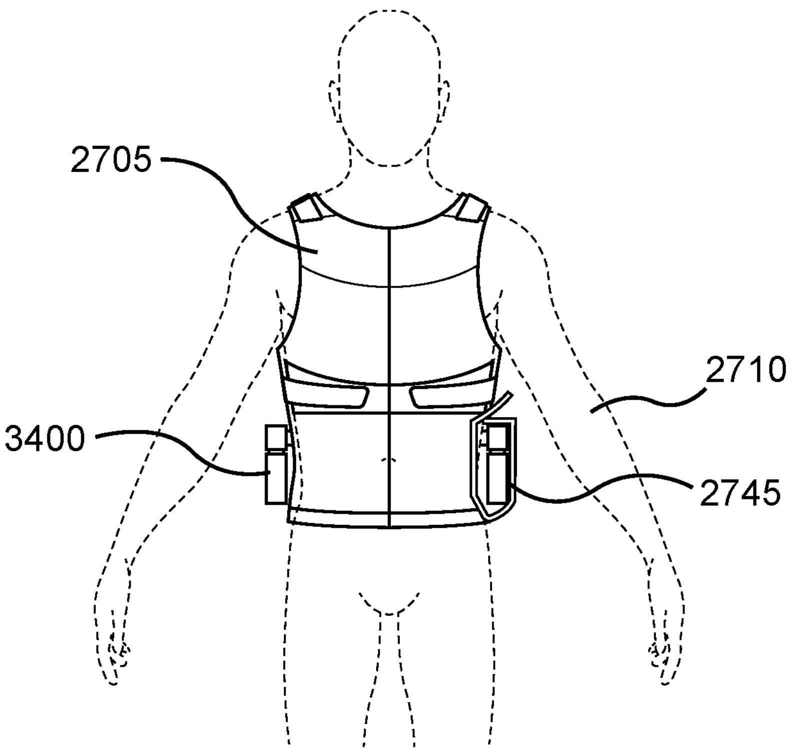
FIG. 34 shows a schematic front view of an example of a carrying device.

FIG. 34 shows a schematic front view of another example of a carrying device 2705. As shown in FIG. 34, an extracorporeal component 2745, a battery for example, may be arranged on the carrying device 2705. Another component 3400, such as a control unit, may also be attached to the carrying device 2705. As shown in FIG. 34, the extracorporeal components 2745 and 3400 may be arranged on the side of the body 2710. However, the components 2745 and 3400 may be disposed anywhere on the carrying device 2705. For example, the components 2745 and 3400 may be placed on the chest or back of the body 2710.

Figure 35:
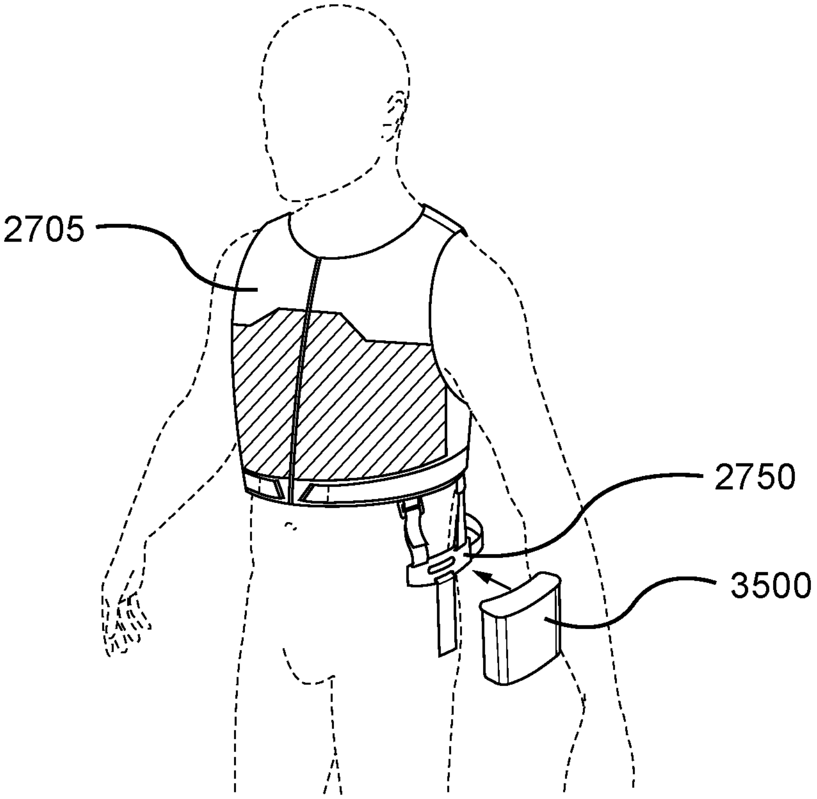
FIG. 35 shows a diagonal side view of an example of a carrying device.

FIG. 35 shows an oblique side view of an example of a carrying device 2705. The carrying device 2705 shown here further comprises a pocket 3500 for holding an extracorporeal component. The pocket 3500 may be detachably connected to the carrying device 2705 via a connecting element 2750. The connecting element 2750 may be a mechanical fastener, a strap, hook-and-loop fasteners, a magnet, or other connecting means.

Figure 36:
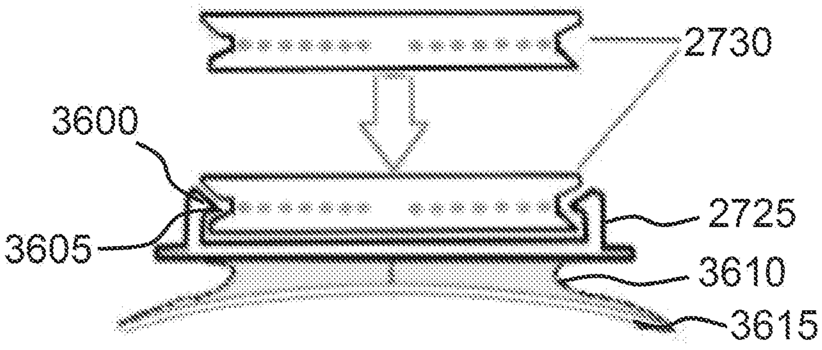
FIG. 36 shows a cross-sectional representation of an example of an acquisition element.

FIG. 36 shows a cross-sectional representation of an example of a receiving element 2725 configured to mount or hold an extracorporeal induction coil 2730. The mounting element 2725 shown here corresponds or resembles the mounting element described in FIG. 1. As shown in FIG. 36, the mounting element 2725 may be shaped like a ring and include a circumferential projection 3600. The projection 3600 may be configured to fit into a circumferential recess 3605 when the induction coil 2730 is placed into the holding element 2725. The holding element 2725, which can also be described as a holding ring, may be made of a relatively strong, semi-flexible material, such as a plastic. Further, the holding element 2725 may be mounted on a connecting foil 3610 comprised of a very soft and flexible material. In this example, the connecting foil 3610 may connect or pair the receiving element 2725 and a second fixing element 3615. The second fixing element 3615 may be configured to be attached to the carrying device 2705 or the body 2710. For example, the second fixing element 3615 may be an adhesive layer or a hook-and-loop material. By means of the second fixing element 3615, the mounting element 2725 can be fixed to a support device comprising a corresponding first fixing element as described in the previous figures. In some embodiments, the mounting element 2725 may be directly attached to the carrying apparatus 2705 without the second fixing element 3615.

Figure 37:
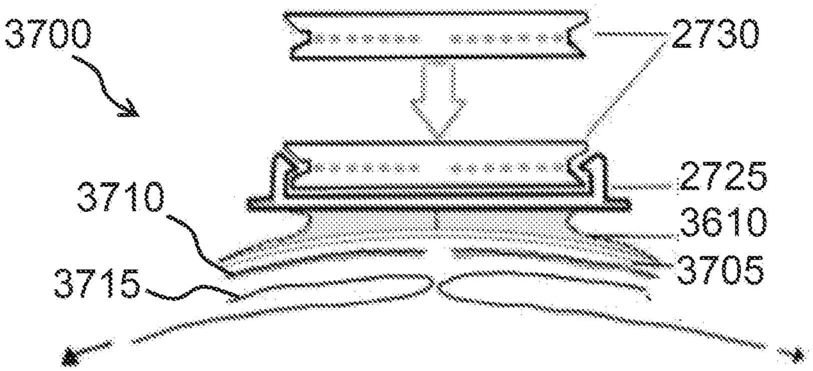
FIG. 37 shows a cross-sectional representation of an example of a locating element as part of a positioning patch.

FIG. 37 shows a cross-sectional view of an execution example of a receiving element 2725 that further comprises a positioning plaster 3700. The mounting element 2725 shown here may resemble the insertion element described in FIGS. 27 and 36. As shown in FIG. 37, the insertion element 2725 may further comprise a positioning patch 3700, which may be referred to in some places as a positioning plaster. The positioning patch 3700 may include a multilayer structure. The receiving element 2725 may be connected to a carrier layer 3705 via a connecting film 3610. The carrier layer 3705 may be made of flexible material and adapt to different positions and body curvatures. The connecting foil 3610 may compensate between different shapes of the carrier layer 3705 and the receiving element 2725 in some embodiments. On the side of the carrier layer 3705 opposite the receiving element 2725, an adhesive 3710 may be applied to adhere the carrier layer 3705 to the skin of a patient. The adhesive 3710 may be covered by a two-part and double-folded protective film 3715. In this example, the protective film 3715 is designed to protect the adhesive 3710 and allow the positioning patch 3700 to be moved on a patient's body until the extracorporeal induction coil 2730 is in the correct position for energy transfer.

Figure 38:
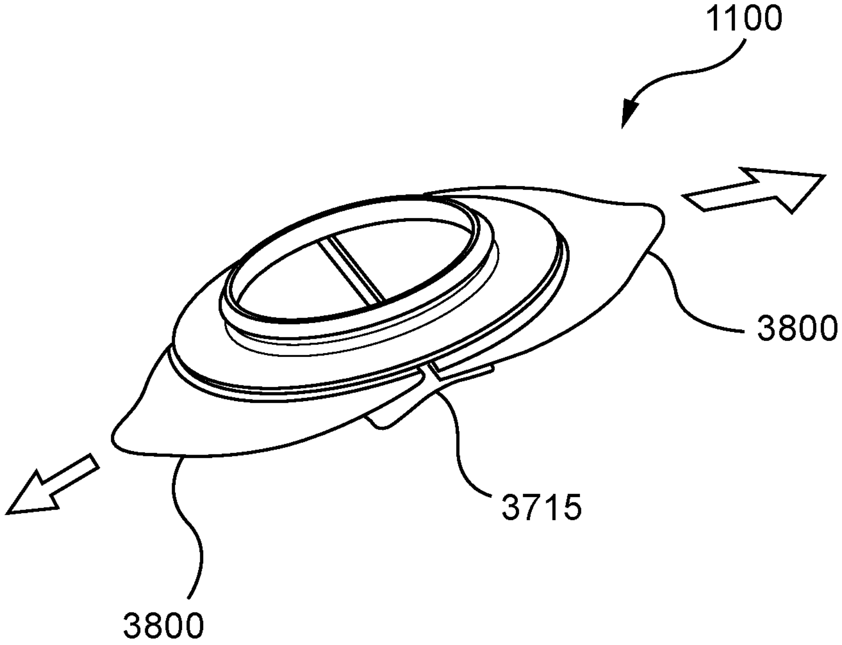
FIG. 38 shows a perspective top view of an example of a positioning patch.

FIG. 38 shows a top view of the positioning patch 3700. The positioning patch 3700 resembles the positioning plaster described in FIG. 37. As discussed above, the protective film 3715 may include tabs 3800 that may be removed laterally to expose the adhesive layer 3710.

Figure 39:
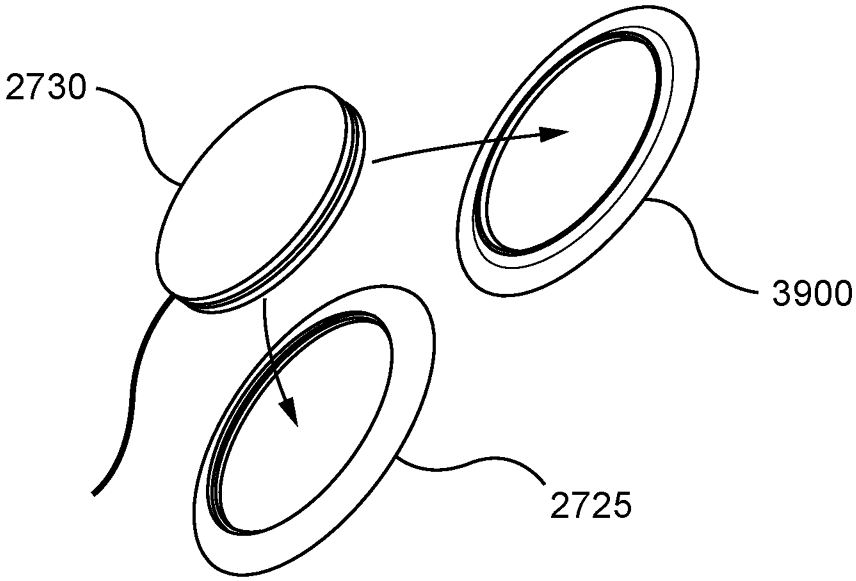
FIG. 39 shows a perspective top view of an example of one or more recording elements.

FIG. 39 shows an oblique top view of a design example of a mounting element 2725 and a second mounting element 3900. The mounting element 2725 corresponds to or is similar to the receiving element described in FIGS. 27, 36 and 37. As discussed above, a hook-and-loop fastener can be fixed to a carrying device. In this illustration, the mounting element 3900 is another exemplary design of the receiving element 2725 and corresponds to it in shape and size, but it is designed to be glued directly to a body. The induction coil 2730 may fit in in the mounting element 2725 and the second mounting element 3900.

Figure 40:
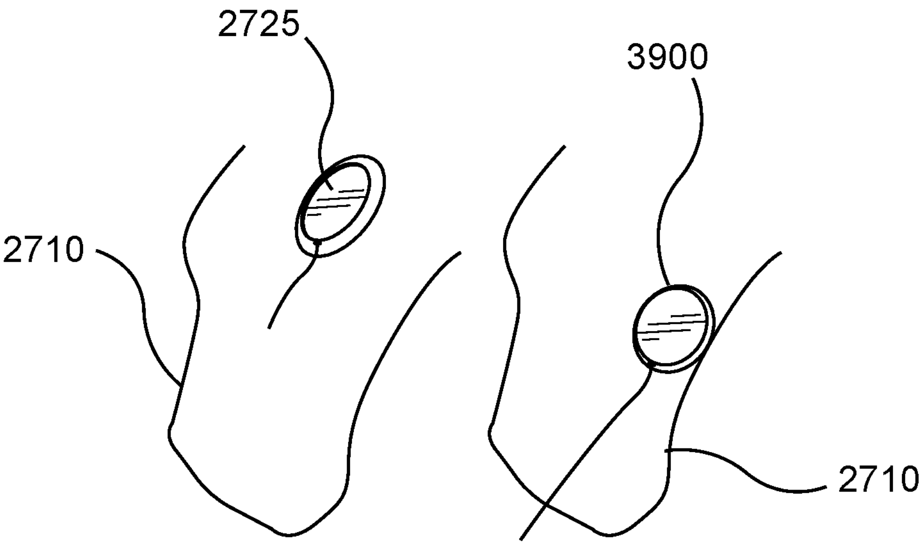
FIG. 40 shows a schematic representation of an example of one or more pick-up element.

FIG. 40 shows a schematic representation of an example of the mounting element 2725 and the second mounting element 3900. In this example, the receiving element 2725 and the second receiving element 3900 may be glued directly onto a body 2710. The first mounting element 2725 may be disposed on an upper portion of body 2710 while the second mounting element 3900 may be disposed on a lower portion of body 2710. The positioning of the receiving element 2725 and/or the second receiving element 3900 depends on the position of an intracorporeal induction coil as described above in conjunction with FIG. 27.

Figure 41:
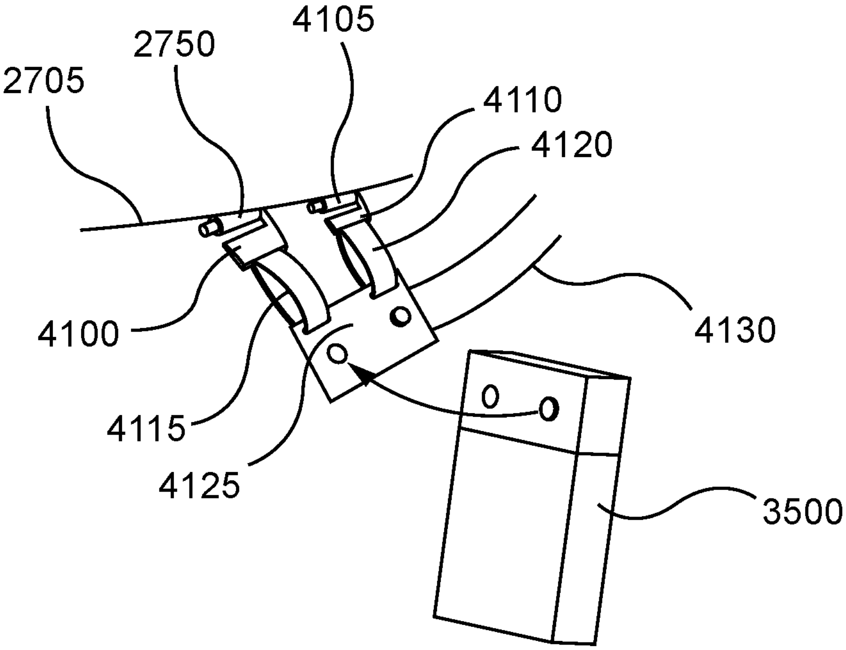
FIG. 41 shows a schematic representation of an example of a connecting element with a retaining element.

FIG. 41 shows a schematic representation of an example of a fastener 2750 comprising a retaining element 4100. The fastener 2750 shown here corresponds to or is similar to the one described in the FIGS. 27 and 35. The connecting element 2750 may be formed as an eyelet and firmly connected to the carrying device 2705. In addition to the connecting element 2750, the supporting device 2705 may further comprise a connecting element 4105 that corresponds to the connecting element 2750. As shown in FIG. 41, the connecting element 2750 may be connected to the retaining element 4100, which may be hook-shaped. As shown in FIG. 41, the hook-shaped retaining element 4100 may be inserted through a corresponding loop-shape of the connecting element 4105 of the carrying device 2705. In another design example, the retaining element 4100 may be designed with hook-and-loop fasteners, press studs, magnets or sewn. The retaining element 4100 can also be designed as a buckle, clip, or another mechanical fastener. The retaining element 4100 and the second retaining element 4110 may be connected to a carrier plate 4125 via a length-adjustable belts 4115 and 4120, respectively. The carrier plate 4125 may also be referred to as an adapter and configured to receive different extracorporeal components of the cardiac support system 100. In some embodiments, a bag 3500 for holding an extracorporeal component can be attached to the support device 2705 via the support plate 4125. In this example, an additional belt 4130 may run from the support plate 4125 over the back of a patient (not shown here) and connected to a second carrier plate attached to the other side of the patient, so that the hardware fits more securely to the body and does not wobble. In some embodiments, the bag 3500 can be attached without the additional belt 4130.

Figure 42:
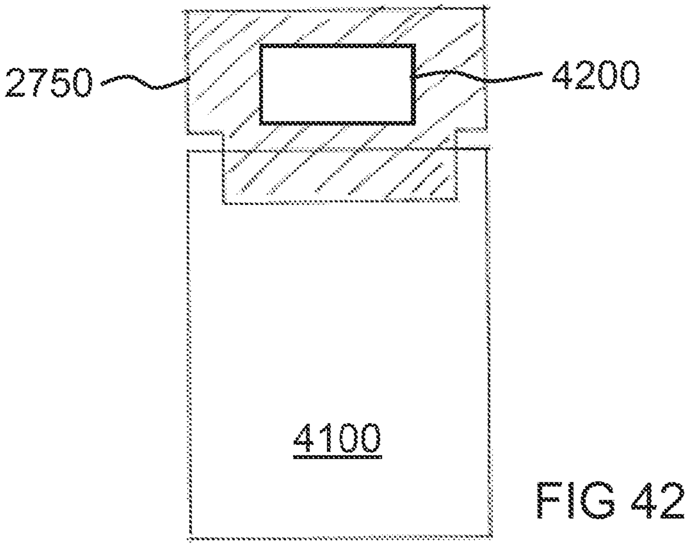
FIG. 42 shows a schematic representation of an example of a connecting element with a retaining element.

FIG. 42 shows a schematic representation of an example of a fastener 2750 and a retaining element 4100. The connecting element 2750 shown here may correspond with or resemble the connecting element described in the previous FIGS. 27, 35 and 41. As discussed above, the connecting element 2750 may be a mechanical fastener. For example, the connecting element 2750 may be a snap-fit fastener that comprises a receiving component and an insertion component, that may be interchangeably attached to the carrying device or an extracorporeal component of the cardiac support system 100. Further the carrying element 2750 may be configured to retain an extracorporeal component of the Cardiac Support System 100. In the example shown if FIG. 42, the connecting element 2750 is configured to retain a control unit 4200 and can be inserted into the retaining element 4100.

Figure 43:
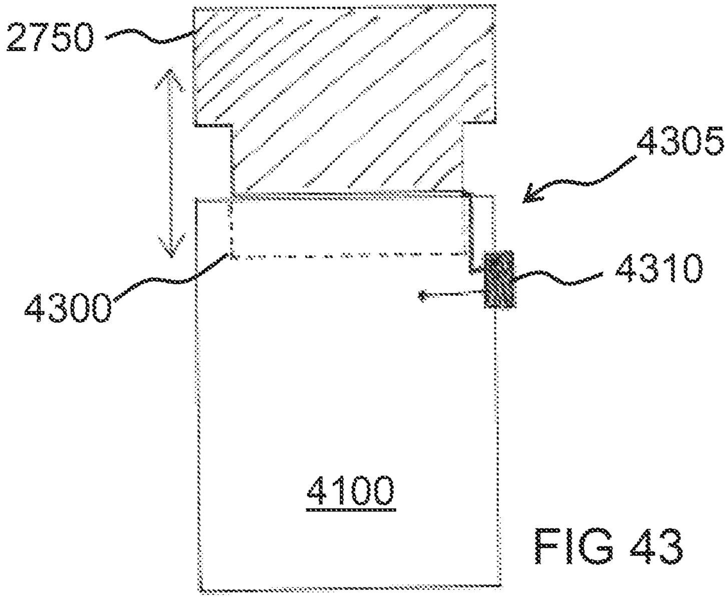
FIG. 43 shows a schematic representation of an example of a connecting element with a retaining element.

FIG. 43 shows a schematic representation of an example of a connecting element 2750 with a retaining element 4100. The connecting element 2750 and the retaining element 4100 shown here may correspond with or resemble those described in the previous FIGS. 27, 35, 41 and 42. In this design example, the connecting element 2750 can be pushed into the retaining element 4100 from above and be secured in a vertical groove 4300. The retaining element 4100 may include a mechanical spring mechanism 4305 that is designed to hold the connecting element 2750. The spring mechanism 4305 may be pushed back first and then snap into a final position so that the connecting element 2750 is held in place. In some embodiments, the connecting element may further comprise a recess or groove to receive the spring mechanism 4305. The retaining element may also include a release button 4310, which can be reached from the outside, to release the connecting element 2750 from retaining element 4100 when the appropriate pressure is applied.

Figure 44:
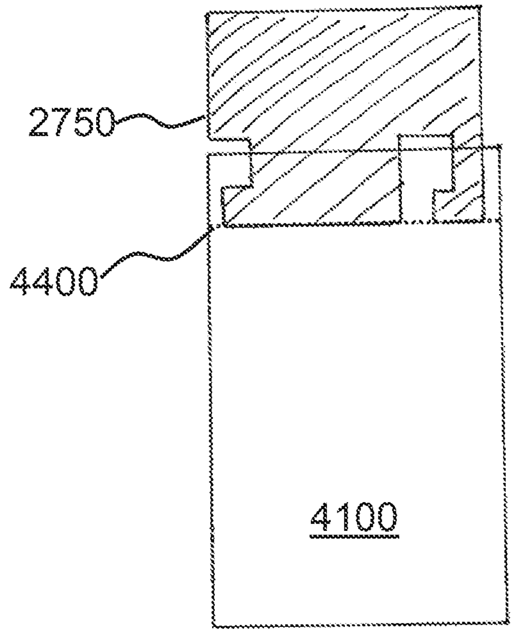
FIG. 44 shows a schematic representation of an example of a fastener with a retaining element.

FIG. 44 shows a schematic representation of an example of a connecting element 2750 with a retaining element 4100. The connecting element 2750 and the retaining element 4100 shown here may correspond or resemble those described in the previous FIGS. 27, 35, 41, 42 and 43. The retaining element 4100 in this design example also includes a horizontal groove 4400, which is formed at defined points with an open profile, to receive and secure the connecting element 2750 when it is inserted into the retaining element 4100.

Figure 45:
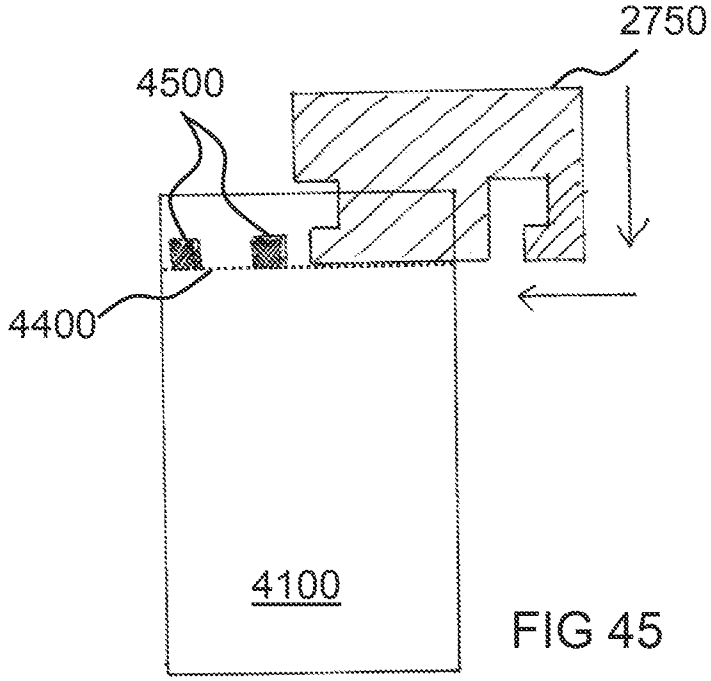
FIG. 45 shows a schematic representation of an example of a connecting element with a retaining element.

FIG. 45 shows a schematic representation of a connecting element 2750 with a retaining element 4100. The connecting element 2750 and retaining element 4100 shown here may correspond with or resemble the connecting and retaining element described in the previous FIGS. 27, 35, 41, 42, 43 and 44. The retaining element 4100 in this design example includes a horizontal groove 4400 with two magnets 4500 to secure the lock. The retaining element 4100 may be designed to receive the connecting element 2750 laterally and hold the connecting element 2750 in place using magnetic force. The magnetic force may prevent slipping or accidental displacement. The magnetic connection may allow the connecting unit 2750 to be released with relatively little force. As discussed above, other locking variants may be used. For example, sliders, mechanical design variants with basic mechanical clips, snap fasteners, or hook-and-loop fasteners can be used. Other magnetic designs may also be used, e.g. using electromagnets or purely magnetic solutions.

Figure 46:
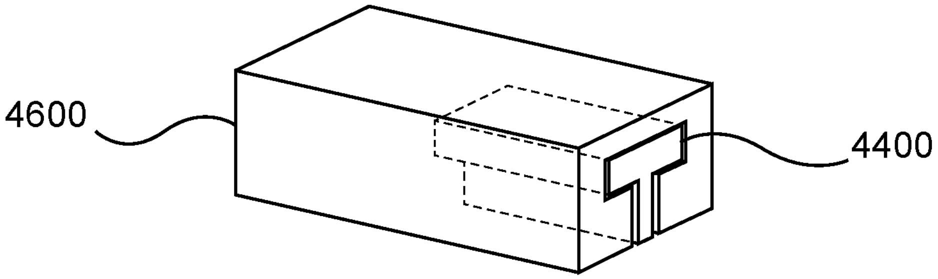
FIG. 46 shows a schematic representation of an example of a connection unit.

FIG. 46 shows a schematic representation of an example of a retaining unit 4600 for connecting a connecting element 2750 to the retaining element 4600. As shown in FIG. 46, the connection unit 4600 may include a horizontal groove 4400 for lateral insertion of a connecting element 2750, which includes a corresponding tongue feature.

Figure 47:
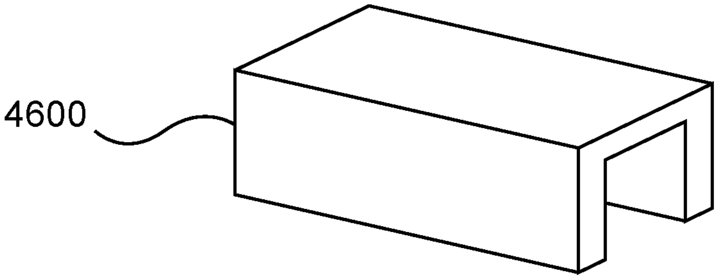
FIG. 47 shows a schematic representation of an example of a connection unit.

FIG. 47 shows a schematic representation of an embodiment of a retaining unit 4600. The retaining unit 4600 may be similar to the retaining unit described in FIG. 46, and further comprise an open profile.

Figure 48:
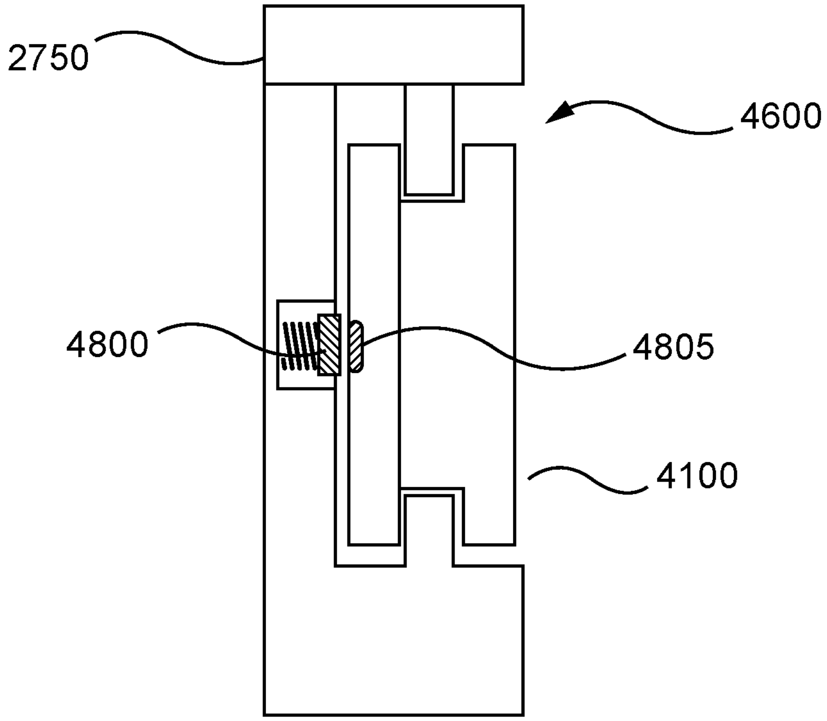
FIG. 48 shows a schematic representation of an example of a connection unit.

FIG. 48 shows a schematic representation of another example of a retaining unit 4600. The retaining unit 4600 corresponds or is similar to the connector unit described in the previous FIGS. 46 and 47. As shown in FIG. 48, the retaining unit 4600 may also include an electrical contact element 4805. Accordingly, the connecting element 2750 may also include an electrical contact element 4800. The electrical contact element 4800 of the connecting element 2750 may be designed as a spring contact to compensate tolerances and ensure constant pressure and contact with the electrical contact 4805 of the retaining element 4600. The contact element 4805 may correspond in shape to the electrical contact element 4800. The electrical contact element 4805 may be arranged adjacent to the electrical contact element 4800 in the operational state. When the electrical contact devices 4800 and 4805 are connected, a current flow or transmission of electrical signals between the components of the Cardiac Support System 100 that are attached to the connecting element 2750 and the retaining element 4600 may be achieved. For example, a control unit 205 may be attached to the connecting element 2750. When the connecting element 2750 is attached to the retaining element 4600, an electrical connection may be established between the control unit 205 and other components of the Cardiac Support System 100, such as a display device 240 or an external battery.

Figure 49:
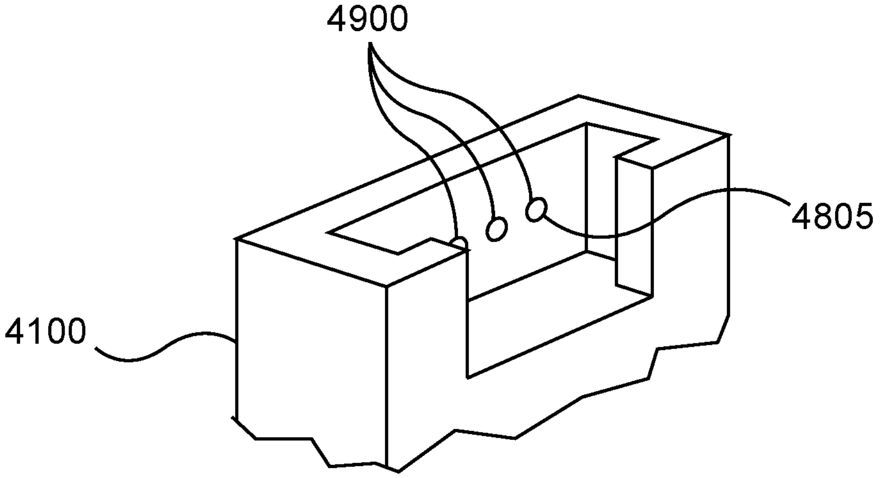
FIG. 49 shows a schematic representation of an example of a retaining element with a mating contact element.

FIG. 49 shows a schematic diagram of an example of a retaining element 4600 with the electrical contact element 4805. The retaining element 4600 may comprise the electrical contact element 4805 with three sub-contacts 4900, or contact points.

Figure 50:
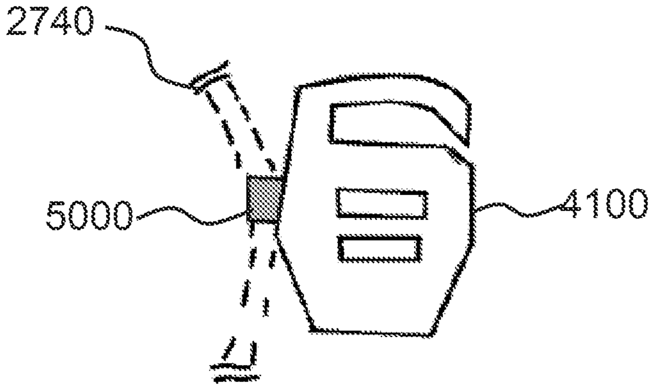
FIG. 50 shows a schematic representation of an example of a retaining element.

FIG. 50 shows a schematic representation of an exemplary embodiment of a retaining element 4100. The retaining element 4100 may be substantially similar to the retaining element described in the previous FIGS. 41 through 49. As shown in FIG. 50, the retaining element 4100 may further include a cable holder 5000 for guiding a cable 2740. The cable holder 5000 may be arranged on the side of the retaining element 4100 or in another location depending on the retaining element's shape. The cable holder 5000 may be mechanical fastener, hook-and-loop fastener, or the like.

Figure 51:
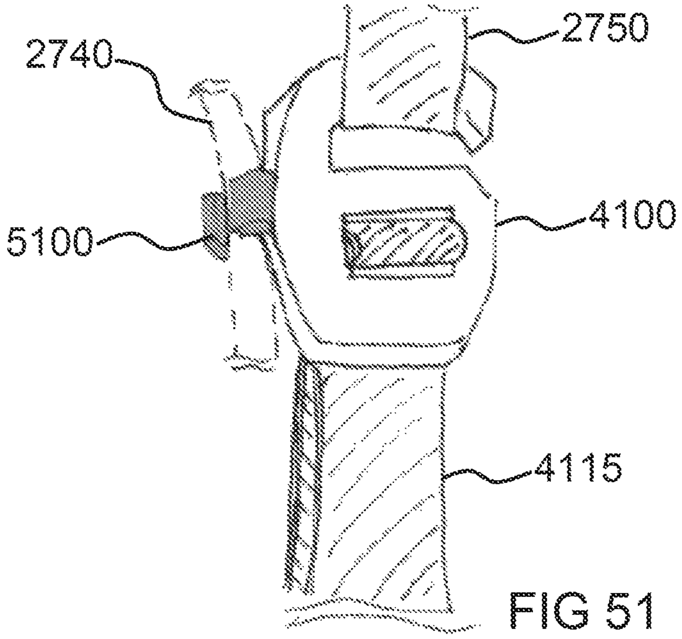
FIG. 51 shows a schematic representation of an example of a retaining element.
Figure 52:
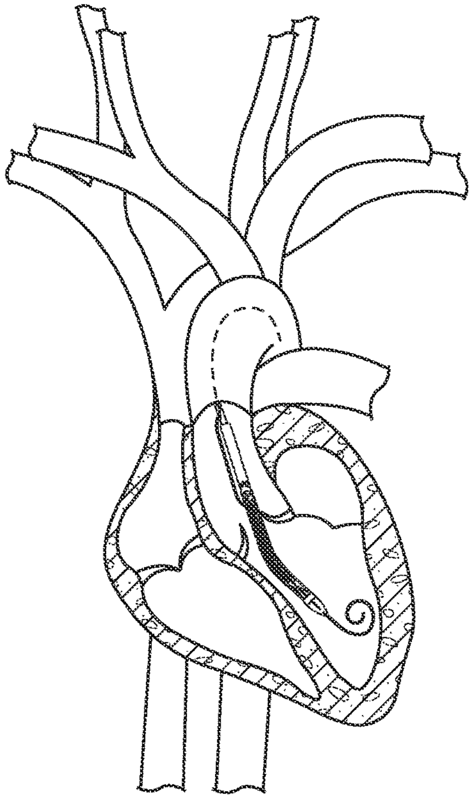
FIG. 52 shows an illustration of an access pathway from the femoral artery to the left ventricle.

FIG. 51 shows a schematic representation of another example of a retaining element 4100. In the illustration, the retaining element 4100 may be a ladder buckle with a hook that is hooked into a connecting element 2750, which may be a corresponding loop or eyelet. The retaining element 4100 may also include a strap 4115 for attaching a bag as shown in FIG. 35 and FIG. 41.

The Cardiac Support System 100 may also be referred to as Mechanical Circulatory Support (MCS) system. The MSC system includes a temporary (generally no more than about 6 hours) left ventricular support device for use during high-risk percutaneous coronary intervention (PCI) performed in elective or urgent, hemodynamically stable patients with severe coronary artery disease and/or depressed left ventricular ejection fraction, when a heart team, including a cardiac surgeon, has determined high risk PCI is the appropriate therapeutic option. It is placed across the aortic valve via a single femoral arterial access.

The system may include a low-profile axial rotary blood pump mounted on a catheter such as an 8 Fr catheter, referred to as an MCS pump or MCS device. When in place, the MCS pump can be driven by an MCS controller to provide up to about 4.0 liters/minute of partial left ventricular support, at about 60 mmHg. No system purging is needed due to improved bearing design and sealed motor, and the system is visualized fluoroscopically eliminating the need for placement using sensors.

The system may further include an expandable sheath, which allows 8-10 Fr initial access size for easy insertion and closing, expandable to allow introduction of 14 Fr and 18 Fr pump devices and return to a narrower diameter around the 8 Fr catheter once the pump has passed. This feature may allow passage of the heart pump through vasculature while minimizing shear force within the blood vessel, advantageously reducing risk of bleeding and healing complications. Distention or stretching of an arteriotomy may be done with radial stretching with minimal shear, which is less harmful to the vessel. Access may be accomplished via transfemoral, transaxillary, transaortal, or transapical approach.

Figure 53:
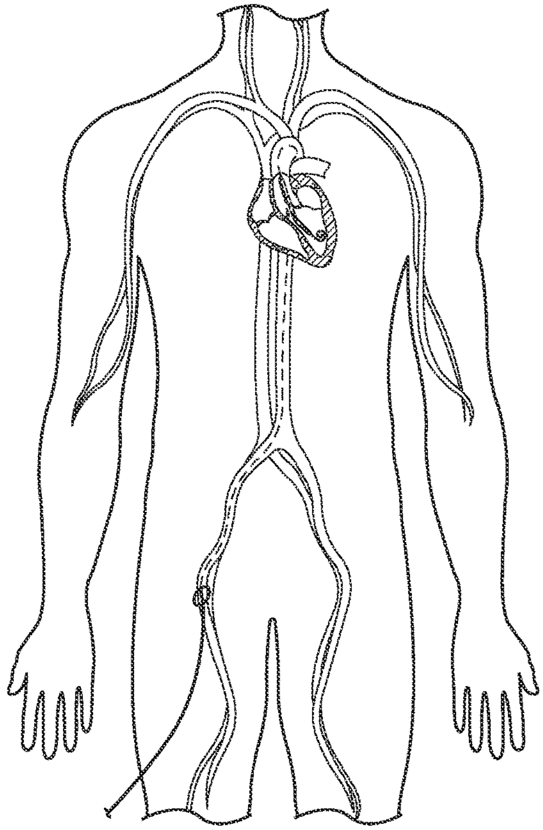
FIG. 53 shows a cross sectional rendering of an example Mechanical Circulatory Support (MCS) device mounted on a catheter and positioned across an aortic valve via a femoral artery access.

FIG. 53 shows a rendering of the MCS device mounted on the tip of an 8 Fr catheter. An inlet tube portion of the device extends across the aortic valve. The impeller is located at the outflow section of the inlet tube drawing blood from the left ventricle and ejecting it into the ascending aorta. The motor is mounted directly proximal to the impeller in a sealed housing eliminating the need to flush the motor prior to or during use. This configuration provides hemodynamic support during high-risk PCI, time and safety for a complete revascularization via a minimally invasive approach (rather than an open surgical procedure).

The system has been designed to eliminate the need for motor flushing, provide increased flow performance up to 4.0 l/min at 60 mmHg with acceptably safe hemolysis due to a computational fluid dynamics (CFD) optimized impeller that minimizes shear stress.

Figure 54:
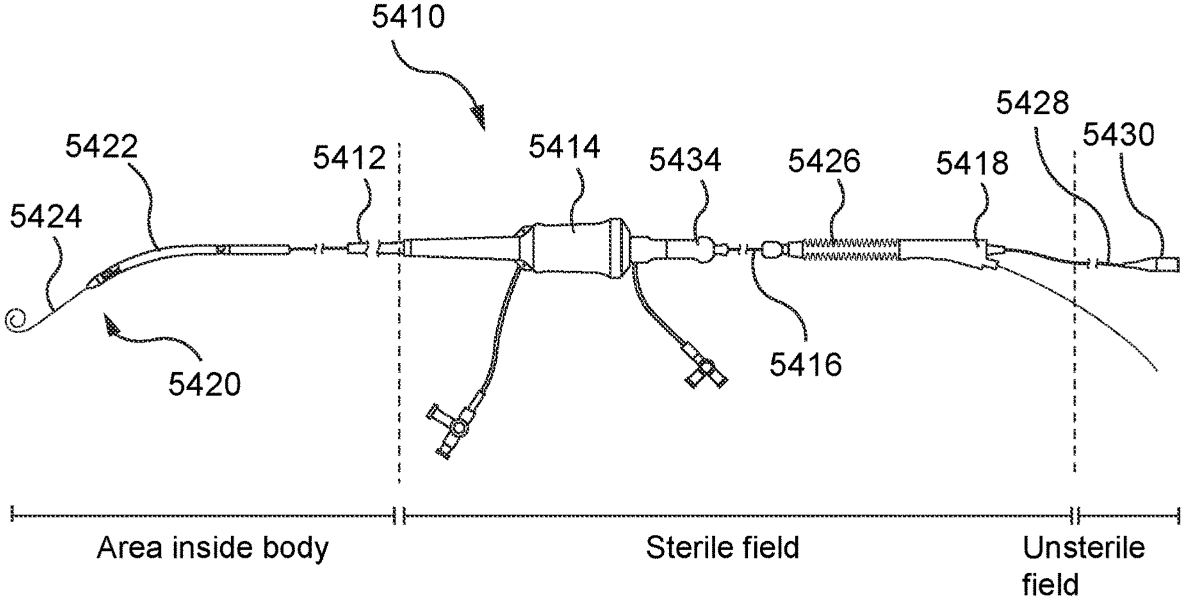
FIG. 54 is a side elevational view of a mechanical circulatory support system.

The device actively unloads the left ventricle by pumping blood from the ventricle into the ascending aorta and systemic circulation (shown in FIGS. 53 and 54). When in place, the MCS device can be driven by the complementary MCS Controller to provide between 0.4 l/min up to 4.0 l/min of partial left ventricular support.

In general, the overall MCS system includes a series of related subsystems and accessories, including the following:

The MCS Device including pump, shaft, proximal hub, insertion tool, proximal cable, infection shield and guidewire aid. The MCS Device is provided sterile.

The MCS shaft contains the electrical cables and a guidewire lumen for over-the-wire insertion.

The proximal hub contains guidewire outlet with a valve to maintain hemostasis and connects the MCS shaft to the proximal cable, that connects the MCS Device to the MCS Controller.

The proximal cable is 3.5 m (approx. 177 inch) in length and extends from the sterile field to the non-sterile field where the MCS Controller is located.

A MCS insertion tool as part of the MCS Device to facilitate the insertion of the pump into the Introducer Sheath and to protect the inlet tube and the valves from potential damage or interference when passing through the Introducer Sheath.

A peel-away guidewire aid pre-mounted on the MCS Device to facilitate the insertion of the 0.018" placement guidewire into the pump and into the MCS shaft.

A 3 m 0.018" placement guidewire, having a soft coiled pre-shaped tip for atraumatic wire placement into the left ventricle. The guidewire is provided sterile.

A 14 Fr Introducer Sheath with a usable length of 275 mm to maintain access into the femoral artery and provide hemostasis for the 0.035" guidewire, the diagnostic catheters, the 0.018" placement guidewire, and the insertion tool. The housing of the Introducer Sheath is designed to accommodate the MCS Insertion Tool. The Introducer Sheath is provided sterile.

An introducer dilator compatible with the Introducer Sheath to facilitate atraumatic insertion of the Introducer Sheath into the femoral artery. The introducer dilator is provided sterile.

An MCS Controller which drives and operates the MCS Device, observes its performance and condition as well as providing error and status information. The powered controller is designed to support at least about 12 hours of continuous operation and contains a basic interface to indicate and adjust the level of support provided to the patient. Moreover, the controller provides an optical and audible alarm notification in case the system detects an error during operation. The MCS Controller is provided non-sterile and is contained in an enclosure designed for cleaning and re-use outside of the sterile field. The controller enclosure contains a socket into which the extension cable is plugged.

Referring to FIG. 54, there is illustrated an overall MCS system 5500, subcomponents of which will be described in greater detail below. The system 5410 includes an introducer sheath 5412 having a proximal introducer hub 5414 with a central lumen for axially movably receiving an MCS shaft 5416. The MCS shaft 5416 extends between a proximal hub 5418 and a distal end 5420. The hub 5418 may be provided with an integrated Microcontroller or memory storage device for device identification and tracking of the running time, which could be used to prevent overuse to avoid excessive wear or other technical malfunction. The microcontroller or memory device could disable the device, for example to prevent using a used device. They could communicate with the controller, which could display information about the device or messages about its usage. An atraumatic cannula tip with radiopaque material allows the implantation/explanation to be visible under fluoroscopy.

A pump 5422 is carried by a distal region of the MCS shaft 5416. The system 5410 is provided with at least one central lumen for axially movably receiving a guide wire 5424. The proximal hub 5418 is additionally provided with an infection shield 5426. A proximal cable 5428 extends between the proximal hub 5418 and a connector 5430 for releasable connection to a control system typically outside of the sterile field, to drive the pump 5422.

What is claimed is:

1. A device for transcutaneously transferring energy into a human body, the device comprising:

a first induction coil configured to be disposed in a patient's body;

a bar magnet at a center of the first induction coil, the bar magnet comprising a north pole and a south pole;

a second induction coil configured to be disposed outside of the patient's body, the second induction coil configured to provide a magnetic field for transferring energy to the first induction coil through the patient's body a plurality of sensors comprising three sensors arranged in a triangular configuration about a center of the second induction coil and a fourth sensor at the center of positioned within the triangular configuration the plurality of sensors configured to:

detect positional and orientational alignment between the second induction coil relative to the first induction coil when the fourth sensor measures a threshold voltage, a first sensor of the three sensors closest to the north pole measures a first voltage less than the threshold voltage, and a second sensor of the three sensors closest to the south pole measures a second voltage greater than the threshold voltage; and generate a signal based on the positional and orientational alignment of the second induction coil.

2. The device of claim 1, wherein the plurality of sensors comprises at least one Hall sensor configured to detect the relative position of the second induction coil.

3. A device according to claim 1 or 2, wherein the plurality of sensors comprises a gyro sensor configured to sense a spatial position of the second induction coil, and wherein the plurality of sensors are configured to provide a spatial signal based on the spatial position determined by the gyro sensor.

4. The device of claim 1, wherein the first induction coil comprises a permanent magnet configured to provide a magnetic field.

5. The device of claim 1 further comprising a control unit, the control unit comprising:

a non-transitory memory configured to store computer-executable instructions; and a hardware processor configured to execute the computer-executable instructions to at least:

control a voltage supplied to the second induction coil; and receive the signal form the plurality of sensors.

6. The device of claim 1 further comprising a display unit configured to display position information based on the signal provided by the plurality of sensors.

7. The device of claim 6, wherein the display unit comprises at least one light unit configured to visually display the position information.

8. The device of claim 6, wherein the display unit comprises at least one speaker unit configured to acoustically output the position information.

9. The device of claim 6, wherein the display unit comprises at least one vibration unit configured to output the position information haptically.

10. The device of claim 6, wherein the display unit comprises a display configured to output a graphical display of the position information, the graphical display comprising one or more of: a battery indicator, an alarm indicator, a connection indicator, or a system information display.

11. The device of claim 1, further comprising an alarm button for triggering of an emergency call.

12. The device of claim 5, wherein the control unit is detachably connected to the second induction coil.

13. The device of claim 5, wherein the control unit is integrated with the second induction coil.

14. The device of claim 5, wherein the control unit is disposed in a watertight and dustproof housing.

15. The device of claim 1 further comprising a positioning apparatus configured to position the second induction coil on the patient's body, the positioning apparatus comprising:

a receiving element configured to receive the second induction coil, wherein the receiving element is detachable from a mounting surface;

a wired connection configured to connect the receiving element and the second induction coil with at least one extracorporeal component; and a supporting element configured to receive and support the at least one extracorporeal component, the supporting element comprising at least one connecting element configured to detachably connect the at least one extracorporeal component to the supporting element.

16. The device of claim 15, wherein the receiving element is detachably connected to the second induction coil.

17. The device of claim 15 further comprising a positioning patch, the positioning patch configured to be positioned and attached to the human body by an adhesive, wherein the receiving element is a disposed on the positioning patch.

18. The device of claim 17, wherein the positioning patch further comprises a partially folded protective film disposed an exposed side of the adhesive and configured to protect the adhesive.

19. The device of claim 15, wherein the supporting element comprises a first fixing element, and wherein the receiving element comprises a second fixing element, and wherein the first fixing element and the second fixing element are configured to fix the receiving element and the supporting element, and wherein the first fixing element and the second fixing element comprising one of: a hook-and-loop fastener, a mechanical fastener, or a magnetic fastener.

20. The device of claim 15, wherein the supporting element comprises a textile layer configured to carry the positioning apparatus on the patient's body, wherein the textile layer comprises one or more conduits configured to connect one or more extracorporeal components of the device.

21. The device of claim 15, wherein the receiving element further comprises a groove element, and wherein the at least one connecting element comprises a tongue for insertion into the groove element.

22. The device of claim 15, wherein the receiving element further comprises a hook, and wherein the at least one connecting element comprises an eyelet configured to receive the hook.

23. The device of claim 15, wherein the receiving element further comprises a first electrical contact, and wherein the at least one connecting element further comprises a second electrical contact, and wherein the first electrical contact and the second electrical contact are configured to establish an electrical connection when joined together.

24. The device of claim 15, wherein the at least one connecting element is configured to releasably connect the at least one extracorporeal component to the supporting element.

25. The device of claim 15, wherein the at least one connecting element comprises a cable holder configured to guide a cable.

26. The device of claim 15, wherein the supporting element further comprises at least one belt for fixing the supporting element to the patient's body and at least one pocket for receiving the at least one extracorporeal component.

27. A method for transferring energy to a mechanical circulatory support system disposed in a human body using the transcutaneous energy transfer device of claim 1, the method comprising:

positioning the first induction coil inside the body;

positioning the second induction coil outside the body;

detecting a position of the second induction coil relative to the first induction coil;

generating the signal based on the relative position of the second induction coil;

aligning the first induction coil and the second induction coil concentrically based on the signal;

and generating an electrical current through the second induction coil, whereby the electrical current is inductively transferred from the second induction coil to the first induction coil through the body.

* * * * *